(12) United States Patent
Besson

(10) Patent No.: US 7,116,749 B2
(45) Date of Patent: Oct. 3, 2006

(54) METHODS FOR ACQUIRING MULTI SPECTRAL DATA OF AN OBJECT

(76) Inventor: Guy M. Besson, 1672 Emerald St., Broomfield, CO (US) 80020

( * ) Notice: Subject to any disclaimer, the term of this patent is extended or adjusted under 35 U.S.C. 154(b) by 4 days.

(21) Appl. No.: 11/133,114

(22) Filed: May 19, 2005

(65) Prior Publication Data

US 2005/0220265 A1    Oct. 6, 2005

Related U.S. Application Data

(63) Continuation of application No. 10/876,996, filed on Jun. 25, 2004, now Pat. No. 6,950,492, application No. 11/133,114, which is a continuation of application No. 10/877,006, filed on Jun. 25, 2004, and a continuation of application No. 10/877,019, filed on Jun. 25, 2004, now Pat. No. 6,950,493.

(60) Provisional application No. 60/482,819, filed on Jun. 25, 2003, provisional application No. 60/490,300, filed on Jul. 25, 2003, provisional application No. 60/490,291, filed on Jul. 25, 2003, provisional application No. 60/490,310, filed on Jul. 25, 2003, provisional application No. 60/490,299, filed on Jul. 25, 2003, provisional application No. 60/490,290, filed on Jul. 25, 2003.

(51) Int. Cl.
*A61B 6/03*        (2006.01)
(52) U.S. Cl. ..................... 378/16; 378/98.9
(58) Field of Classification Search .................. 378/4, 378/8, 15, 16, 98.9, 901
See application file for complete search history.

(56) References Cited

U.S. PATENT DOCUMENTS

2004/0028181 A1* 2/2004 Charles, Jr. et al. ........... 378/92
2005/0084069 A1* 4/2005 Du et al. .................... 378/98.9

* cited by examiner

*Primary Examiner*—David V Bruce
(74) *Attorney, Agent, or Firm*—Lathrop & Gage LC

(57) ABSTRACT

A multispectral X-ray imaging system uses a wideband source and filtration assembly to select for M sets of spectral data. Spectral characteristics may be dynamically adjusted in synchrony with scan excursions where an X-ray source, detector array, or body may be moved relative to one another in acquiring T sets of measurement data. The system may be used in projection imaging and/or CT imaging. Processed image data, such as a CT reconstructed image, may be decomposed onto basis functions for analytical processing of multispectral image data to facilitate computer assisted diagnostics. The system may perform this diagnostic function in medical applications and/or security applications.

55 Claims, 41 Drawing Sheets

METHODS FOR ACQUIRING MULTI SPECTRAL DATA OF AN OBJECT

RELATED APPLICATIONS

This application is a continuation of Ser. No. 10/876,996, filed Jun. 25, 2004 now U.S. Pat. No. 6,950,492; which claims benefit of priority to application Ser. Nos. 60/482,819 filed Jun. 25, 2003, 60/490,300 filed Jul. 25, 2003, 60/490,291 filed Jul. 25, 2003, 60/490,310 filed Jul. 25, 2003, 60/490,299 filed Jul. 25, 2003, and 60/490,290 filed Jul. 25, 2003.

This is a also continuation of Ser. No. 10/877,006, filed Jun. 25, 2004; which claims benefit of priority to application Ser. Nos. 60/482,819 filed Jun. 25, 2003, 60/490,300 filed Jul. 25, 2003, 60/490,291 filed Jul. 25, 2003, 60/490,310 filed Jul. 25, 2003, 60/490,299 filed Jul. 25, 2003, and 60/490,290 filed Jul. 25, 2003.

This is also a continuation of Ser. No. 10/877,019, filed Jun. 25, 2004 now U.S. Pat. No. 6,950,493, which claims benefit of priority to application Ser. Nos. 60/482,819 filed Jun. 25, 2003, 60/490,300 filed Jul. 25, 2003, 60/490,291 filed Jul. 25, 2003, 60/490,310 filed Jul. 25, 2003, 60/490,299 filed Jul. 25, 2003, and 60/490,290 filed Jul. 25, 2003. All of the aforementioned application are hereby incorporated by reference.

BACKGROUND

1. Field of the Invention

The invention pertains to dynamic multispectral x-ray imaging of objects, such as an object, animal, tissue sample, or human body.

2. Description of the Related Art

X-rays are generated by a high voltage X-ray tube that is driven by a control unit and interconnected through cabling to a high-voltage generator. A beam of the X-rays pass through a subject body during X-ray examination and onto an X-ray detector array. The X-ray detector array may be a flat panel detector, for example as described in U.S. Pat. No. 6,403,965 issued to Ikeda et al. Other detection devices are known, for example, a charged coupled device (CCD) formed as a regular array of light sensitive cells and coupled to an x-ray attenuation layer such as a scintillator or a photoconductor, as shown and described in U.S. Pat. No. 5,454,022 issued to Lee et al. Various manufacturers produce large format CCD devices for use in X-ray detection applications. Alternatively, the X-ray detector maybe a flat-panel array with amorphous Silicon (a-Si) substrate with either a scintillator layer such as CsI, or a direct convertor material such as Cadmium Zinc Telluride (CZT), Mercuric Iodide (HgI2), Lead Iodide (PbI2), or amorphous Selenium (a-Se).

In a CCD, electric charge builds up in each element of the detector array in proportion to the integral (as function of energy) of the intensity of the X-rays impinging on the element. To take a measurement, the charge in each of the cells is set to zero (or a corresponding nominal level), the array is exposed to the X-rays, and the charge accumulates over a period of integration. At the end of the integration period, the accumulated charge is transferred to a measurement circuit in a regular and known sequence. The result of this process is a series of measurements (one for each element in the array) that relates to the magnitude of X-rays passing through, and through inference absorbed by, the subject body. Each of the elements of the detector array corresponds to a unique straight-line path from the X-ray source center through the subject body to the detector element center. Equation (P.1) shows Beer's Law, which defines the line integral of the absorption of any given path through the subject body:

$$I = I_0 \int_{spectrum\ E} \exp\left\{\int_0^d \mu(x, E)dx\right\} dE \qquad (P.1)$$

where I=Output X-ray intensity level;

I$_0$=Incident X-ray intensity level;

E is one of the energies comprising the x-ray spectrum;

$\mu(x)$=Attenuation at a point on the X-ray path through the subject; and

[0,d] represent the length of the X-ray path under consideration.

Modern digital x-ray systems often include an automated software analysis package. Breast cancer screening investigations today provide the best case study of computer assisted diagnosis (CAD) approaches. The potential of CAD to improve chest radiography, chest CT, and other medical examination accuracy is the subject of much on-going research. Current CAD products and algorithms tend to have low specificity when used alone without the judgment of a radiologist, as applied to breast cancer screening, and help mostly less experienced readers. Yet several studies have suggested that CAD can improve upon a radiologist's ability to detect and classify lesions in mammography and such findings are likely in chest imaging and in other applications as well. Automatic detection of lung nodules is the most studied problem in computer analysis of chest radiographs. Nodules typically present as relatively low-contrast densities within the lung fields. The challenge for CAD in chest radiography is to distinguish true nodules from overlapping shadows of ribs and vessels. Computer approaches might prove essential to the practicality of measuring two of the best predictors of module malignancy: nodule size and growth rates.

Patient and population X-ray exposure and dose concerns have been heightened in recent years. In particular, computed tomography (CT) and MDCT examinations have increased in number and frequency; the annual number of CT examinations in the United States increased almost 10-fold in less than 20 years. In the decade preceding the introduction of MDCT (1980 to 1990), the number of CT exams increased from 3.6 million to 13.3 million. In the United States, CT accounts for only 11 percent of the total X-ray examinations, yet it contributes about 66 percent of the total delivered dose. Worldwide the corresponding percentages are approximately 5 and 34 percent. In lung imaging, CT has demonstrated significant sensitivity, but its relatively low specificity has raised concerns about the likelihood of significant changes in patient outcomes.

Dose concerns, the worldwide health impact of tobacco use, and the frequency of chest X-ray examinations all contribute to the urgency and significance of finding low-dose means of detecting lung cancer and other diseases. By intrinsic design, and for a given X-ray absorption technology, a narrow-beam scanning system provides the optimal means to lower patient dose, due to the absence of a Bucky grid. For a given detector technology and X-ray beam spectrum, a scanning approach offers the best DQE possible, provided the beam penumbra is utilized and the scan mechanism is appropriately designed to minimize system losses.

As illustrated, FIG. 1 shows one prior art digital X-ray system. Projection imaging or CT system 10 includes an X-ray source 12, an X-ray detector array 14, and a subject body 16. X-ray source 12 and X-ray detector array 14 are maintained in a fixed geometric relationship to one another by means of a gantry for the duration of an exposure (not shown) permitting selective rotation 18 about a fixed axis 20 that is generally coaligned with body 16 or another axis of rotation. Each X-ray exposure is taken from a nominal position causing X-rays 21 to pass through section 24 of subject body 16. The detector array 14 provides electronic signals commensurate with the absorption of X-rays 21 after passage through section 24, and these signals constitute measurements of properties encountered in section 24. The measurement data are representative of the integral of the body X-ray linear attenuation coefficients along paths 21.

Computing equipment 22 receives signals from the detector array 14 and processes these signals. By application of such mathematical processes as projection data calibrations, corrections, and image reconstruction, the signals are converted to an image of section 24. The image can then be examined, for example, on a video display 26.

Subject body 16 may be placed on a moveable platform 28, which is moved by an electric motor 30 under the control of the computing equipment 22. As desired, additional images may be obtained from the subject body 16, e.g., at a different location, at different platform locations relative to X-ray source 12 and detector array 14.

In another mode of operation, the projection imaging system 10 of FIG. 1 may be used to provide CT scans. X-ray source 12 and X-ray detector array 14 are maintained in a fixed geometric relationship to one another by means of an automated gantry (not shown) as they are both rotated 18 about a fixed axis 20 generally coaligned with body 16. In this rotation, X-ray detector array 14 and X-ray source 12 are continuously rotated about the body 16 to complete a circle about body 16. The X-ray exposure typically is continuous and a series of projection measurements are acquired at a multiplicity of positions or projection angles around the body. After completion of a source rotation, the subject position may be incremented by a pre-determined amount, and the examination continues.

These measurements are collected by computing equipment 22. By application of mathematical processes, this set of measurement results is converted to tomographic map of a section 24 of body 16. The tomograph can then be examined, for example, on a video display 26.

Subject body 16 is generally placed on a moveable platform 28, moved by an electric motor 30 under the control of the computing equipment 22. As desired, a further scan section 24 may be made, e.g., at a different location, at different platform locations relative to X-ray source 12 and detector array 14, to generate a more complete 3D representation of subject body 16. Scanning is often performed in a "helical" mode, where platform 28 advances continuously as X-ray detector array 14 and source 12 rotate. The timing of the detector cell samplings determines the geometry of the X-ray paths through the body. The measurement data are representative of the integral of the body X-ray linear attenuation coefficients along these paths. In such modes the X-ray source may be energized continuously during the examination time.

It is also appreciated that in a CT system, the subject table may be advanced while the source and detector remain at a fixed spatial position (a "Scout" mode). In such a situation a fixed point in the subject body is projected through the various detector rows as a function of time.

Unfortunately, one problem with system 10 is that the tomographic map of section 24 can be used to identify relatively few constituents of body 16, and measurements lack quantitative accuracy.

The X-ray source 12 and X-ray detector array 14, as connected by the gantry, define an imaging chain, and are maintained in a defined geometric relationship to one another by means of a gantry. The source-to-detector distance may be varied depending on the examination, and the angle of the imaging chain can be adjusted with respect to the body to be imaged.

System 10 may be adapted for use in security applications, such as airport security screening of luggage, or industrial applications where it is desirable to X-ray a part or package.

SUMMARY

The instrumentalities described herein overcome the problems outlined above by providing method and apparatus for-use in multispectral X-ray imaging applications that may be used to improve measurements and diagnostic results. For example, in medical applications these instrumentalities may improve lesion conspicuity and patient outcomes. Use of co-registered multi-spectral data may improve the efficacy of CAD algorithms in detecting, characterizing, and classifying lung and other lesions. In other applications, threat diagnosis may be improved, for example, by diagnosing that threat-related materials are present, such as a firearm, explosives, shielded nuclear materials, and radiological dispersal devices.

Using multi-spectral data acquisition in a single scan, as described below, advantageously eliminates motion and mis-registration artifacts between the various multi-spectral projections. Co-registered elimination of bone superposition may bring significant improvements in lesion conspicuity. Use of multiple energies may further improve separation of body constituents and allow better anatomy visualization and lesion characterization, particularly in the presence of contrast medium. As applied to chest imaging, better imaging test accuracy, in conjunction with improved lung cancer treatment and management techniques, may provide better long-term patient outcomes. The rate of false negatives may be improved, as compared to conventional chest radiography. The rate of false positives may also be reduced through improved contrast, conspicuity, and characterization. A reduced rate of false positives may reduce the burden on the patient and the healthcare system, by avoiding costly unnecessary and potentially harmful follow-up and interventions. Similar advantages are obtained in security and industrial applications.

Systems and methods are described to dynamically and adaptively vary the X-ray spectrum, during a scan of the body, to produce a set of results that differentiate a far wider range of body constituents and improve image contrast in substantially the same examination time as compared to the prior art.

In one embodiment, a method is provided for obtaining multi-spectral data through a body, where in one embodiment the method steps may include:

(a) projecting X-ray radiation along paths through a body by scanning a beam of X-ray radiation with respect to the body in synchronicity with system configuration for selective emission of the X-ray radiation having M sets of spectral characteristics, the paths extending from an X-ray source to a detector;

(b) detecting the X-ray radiation with a plurality of detector cells or elements that each define an X-ray path terminus;

(c) generating a plurality of signals representative of attenuation of the X-ray radiation on the X-ray paths, the plurality of signals allocated to one of the T sets of measurements (with M≦T);

(d) iterating through the above steps (a) through (c) to acquire T measurements for substantially the same X-ray paths through the body, each measurement taken from differentiated source spectra in consequence of the projecting step (a) to provide multispectral projection data in M sets of measurements where M<=T; and (e) processing the multispectral projection data in M sets to obtain image data decomposed onto basis functions representative of body constituents, and to obtain analytical results indicative of a diagnostic condition.

The projection imaging method may be implemented using commercially available components that have been assembled to operate as described above when programmed with instructions to implement the multispectral processing. The selection of M spectra may be facilitated by a wideband source X-ray tube used in combination with a specifically constructed filtration system for selection of a specified one of the M spectral sets.

The wide-band X-ray source may be used in conjunction with detectors that have the capability of count individual photon events and determine the energy of each such X-ray. The systems and methods described below may process the data acquired in T sets of measurements for M spectra and decompose them onto a set of N basis functions representative of body constituents. The processing may, for example, proceed on the basis of spectral and spatial relationships between the T sets of measurements each allocated to a different one of the M spectra, and/or among the T sets of measurements allocated between the M spectra. An ability to dynamically adjust spectral selection in synchrony with scanning excursions is particularly advantageous when used with the wideband source and filtration assembly.

The basic projection system may be adapted or arranged to implement a method of CT imaging, for example, including the steps of:

(a) projecting X-ray radiation along paths through a body by scanning a beam of X-ray radiation with respect to the body in synchronicity with system configuration for selective emission of X-ray radiation having M sets of spectral characteristics, the paths extending from an X-ray source to a detector and with an x-ray source excursion and detector configuration allowing acquisition of sufficient data for at least one of a tomographic reconstruction and a tomosynthesis reconstruction;

(b) detecting the X-ray radiation with a plurality of detector cells or elements that each define an X-ray path terminus;

(c) generating a plurality of signals representative of attenuation of the X-ray radiation on the X-ray paths, the plurality of signals allocated to one of the T sets of measurements (with M≦T);

(d) iterating through the above steps (a) through (c) to acquire T measurements in M sets of spectra in consequence of the projecting step (a) to provide multi-spectral projection data, the iterations being performed in such a manner that there is spatial commonality between respective ones of the T sets of measurement where each one of the T sets of measurements is substantially spatially aligned with at least a subset of another of the T sets of measurements; and (e) processing the multispectral projection data to provide first information for a at least one of a tomographic and a tomosynthesis reconstruction, to obtain image data decomposed onto basis functions representative of body constituents, and to obtain analytical results indicative of a diagnostic condition.

The CT imaging method may be implemented using commercially available components that have been assembled to operate as described above when programmed with instructions to implement the decomposition. The selection of M spectra may be facilitated by a wideband source X-ray tube used in combination with a specifically constructed filtration system for selection of a specified one of the M spectral sets. The wide-band X-ray source may be used in conjunction with detectors that have the capability of count individual photon events and determine the energy of each such X-ray. An ability to dynamically adjust spectral selection in synchrony with scanning excursions is particularly advantageous when used with the wideband source and filtration assembly.

In CT applications, by linearity of the CT image reconstruction process, the decomposition onto basis functions may take place on the projection data, and then a tomographic reconstruction is obtained for each basis-function decomposition for each slice of interest through the body. Alternatively, each acquired multi-spectral projection data (for a given slice of interest through the body) may be reconstructed to yield a stack of multi-spectral tomographic images for the slice of interest though the body. This stack of tomographic images is then decomposed onto a set of two-dimensional basis functions (tomographic images) for each slice of interest through the body.

In either case, the process of CT image reconstruction may be performed by standard filtering-back projection approaches, or by iterative approaches based on a statistical model or other model of the projection data. These later approaches will be preferred when each of the multi-spectral projection data sets (for a slice of interest through the body) includes a limited number of detected X-ray photons, as such methods are better able to handle noisy data and incorporate a-priori information (in the model).

In other aspects, the system may contain a processing algorithm that operates according to program instructions to analyze detection signals representing a plurality of bands or peaks in the X-ray radiation. By way of example, where the X-ray radiation is successively filtered to provide a plurality of predetermined bands, the detected energy or intensity according to each band may be used to form a series of measurements representative of source spectra and body attenuation at each spectrum, said series covering the entire desired spectral bandwidth for each detector of a detector array. The series of measurements (all corresponding to substantially a fixed geometrical path through the body) may be decomposed onto a set of basis functions representative of known materials or body constituents.

In CT applications, each projection data set corresponding to one basis function may be reconstructed to form a (tomographic) slice image representative of the spatial distribution of a body constituent or known material. Differences or similarities between the decomposed line integral maybe statistically processed for use as a diagnostic aid, for example, by selecting such differences if they exceed a predetermined range of delimiting values, and superimposing a positional field of such excess values on a base image of the body. The processing may operate either on the projection data or, preferably, on the stack of decomposed reconstructed tomographic images for each slice of interest through the body. In other instances, statistical processing may occur with the aid of a neural network that has been trained to using full-spectrum peaks or other multi-spectral data.

The CT system may provide a scout or preview mode of operation wherein for example, a multispectral scan may be used in a scout acquisition to mode to define scan limits of the scan with respect to the patient longitudinal axis, to refine acquisition technique, and to get a first perspective of the body. The scout mode may be used in place of substitution of a standard x-ray projection image, and may be performed in multispectral mode.

BRIEF DESCRIPTION OF THE DRAWINGS

FIG. 25 shows an imaging system in CT operation.

DETAILED DESCRIPTION

Figure 2:
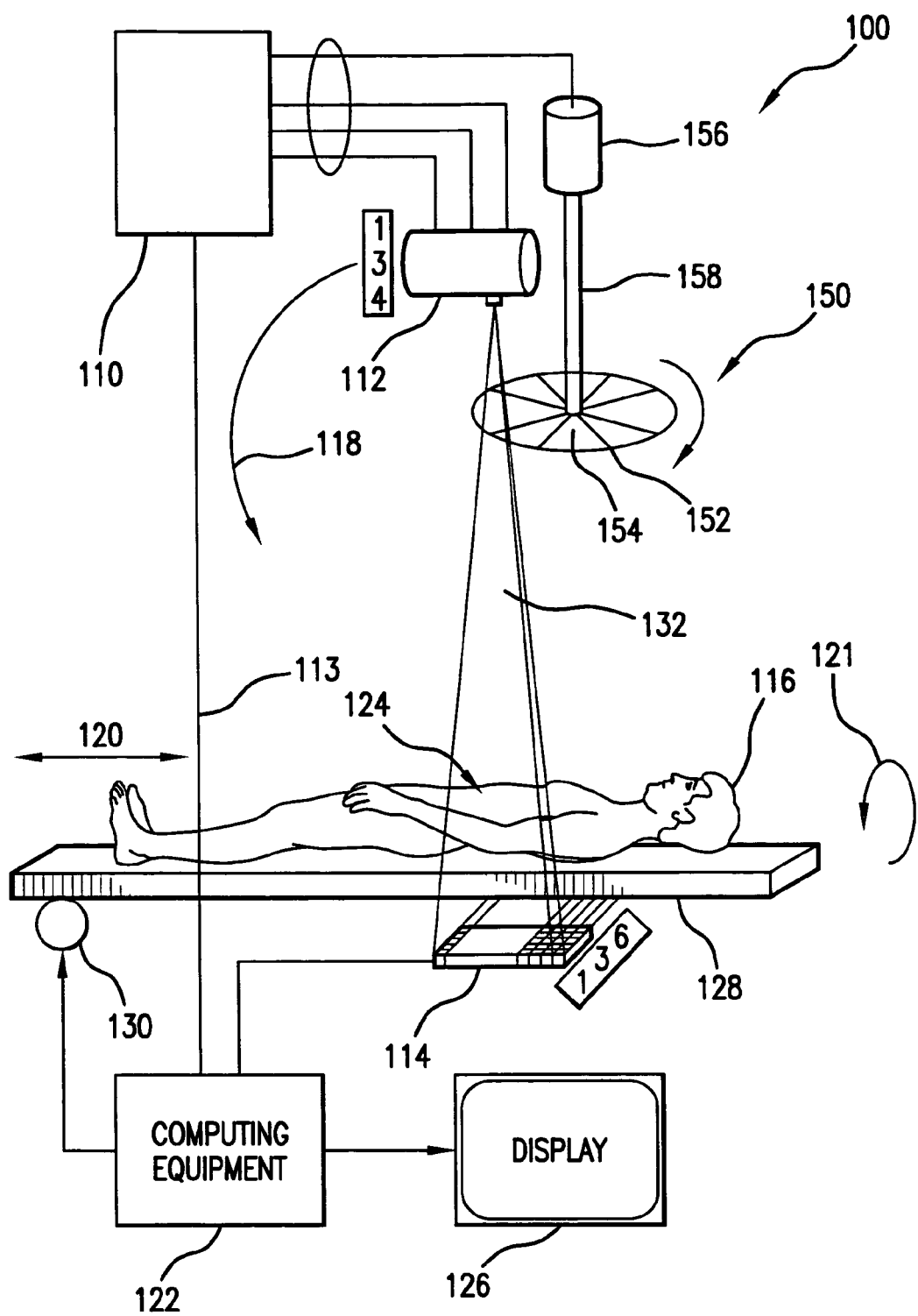
FIG. 2 is a schematic diagram illustrating a multi-spectral imaging system that may be used for projection imaging or CT applications.

FIG. 2 shows, by way of nonlimiting example, one X-ray system 100 constructed in accordance with the teachings hereinbelow. X-ray system 100 may be used to differentiate a greater number of constituents in a body 116 as compared to the prior art, by capturing a range of different X-ray energies through a body section 124 during a measurement sequence. The precise design elements of system 100 reflect a system design approach that accommodates both the human observer and the specific imaging task, for example, using psycho-physiological studies to enhance parameter selection for optimal performance. It will be appreciated that the body 116 as shown is a human body, but may also be an animal, plant, or inanimate object, such as luggage or a parcel.

In particular, system 100 includes an X-ray source 112 and an X-ray detector array 114. X-ray source 112 generates X-ray radiation on paths 132 that passes through body 116 for capture by X-ray detector array 114. In one embodiment, the geometric relationship between source 112 and array 114 is not kept constant, but varies to accommodate detector movement relative to source 112. In another embodiment, a mechanical assembly (not shown) linking the source 112 and detector array 114 is used to ensure that motion of the detector array is matched by a corresponding X-ray source rotation so that the X-ray illumination pattern onto the detector remains substantially fixed. The mechanical assembly may be such that the source 112 and detector array 114 move along an arc 118 centered at a focal point of X-ray source 112, and/or translates linearly along axis 120. These movements assure that the relative position of the X-ray paths 132 with respect to the body 116 changes as a function of time.

In another embodiment shown below, a beam scanning mechanism is used to ensure sweeping of a narrow x-ray beam across the face of an area detector, with or without other concurrent sub-system motions.

During a measurement sequence, source 112 generates X-ray radiation on paths 132, and the X-ray radiation passes through body 116 towards detector array 114. The spectrum of radiation may be varied such that each measurement for a given position or a plurality of measurements for a given position corresponds to a different spectrum. In one embodiment, X-ray radiation 132 is filtered at each sequence and measurement position by filter 150 to accomplish this spectral differentiation. The filter 150 rotates with motion 152 to interpose one of a plurality of sectors 154 into paths 132. Each of sectors 154 may have a different filter element that selects for a sub-band of X-ray radiation emitted by source 112, or some of the sectors 154 may be the same to effect spectral changes through other tube parameter changes. The filter 152 may be rotated by motor 156, as needed.

In another embodiment, there is no fixed mechanical linkage between the source 112 and the detector array 114, rather, the source 112 and/or detector array 114 are driven directly by independent motive devices 134, 136. Relative positioning may be optimized through use of a feed-back loop or by determining in real-time the position of the projected paths 132 onto the detector array 144. Accordingly, for example, the rotation or motion of source 112, e.g., on arc 118 or another trajectory may driven through the feed-back loop as a result of the independent motion of detector array 114.

In one embodiment, the detector array 114 is arranged to capture the primary X-ray beam constituting paths 132, and also to capture scatter outside of the primary X-ray beam, as well as allowing for the precise measurement of the X-ray beam profile.

System 100 has computing equipment 122 that processes a computational algorithm, which is described hereinbelow, to process the data captured by system 100 and generate imaging results for output to display work station 126. Computing equipment 122 controls the geometric relationship between source 112 and array 114, and is operable to control the position of source and collimator assembly 134 and array 114 during a measurement sequence.

The display workstation 126 may be designed to use Windows-based software and a PC architecture. Use of a high-resolution monitor, e.g., five mega-pixels, is preferred. Such displays are available off-the-shelf in CRT or LCD flat-panel technology and have been approved by the FDA for demanding applications such as mammography. Image display modes will include one-image-per monitor, full-resolution presentation with panning capability, and various zoom levels. Images are displayed according to DICOM Standard 14.3 (gray scale function) and may be provided in a DICOM-compliant format for network and PACS interfaces In one mode of operation, that of scout mode, subject body 116 is generally placed on a moveable platform 128 which is moved by an electric motor 130 under the control of the computing equipment 122. Motion may extend platform 128 along axis 120, and/or tilt platform 128 to selected positions on arc 121 for different presentational alignments of body 116 with respect to paths 132.

In another embodiment, such as CT scanning, the geometric relationship between source 112 and detector array 114 is kept substantially constant. The source 112 and detector array 114 are rotated around body 116 and axis 120, with or without body translation through the system along axis 120.

In another embodiment, known as fourth-generation CT scanning, the X-ray source 112 rotates around body 116 and the detector array 114 stays in a fixed position. This is possible because the detector array 114 has an area extent such that multi-row detectors are arranged on a circle or arc of a circle around the system axis that is complementary to variable positioning of source 112 for receipt of X-rays on the full effective range of paths 132 on arc 118.

The spectrum of X-ray radiation on paths 132 passing through section 124 may be varied according to different techniques for operating a given X-ray source 112, so long as there is sufficient response time to maintain an acceptable scan rate of body 116. For example, the operating technique under control of computing equipment 122 may vary X-ray tube voltage as a difference in voltage between the anode and cathode of a conventional X-ray tube to emit different spectra. Other such techniques are to vary X-ray tube electron beam current, the X-ray tube target material selection, the X-ray focal-spot geometry, and/or the X-ray filtering by filter 152 or other filters in paths 132. These techniques may be employed individually or cooperatively at the same time.

In the cases where X-ray spectra are varied by -ray tube voltage and/or electron beam current, a control unit 110 may connect to computing equipment 122 via signal line 113. Control unit 110 acts on instructions form computing equipment 122 to vary the voltage or current of source 112 and adjust the emitted spectrum of X-ray radiation 132 in a predetermined or calibrated way. Filter 150 is driven under control of computing equipment 122 to select for sub-band. Control unit 110 may also, for example, adjust the electron beam current in X-ray source 112 to compensate for X-ray losses by filter 150 and/or variations due to anode voltage. Additionally, the geometric properties of the x-ray source focal spot are also under control of unit 110. Those skilled in the art appreciate that control unit 110 and computing equipment 122 may be combined into a single unit without departing from the scope hereof.

In cases where X-ray spectra are varied by X-ray tube target material selection, a source 112 may be used with multiple selectable target material. The response time for such sources are compatible with the time of a measurement. A new X-ray tube is described hereinbelow that enables dynamic target material switching.

In cases where X-ray spectra are varied by X-ray filtering, this entails selecting for a sub-band of the total spectrum emitted by source 112. Filter 150 may be a filter disk, as shown in FIG. 2, with several radial sections or sectors 154. In one embodiment, each section or sector 154 of disc 152 is made from a material selected for its X-ray filtering characteristics, and the filter characteristics preferably differ from one another. One of the sections 154 may be unfiltered, for example, to provide calibration and/or broadband spectrum imaging. Under control of the control unit 110 and computing equipment 122, motor 156 and drive shaft 158 rotate disc 152 synchronously with scan measurement to provide the desired spectrum in radiation on paths 132.

Figure 3:
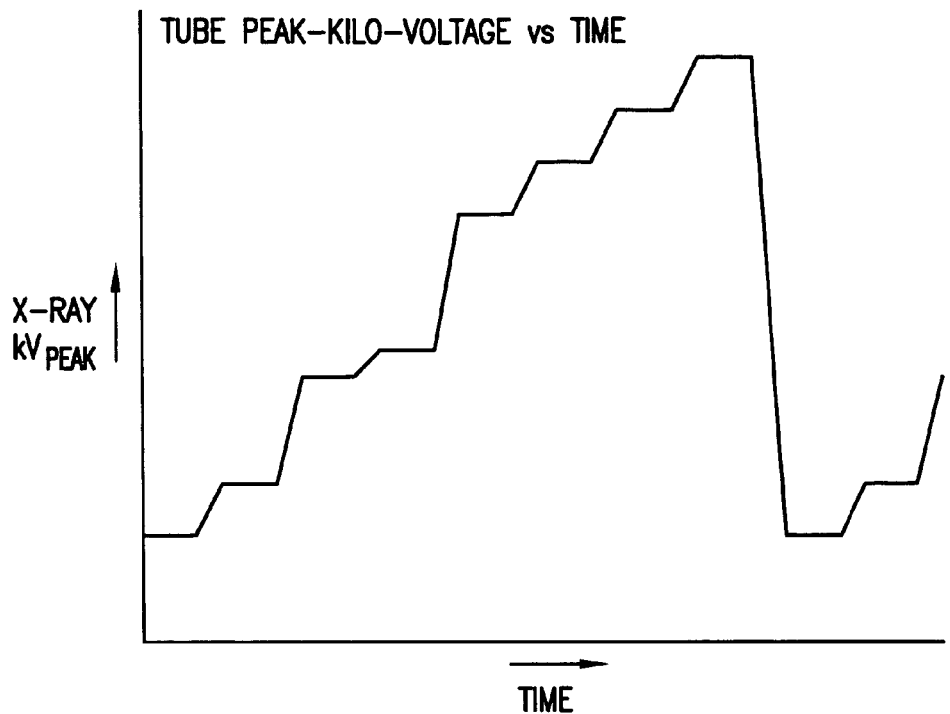
FIG. 3 illustrates changes in X-ray emission spectra that may be derived from differences in X-ray tube voltage.
Figure 4:
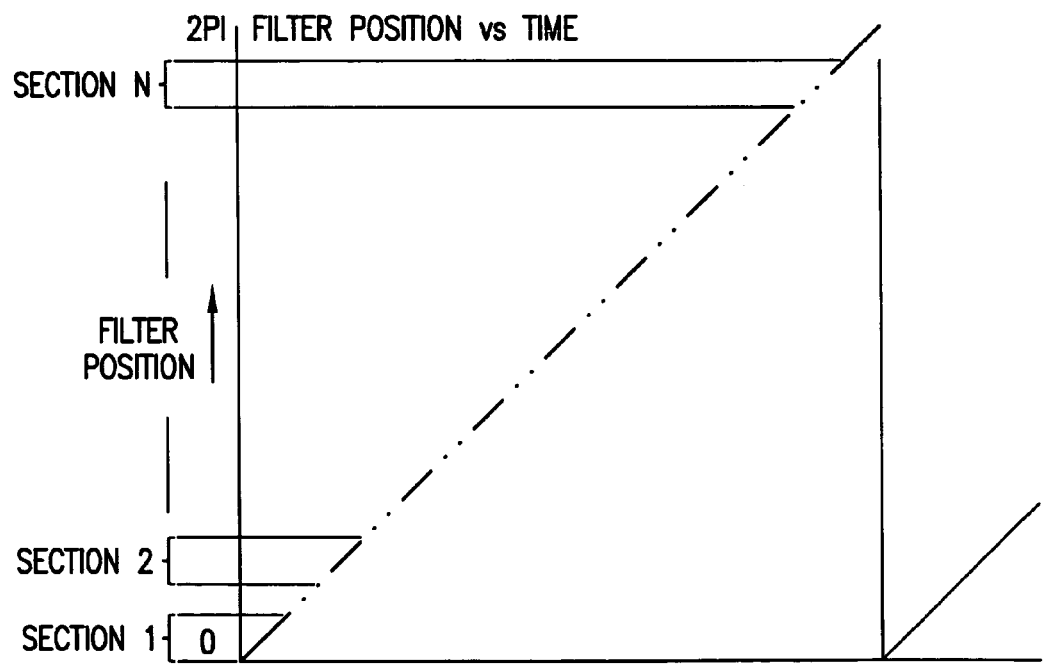
FIG. 4 shows the advance of several filter sections through the x-ray beam as a function of time.

FIG. 3 and FIG. 4 show two graphs illustrating how X-ray spectrum may vary with filter selection, over time and per section 124 of body 116. FIG. 3 shows that the emission spectra of source 112 may be driven by variable voltage over time with consequent differences in emission spectra as indicated by changes in X-ray kilovoltage peaks. The variable emission spectra shown in FIG. 3 may be matched to a filtering mechanism, such as filter 154, to provide filtered spectrum including sections 1, 2, . . . N by virtue of the filter positioning.

Figure 5A:
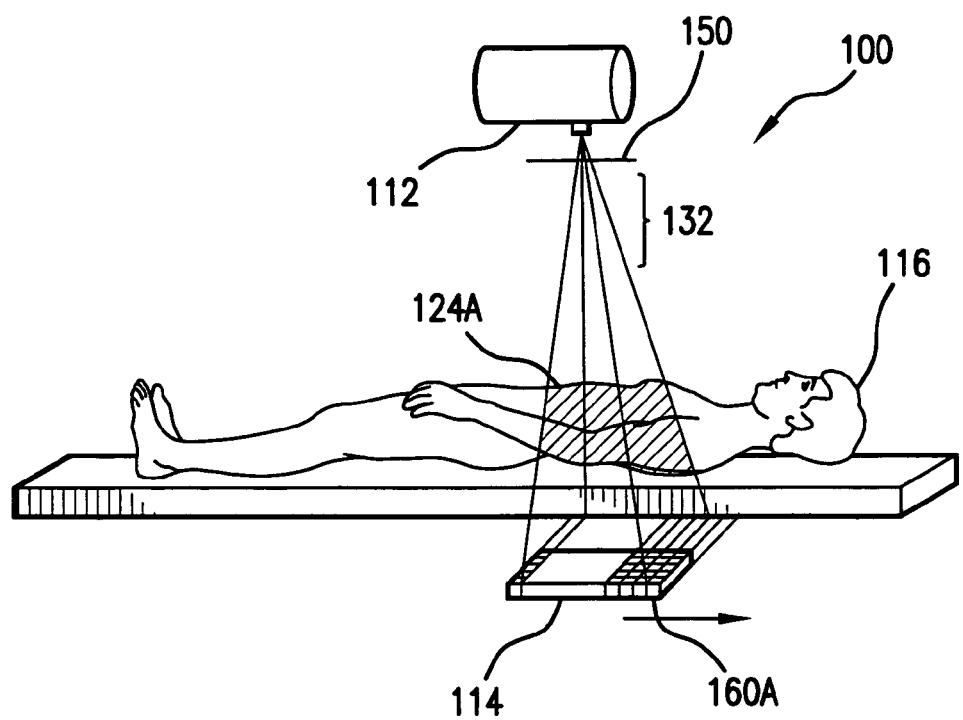
FIG. 5a shows a first imaging excursion at a first emission spectra.
Figure 5B:
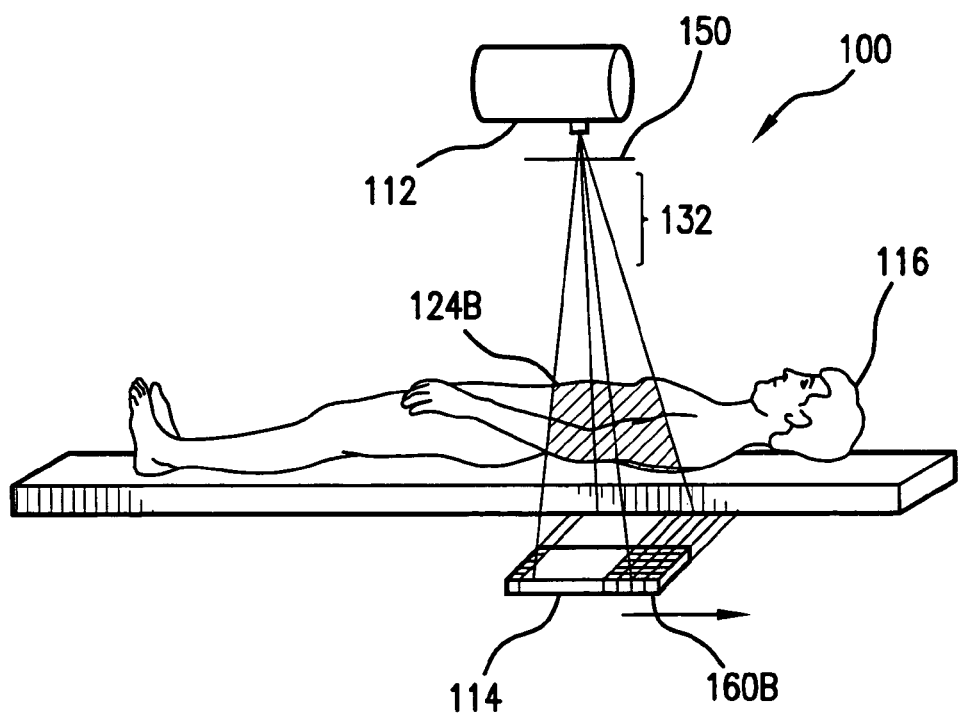
FIG. 5b shows a second imaging excursion at a second spectra.

FIG. 5A and FIG. 5B illustrate an exemplary scan techniques to obtain further sectional images of body 116. It is noted that the range of applied kVp and tube current may be changed adaptively and dynamically as a function of the amount of attenuation that the body 116 presents to the X-ray beam, while any point in the body 116 will be examined by X-rays at a multiplicity of spectra. System 100 of FIG. 2 may have several applications or modes of operation, as described below including, for example, uses in volumetric CT, projection imaging, scout or preview operations, spiral CT, and/or limited-angle CT For volumetric computed tomography, there are several rotations of X-ray source 112 and detector array 114 around body 116. The configurations of source 112 and array 114 are fixed for each rotation at a particular spectrum. This application is of particular use, for example, with newer CT scanners utilizing flat-panel detectors or multi-row detectors and sub-second rotation, as the subject or subject organ of interest may be probed with a multiplicity of spectra, each associated with a full X-ray source rotation. The spectra transitions from rotation-to-rotation may be accommodated by use of generalized under-scan weighting or over-scan weighting. Further, due to the double sampling of each line integral that occurs in a single source rotation, two spectra may be used, per rotation, thereby either reducing the total examination time or increasing the number of subject constitutional elements that may be identified and characterized. This may also be generalized to helical/spiral CT imaging, where at each source rotation (or each half source rotation), a fixed point in the subject projects onto a different row of the multi-row detector. In such a case, the X-ray source spectrum may be varied over a range including a number of settings that is an integral divisor of the total number of rows.

In certain embodiments for projection X-ray imaging, the X-ray beam on paths 132 may be narrowed to irradiate a limited area of detector array 114. Exposure is made at one spectrum. Detector array 114 and the paths 132 beam are moved, synchronously, so that substantially the same active part of the detector array 114 is irradiated by the second exposure at a different spectrum. This process is repeated for all desired spectra. By way of example, FIG. 5A and FIG. 5B illustrate two consecutive measurements, where, body 116 is exposed to x-ray beams while array 114 captures X-ray radiation in a first exposure measurement on rows 160A shown in FIG. 5A. Filter 150 is set to provide a first emissions spectra on paths 132 for imaging section 124A. Detector array 114 captures X-ray radiation representing section 124B at a second spectrum or a second exposure measurement in rows 160B shown in FIG. 5B. The first spectrum and the second spectrum may have different clinical utility, for example, where constituents of body 116 have different conspicuities under the different spectra or lesions of interest may have different X-ray absorptions indicative of disease under the respective spectra. The areas 124A, 124B may be the same areas, or they may overlap. During the scan, each X-ray path is sampled a total of T times. T may be equal to the number of detector rows, or T may be larger than the number of detector rows, as in the case of oversampling, or T might be less than the number of detector rows, as in the case of electronic binning of the detector rows. The total number of measurements T for a given X-ray path is allocated onto M sets, each comprising $T_i$ measurements, with:

$$0 \leq T_i \leq T, i=1, \ldots M,$$

subject to:

$$T = T_1 + T_2 + \ldots + T_M$$

Accordingly, for each change of spectra, each position in the body is imaged onto a different detector row or segment of rows. Thus, for each of M changes of spectra, detector increments will generate $T_i$ measurements, $i=1, \ldots, M$, with each path-location in the body being sampled a total of T times.

X-ray paths 132 that are sampled T times may not be exactly superimposed; however, exact superimposition is an ideal case. The instrumentalities of this disclosure may be attained by substantially sampling the same paths T times with M different spectra. The precise tolerances for substantially the same paths may vary depending upon the intended application or environment of use. By way of example, in projection imaging application for a chest imaging purposes, a beam of 12-mm at the detector combined with a typical source-to-image distance of 180-cm leads to a maximum angle between paths of 0.38-degrees. Such a difference usually does not lead to any noticeable artifacts in the decomposed multi-spectral images; nor would typically an angle difference of up to a few degrees lead to any noticeable artifacts. Similarly, in CT applications, considering a detector extent of 40-mm, and a typical source-to-detector distance of 100-mm, the maximum angle between two samplings of substantially the same ray would be 2.29-degrees. It is known in the art that cone-angles (or deviation angles from a plane) of 2-degrees of less do not lead to substantial cone-angle artifacts in reconstructed images. Accordingly, it is clear that using a multi-row detector to substantially achieve T samplings of a given geometric ray in either projection or CT imaging may provide image quality that is not degraded in comparison to the image that would be obtained by sampling T times exactly the same X-ray path.

Projection X-ray imaging may be enhanced by various system features for different modes of operation. For example, paths 132 may constitute a scanning beam, such that scanning speed is enhanced by the provision of a detector array 114 that is fixed and of large area construction. Alternatively, the scanning beam may be complemented by a moving detector array 114, where the primary beam projection onto the detector changes as a function of time.

System 100 may be operated in CT scout/preview mode. Here, body 116 is scanned without rotating the source 112 and detector array 114. For this use, the detector array 114 is preferably a multi-row detector or flat-panel array.

System 100 may be operated for CT imaging in spiral mode. In this application, body 116 moves along the axis of the scanner as the array/source rotate. For each successive rotation, body 116 is moved a fraction of the length of the array, where for illustration that fraction is the reciprocal of the number of spectra. Accordingly, a scan for each spectrum appears on successive portions of array 114. For this use, the detector array 114 is preferably a multi-row detector or flat-panel array.

Another mode of operation is that of limited-angle CT, where the X-ray source travels along a path, such as an arc of a circle, line segment, or another path, to acquire a multiplicity of projections to enable limited-angle CT image reconstruction or tomosynthesis image reconstruction.

Certain advantages may also be realized by the features hereof. For example, detection over a range of spectra permits finer differentiation of constituents of body 116.

Figure 6:
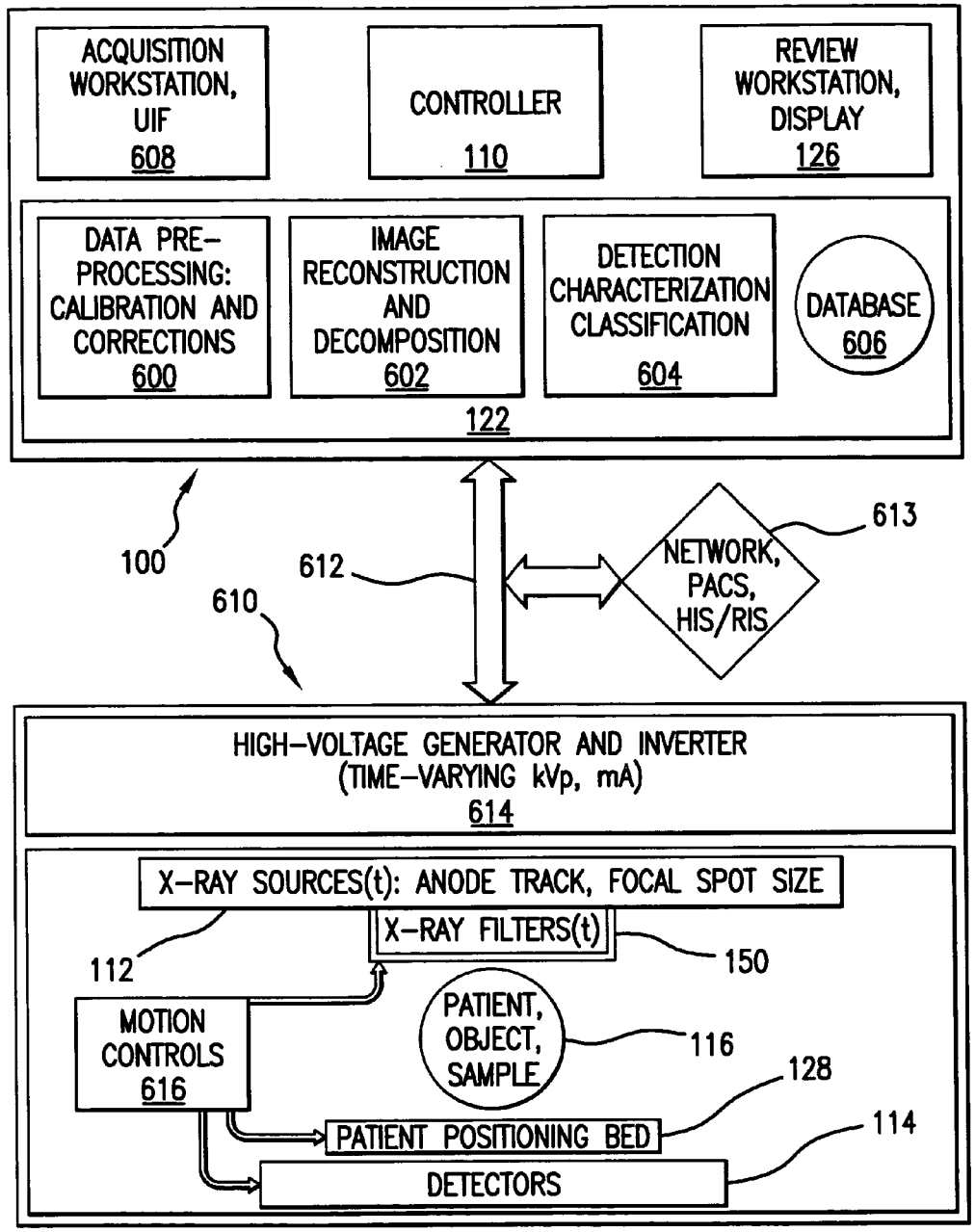
FIG. 6 is a schematic block diagram of one imaging system for use in multi-spectral X-ray imaging.

FIG. 6 provides additional detail with respect to one embodiment of elements for use in system 100. Computing equipment 122 is programmed with modules including algorithms for data preprocessing and corrections 600, image reconstruction and decomposition 602 and detection, characterization, and classification 604. A database 606 may be provided to contain data in support of calculations according to those modules. The computing equipment 122 is operably coupled with controller 110 and the review workstation display. One or more additional workstations may be added to facilitate operations, such as measurement acquisition workstation 608.

Computing equipment and controller 110 are operably networked to a gantry assembly 610, and possibly other hospital systems (not shown), for example, by network connections 612 including PACS, HIS/RIS or other system protocols 613. The gantry assembly 612 contains cooperatively linked segments including, for example, a high voltage generator and inverter 614 that drives time-variant voltage and current under instructions from computing equipment 122, as driven by controller 110. The X-ray source 112 may contain one or more targets that are selected for emissions at different times under the control of computing equipment 122. Spectral content of X-ray emissions from source 112 may vary with an anode track and/or focal spot size. Spectral content is selected for use in obtaining measurement data by actuating filter 150 as a function of time by virtue of motion controls, which also govern the motion of patient positioning bed 128 and the detector array 114. The subject body 116 may, for example, be a patient, object, or sample for analysis.

Figure 7:
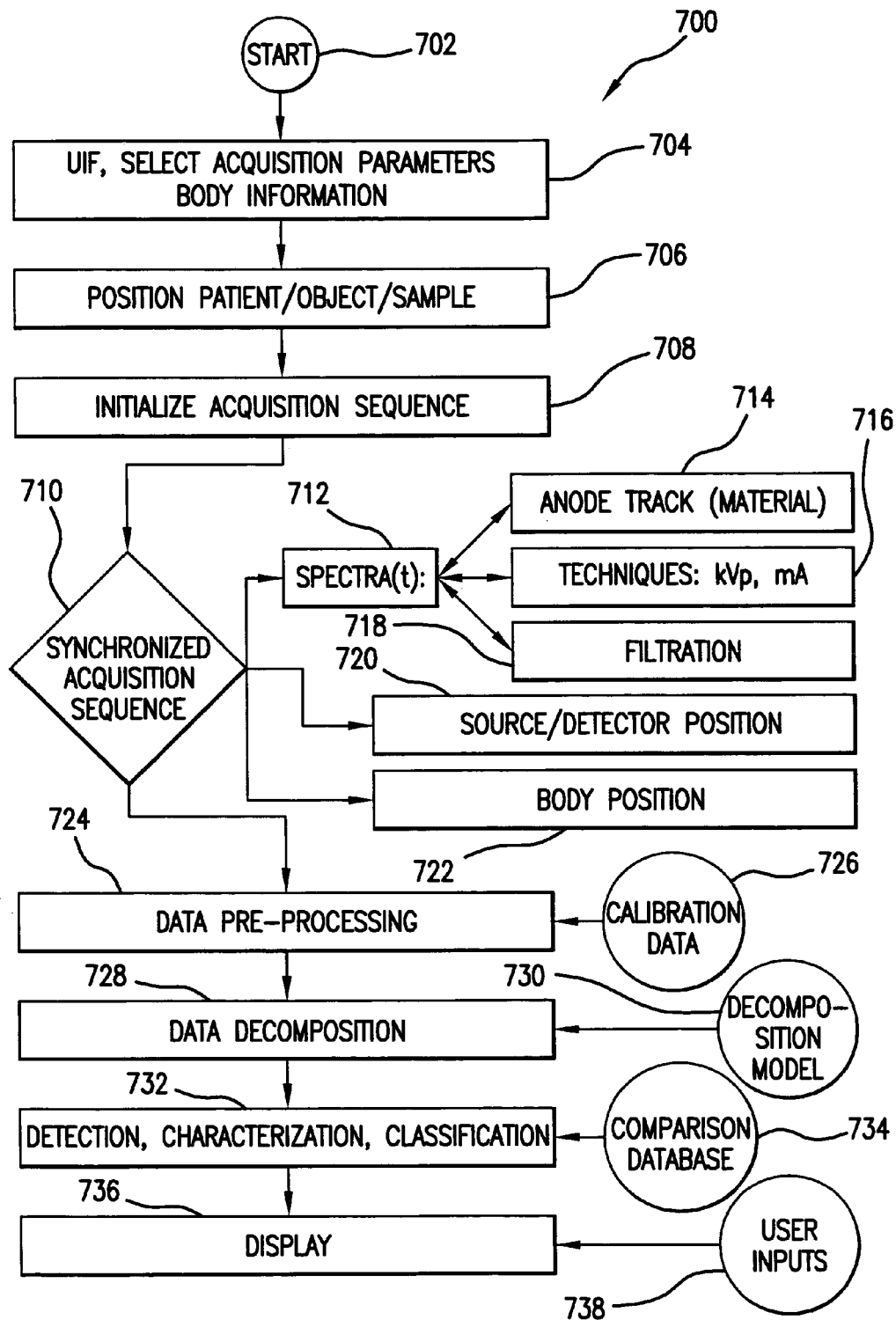
FIG. 7 is a flowchart illustrating one process of multi-spectral imaging.

FIG. 7 shows one example of process 700 including operator activities and program logic that is suitable for operation with the system 100 of FIG. 2 and/or FIG. 6. Data acquisition starts 702 with operator selection and input of data acquisition parameters, such as scan type and information about the body 116. By way of example, the operator may select from among a plurality of options described above, such as a CT scout/preview scan, projection imaging scan, or spiral CT scan. Measurements may be made on body 116 to identify axis 120 (shown in FIG. 2) and body landmarks. Step 706 entails operator positioning of the body 116 for scan presentation, and when the body 116 is ready the operator initializes the measurement acquisition sequence 708, whereupon computing equipment 122 commences the operator-selected scanning procedure.

As described above, the measurement acquisition sequence entails synchronized data acquisition 710, for example, by varying 712 spectra as a function of time by virtue of using different anode track material 714, voltage and/or current variation techniques 716, and/or filtering spectra 718, and/or changing x-ray focal spot geometry. Commensurate the varying 712 of spectral emissions, there is programmed positioning 720 of the source 112 and/or detector array 114. Further positioning 722 of body 116 may occur by actuation of bed 128. The raw data obtained by detector array 114 is submitted for data pre-processing 724, which may utilize calibration data 726 residing in database 606.

Subsequent to data read-out from the digital detector, the data are re-sorted, averaged and registered so that all multispectral samples of a given line integral are available for processing. Following this step, the standard CT correction steps may be applied as necessary to pre-condition the data so that they represent the best possible estimate of attenuation coefficients line-integrals. Such X-ray corrections include: air normalization, gain, lag, afterglow, spectral, and scatter corrections, log amplification, and beam hardening corrections (including both water-based and bone-based. Beam hardening will be largely reduced by the selection of relatively narrow-band spectra, as supported by our preliminary studies. These corrections are typically based on calibration data and include polynomial compensation of variable order depending on the exam parameters selected. Polynomial corrections, typically defined at a specific kVp and filtration, can be generalized into higher-order (surface) calibrations allowing for correction between specifically measured spectra.

Once calibrated, the measurement data is submitted for data decomposition processing 728, which may access a data decomposition model 730 from database 606 to produce image data appropriate to the selected scan type. The processed image data may be submitted to algorithms 732 for detection, characterization, and/or classification of image anomalies. By way of example, these algorithms may use multispectral X-ray data to identify a tumor by cancer type, or a gun or explosives in luggage. Algorithms 732 may be facilitated by comparison data and/or comparative models in comparison database 734. The comparison outcomes mat be used to modify the image data for presentation of identified image elements, for example, by highlighting the element according to a predetermined color scheme where the cancer, gun, or explosive is identified by a color, and the final data is provided to display 126 in step 736. The displayed output may include estimated likelihood of malignancy or severity classification. User inputs 738 may be used according to an interactive graphical user interface to adjust the image to clarify the identified elements, to enlarge selected image features for higher resolution display, or to reduce the size of the image.

Figure 8:
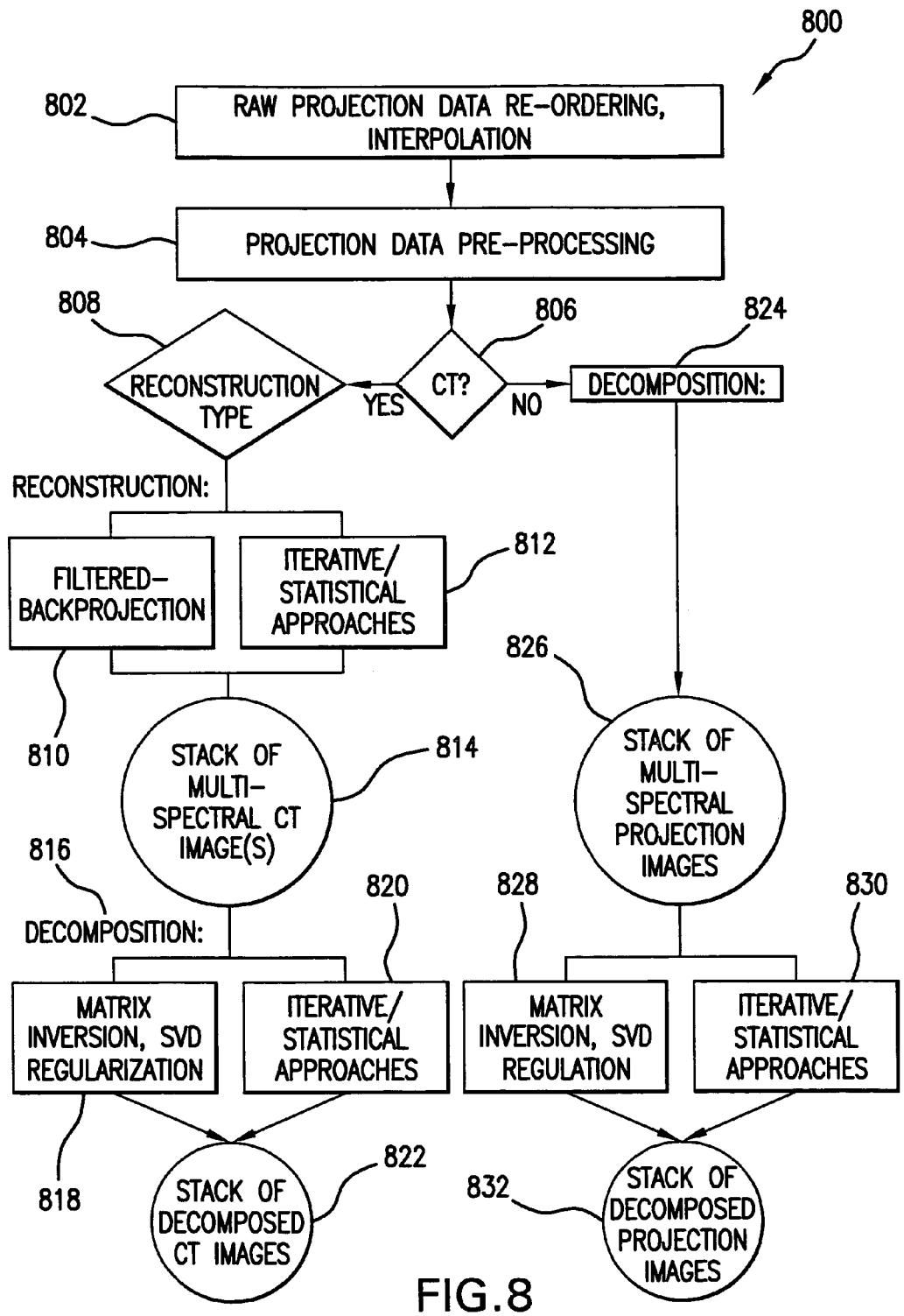
FIG. 8 is a flowchart illustrating additional detail with respect of FIG. 7.

FIG. 8 shows one process 800 that is suitable for processing data from a system (e.g., system 100, FIG. 2) to determine constituents of a body, and may be used in place of data pre-processing 724 and data decomposition 726 shown in FIG. 7. In step 802, the raw projection data captured by detector array 114 is re-ordered and may be interpolated to enhance image quality. The calculation results from step 802 are subjected to data pre-processing in step 804, for example, to calibrate the data for filter adsorption and other effect on paths 132. In step 806, the computing equipment assesses whether the selected scan type if a CT scan. If so, the computing equipment is programmed to select and apply a reconstruction type 808 based upon the operator-selected scan type. Options for use may include use of a filtered backprojection algorithm 810, iterative statistical approaches 81'2, or a combination of the two. The calculation results yield a stack of multispectral CT images 814. Decomposition 816 uses matrix inversion with SVD regularization 818 and/or iterative/statistical approaches 820 to provide a stack of decomposed multispectral tomographic images 822. This process may be modified, for example, where it is possible to interpose decomposition elements 816–822 before reconstruction elements 808–814.

Where computing equipment determines in step 806 that the scan type is other than a CT scan, processing proceeds with a different type of decomposition 824 commencing with a stack of multispectral projection images 826. Decomposition proceeds by matrix inversion with SVD regularization 828 and/or iterative/statistical approaches 830 to provide a stack of decomposed multispectral images 832.

Figure 9:
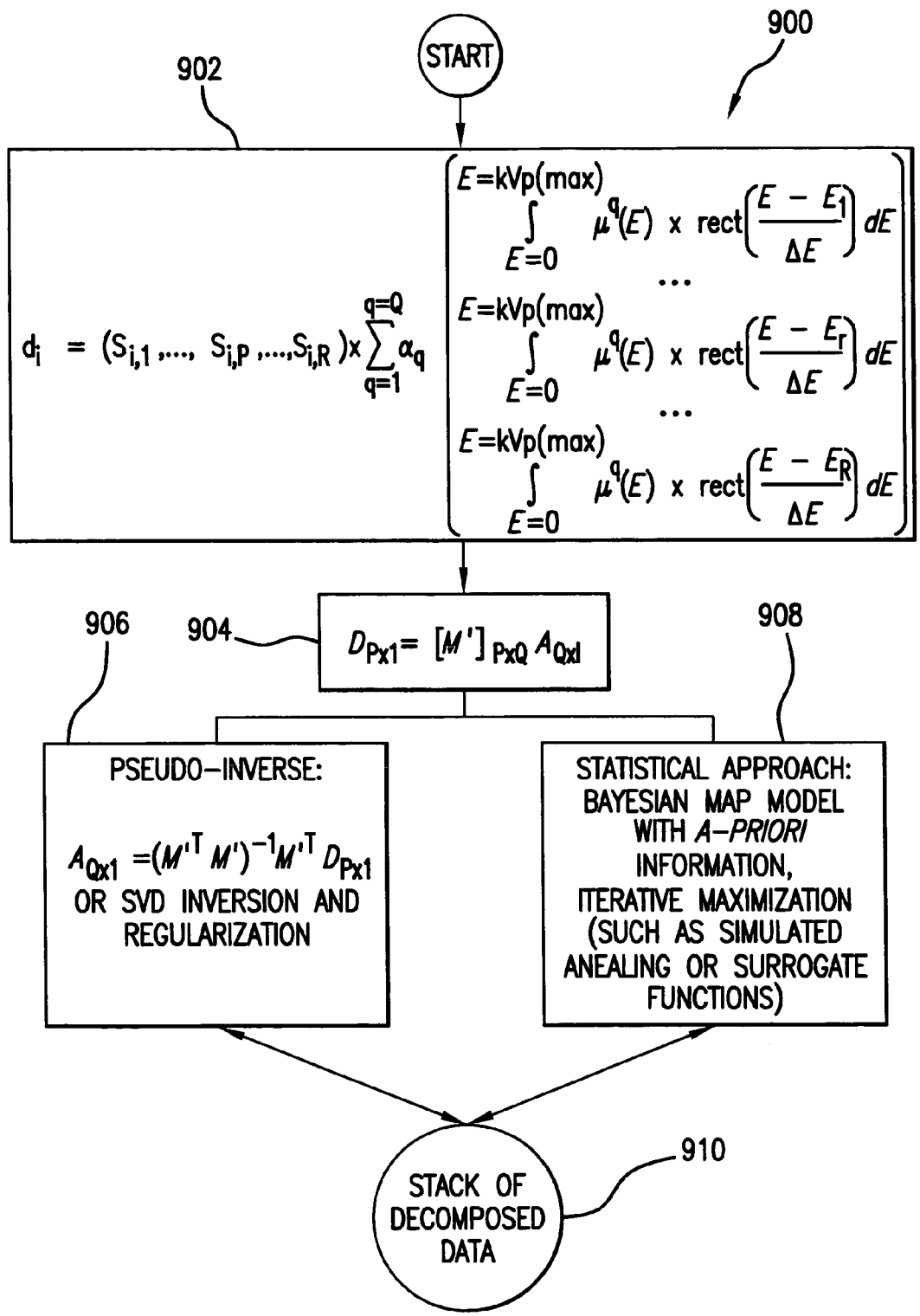
FIG. 9 is a flowchart illustrating a method of data decomposition.

FIG. 9 shows one method 900 of processing multispectral input data where a plurality of line-integral functions are generated in step 902, deconvolved onto a set of base functions in step 904, and statistically processed or decomposed in steps 906, 908. Generally, this statistical or decomposition processing uses an image formation model to characterize multispectral data in a way that assists diagnosis. The statistical processing may, for example, be done by a maximum likelihood estimator, or pseudo-inverse modeling or SVD inversion and regularization 906. Alternatively, Bayesian mapping 908 of the functions may occur onto a set of empirically or theoretically derived base functions that indicate a suspected diagnosis, for example, a normalized multispectral line-integral function observed from a cancer tumor. In this instance, the Bayesian mapping may identify curve characteristics that are unique to line-integral functions for a cancer of this type, for a firearm, or an explosive. Alternatively, an artificial learning algorithm, such as a neural network, may be trained to make this comparison and identification. For example, the neural network may be trained using full spectrum line-integral functions that have been divided into spectral bands. By way of example, line functions may be divided into healthy tissues and diseases according to a one of more types of disease. After training, the model may be used to produce a code that assigns a disease identifier to the line-integral functions. Image elements according to line-integral functions of interest may be image-enhanced, e.g., by color-coding or shading in a stack of decomposed data 910.

The discussion that follows provides detail concerning mathematical algorithms, structures and materials for use according to the processes described above.

Section A—Projection Imaging a.1—Multi-Spectral Imaging

Considering an object or patient under X-ray examination, let $I_0$ denote the illuminating X-ray intensity. $I_0$ is a function of the impinging energy spectrum E:

$$I_0 = I_0(E) \quad (1.1)$$

The spectrum $I_0$ is a function of the peak voltage applied across the X-ray tube (kVp), tube current (mA), the X-ray tube target material, and any inherent or added beam filtration. After going through the object along a path L a primary intensity I(E) exits and contributes to the detected signal. I(E) is related to $I_0(E)$ through Beer's law (Johns and Cunningham, 1983):

$$I(E) = I_0(E) \times \exp\left\{-\int_{path\,L} \mu(E, l)dl\right\} \quad (1.2)$$

where $\mu(E,l)$ is the total linear attenuation coefficient. The detected primary signal is then given by:

$$P = \int_{spectrum} \gamma(E) \times I(E) \times dE = \quad (1.3)$$

$$\int_{spectrum} \gamma(E) \times I_0(E) \times \exp\left\{-\int_{path\,L} \mu(E, l)dl\right\} dE$$

where $\gamma(E)$ represents the detector absorption efficiency at energy E. The total detected signal Q is:

$$Q = P + S + e, \quad (1.4)$$

where S is the detected scatter radiation and e is the electronic noise recorded. In the current practice of projection imaging, the detected signal is the result of an energy integration over a given time interval. Discrete numbers of photons at various energies and in various quantities are detected at various times during the integration time-interval, and the absorbed energy corresponding to each such event is summed to contribute to the total signal. In the resulting digital sample, it is not possible to separate each event, nor is it typically possible to know the total number of contributing events. Although materials exist that allow design of energy discrimination detectors, the electronics requirements and count-rate necessary for broad-band spectra currently render such approaches difficult for general X-ray imaging applications. Further, large detectors typically used in digital X-ray imaging accept a large amount of scattered radiation, which contributes to significant noise in the energy discrimination. Scatter-rejecting collimators are often used, but at a typical cost of a doubling in patient dose (Rudin and Bednarek, 1995). The proposed research addresses both of these limitations by describing a practical means to decompose a broad-band spectrum (such as given by practical X-ray sources) into specific spectra approximating narrow-band sources, and the use of narrow-beam geometries Practical emphasis will be on spectra shaping for optimal signal-to-noise ratios in dual- and triple-energy single-scan data acquisition.

Given means to generate M spectra $\Im_j$, j=1, . . . , M (discussed below), it is possible to decompose the attenuation coefficient on a set of N known continuous (as a function of the energy E) basis functions (N≦M):

$$\mu(E, l) = \sum_{i=1}^{i=N} a_i(l) \times \mu_i(E), \quad (1.5)$$

where the $\alpha_i(l)$ are the decomposition coefficients, dependent upon the coordinate $l$ along the path L from the X-ray source to the pixel under consideration. Note that these coefficients are representative of the material or tissue being imaged, and are independent of the spectrum indexed by j. By substitution into (1.3):

$$P_j = \int_{spectrum\ \Im_j} \gamma(E) \times I_0(E) \times \qquad (1.6)$$
$$\exp\left\{-\int_{path\ L} \sum_{i=1}^{i=N} a_i(l) \times \mu_i(E) dl\right\} dE,$$

subject to (s.t.) the decomposition normalization equation:

$$\sum_{i=1}^{N} a_i(l) = 1 \qquad (1.7)$$

By performing the integration under the discrete sum side, one obtains:

$$P_j = \int_{spectrum\ \Im} \gamma(E) \times I_0(E) \times \qquad (1.8)$$
$$\exp\left\{-\sum_{i=1}^{i=N} \mu_i(E) \int_{path\ L} a_i(l) dl\right\} dE,$$

s.t. (L may also represents the total path-length in equation (1.9):

$$\int_{path\ L} \sum_{i=1}^{i=N} a_i(l) dl = L. \qquad (1.9)$$

By defining N modified unknowns:

$$A_i = \int_{path\ L} a_i(l) dl, i = 1, \ldots, N, \qquad (1.10)$$

the following set of equations is obtained:

$$P_j = \int_{spectrum\ \Im_j} \gamma(E) \times I_0(E) \times \exp\left\{-\sum_{i=1}^{i=N} A_i \times \mu_i(E)\right\} dE, \qquad (1.11)$$
$$j = 1, \ldots, M$$

s.t.:

$$\sum_{i=1}^{i=N} A_i = L. \qquad (1.12)$$

Accordingly, N unknown decomposition coefficients ($A_i$) may be determined by M projection measurements obtained with the appropriate spectra (M>=N). These spectra may overlap, but ideally must be chosen such that the system of M equations (I.11) is non-singular, and invertible with regularization if necessary. In practical applications, the spectra are chosen to reduce the singularity of equations (1.11) in order to optimize the number of separate elements (basis functions) that may be recovered with limited noise amplification. A variant of this problem exists where an approximate single spectrum maybe considered decomposed onto narrow-band spectra. The corresponding spectra are generated and impinging upon the subject to be imaged in a time sequence. The detector records the patient-filtered spectra energies (in each of the detector cell of interest) during the integration time Δt. Accordingly, dividing the spectrum $\Im$ into M spectra, M measurements are acquired, and the primary signals are given by:

$$P_i = \gamma(E_i) \times N(E_i) \times E_i \times \exp\left\{-\int_{path\ L} \mu(E_i, l) dl\right\}, \qquad (1.13)$$
$$j = 1, \ldots M,$$

where $E_i$ represents the mean photon energy in the I-th energy interval of length $\Delta E_i$. As the input spectra are known (selected in a time sequence), so are the $N_i$=N($E_i$) quantities (within the X-ray Poisson statistics source of uncertainty). If the unknown line-integral $$\exp\left\{-\int_{path\ L} \mu(E_i, l) dl\right\} \qquad (1.14)$$

is decomposed as above onto R known basis functions (R≦M):

$$\mu_r(E_i), r=1, \ldots, R \qquad (1.15)$$

then:

$$\int_{path\ L} \mu(E_i, l) dl = \sum_{r=1}^{R} \alpha_r \times \mu_r(E), \quad (1.16)$$

where $\alpha_r$ are R unknown coefficients. Then equations (1.13) maybe rewritten in the form of a linear system of equations:

$$P'_i = \sum_{r=1}^{R} \alpha_r \times \mu_r(E_i), l = 1, \ldots, M, \quad (1.17)$$

where $$P'_i = -\mathrm{Log}\left(\frac{P_i}{\gamma(E_i) \times N(E_i) \times E_i}\right), i = 1, \ldots, M. \quad (1.18)$$

Under general conditions, the linear systems (1.17) can be solved by inversion. In principle, the measurement of M quantities, $M \geq R$, all corresponding to the same line-integral path through the object or patient, allows identification and quantitative characterization of the tissues or materials present along the line-integral path. In particular, X-ray linear attenuation coefficients are dependent upon the elemental atoms constituting the material, and the linear attenuation coefficients of composite materials, including soft tissues, are obtained in excellent approximation by a weighted combination of the elemental atomic constituents. In a practical implementation, it will be desirable to have characterized beforehand a set of R tissues most likely to be present in the anatomy under interrogation, including the normal anatomy and an extended range of pathologies.

In practice one may be interested in only the first R' basis functions, because the relative quantity of known materials, such as water, may not be of direct interest. In this situation techniques such as principal component analysis will find the M' basis functions that best explain the data. Further, additional constraints may be imposed that increase the number of measurements available per line integral, in either a continuous or a discrete model. For instance, the length of the line-integral may be determined in X-ray modalities where compression is applied, or from a simple segmentation of a reconstructed CT image. Indeed, in any CT image of the patient, there is a sharp CT number jump from air (about $-1000$) to soft tissues (about 0) or bone (up to 3000), adopting for this example a definition of CT numbers based on a 1000 multiplier. In such a case the constraint (1.12) becomes:

$$\sum_{i=1}^{i=R} A_i = L', \quad (1.19)$$

where L' denotes the length of the line integral under consideration in the object of interest, i.e., excluding the air-path. Additional constraints may also be imposed, such as lower and upper bound of the line integral, based on the an a-priori knowledge of the tissues or materials interrogated.

Each photon energy, or each average photon energy in a given spectral interval, may be weighted to improve signal-to-noise ratio. An excellent approximation to the ideal weight (in the lower energy photo-electric range) is given by a factor proportional to $1/E^3$ (Cahn et al, 1999).

In a practical implementation, each line-integral or X-ray path through the body will be sampled a total of T times, where T depends upon parameters such as the total number of detector rows, the scan speed, and the electronic operation of the detector (including electronic binning of the detector rows). It is thus recognized that T may be equal, smaller, or larger than the number of detector rows. For each of M spectra, $T_i$ measurements are acquired, where:

$$0 \leq T_i \leq T, i=1, \ldots M,$$

subject to:

$$T = T_1 + T_2 + \ldots + T_M.$$

For each X-ray path and each subset of $T_i$ measurements corresponding to a given spectrum, the $T_i$ measurements may be averaged to obtain M measurements as input to the processing (in which case the quantities $P_j$ in equation (1.6) are set to the average of the $T_i$ measurements:

$$P_i = \frac{1}{T_i} \sum_{k=1}^{k=T_i} t_k^i,$$

where $t_k^i$ represents the k-th measurements in the i-th set comprising $T_i$ measurement at the same spectrum). Alternatively, the measurements in each of the M subsets maybe combined or filtered by various methods to obtain the best estimate of the measurement for each of the M subsets. Methods that are applicable include digital signal processing and statistical methods.

Section A.2—Physics Motivation for Spectral Decomposition

Detailed attenuation properties of materials may be found in reference books, such as Johns and Cunningham, 1983; Barrett and Swindell, 1981; Boone, 2000. This section describes general principles that provide motivation and justification for spectral decomposition and material characterization based on energy response.

The total linear attenuation coefficient $\mu$ of a given material at diagnostic energies is given by:

$$\mu = \mu^{pe} + \mu^C + \mu^R, \quad (1.20)$$

where the superscripts represent respectively: pe for photoelectric absorption, C for Compton scattering, and R for Rayleigh (or coherent) scattering.

Materials properties may affect attenuation. The discussion bellow provides a summary of materials properties and their associated effects a) Density: The density of each element depends on its state and purity. Published values follow a trend of increasing density at higher Z (Boone, 2000). After removing gases from the calculations, the relationship between density and Z is approximately:

$$\rho \propto Z^{0.78} (r=0.76) \quad (1.21)$$

b) Energy: In-between edge effects, the photoelectric effect varies approximately as $1/E^3$. The Compton cross-sections tend to increase at low energies, and then plateau in the diagnostic range. The Raleigh cross-section decreases with increasing energy.

c) Atomic number: The linear attenuation coefficient exhibits a $Z^3$ dependency.

d) Compounds and mixtures: In the diagnostic range, chemical binding energies may be neglected in comparison to X-ray energies, and chemical compounds may be treated as mixtures. The mass attenuation coefficient of an N-element mixture is then approximated by:

$$\left(\frac{\mu}{\rho}\right) = \sum_{i=1}^{N} \left(\frac{\mu}{\rho}\right)_i W_i \quad (1.22)$$

where $(\mu/\rho)_i$ and $W_i$ are respectively the mass attenuation coefficient and the weight fraction of the I-th component.

This very brief summary of attenuation properties indicates that each element in the periodic table of elements has its own attenuation curve as a function of X-ray energy. The attenuation coefficients of the elements in the periodic table have been tabulated as a function of X-ray energies. Accordingly, sampling a given tissue with a number of energies greater than the number of constituents in principle suffices to identify all constituents along the path (line integral) being sampled. However, as the fundamental physics behind X-ray attenuation coefficients is dominated in specific energy ranges by photo-electric and Compton scattering effects, far from material K-edges most materials attenuation curves can be described as a function of energy by use of a few coefficients (Kelcz, 1977). Such a method of representing the attenuation coefficients as a function of energy by a small number of constants (which are independent of energy) was described early (Alvarez, 1976). Accordingly, acquisition of projection data at two narrow-band energy spectra in theory would suffice to analytically calculate the projection data for any keV. The optimal two acquisition energies, or in practice, mean spectra energies, will also depend on the amount of attenuation and detector response as a function of energy. When introducing a contrast medium with known K-edge properties, a third beam energy may provide additional information.

Accordingly, one system may use dual- and triple energy acquisition and data decomposition with near real-time spectral adaptation and automatic exposure control. By way of example, two spectral distributions may be obtained by different target materials, and three distributions may be selected when using a contrast medium. Selection of materials may be based upon the type of body 116, for example, to optimize imaging in terms of specific chest radiography imaging tasks.

Section A.3—Input Beam Spectral Decomposition

A means of dynamically changing the beam filter is illustrated in FIG. 2 by use of a rotating filter 150. Considering a filter wheel with various sectors 154 (only a few are shown), each of a given material, the filter wheel rotation is synchronized with the kVp selection and the timing of the data acquisition. Several filter wheel sectors may be designed to contain materials more practically available in liquid form, such as iodine. For illustration Table 1 lists a number of selected elements and associated k-edges (in keV), that are relevant to X-ray filtration.

Use of a rotating filter wheel 150 is also possible with several filter material positions or sectors 154 per kVp setting, e.g., to sample the patient being imaged at a given kVp and with various spectra. Additionally, the number of wheel sectors 154 may be different from the number of selected spectra, as each filter material may also be used with a variety of kVp and mA (technique) settings. Similarly, the number of acquired digital samples for a given spectrum may be spectrum-dependent for signal-to-noise and basis function separation (independence) considerations. Further, the filter wheel design may be optimized by providing for two independent filter wheels, possibly made of different materials, and each rotating in opposite direction. In such an arrangement, one of the wheels may rotate relatively slowly to introduce variations in (for example) the amount of aluminum filtration, while the fast rotating wheel may include k-edge filters as appropriate for the proposed imaging task.

The filter materials and kVp waveforms may be optimized in a number of ways, resulting in a large number of possible spectra and imaging configurations. Similarly, with a specific tube design (such a dual target anode configuration, as often used in mammography (Molybdenum/Rhodium)), it is possible to electronically steer the tube electron-beam from one track to the next with a response time of a few microseconds. The corresponding beam displacement on the detector may be tracked by appropriate selection of the active primary-imaging detector rows/columns. It should be noted that modern high-frequency X-ray generators and tubes allow peak tube kilo-voltage (kVp) to be switched (for example, from a low to a high setting) in the order of a few micro-seconds (20 to 100 micro-seconds depending on design) (Sobol, 2002).

Figure 10:
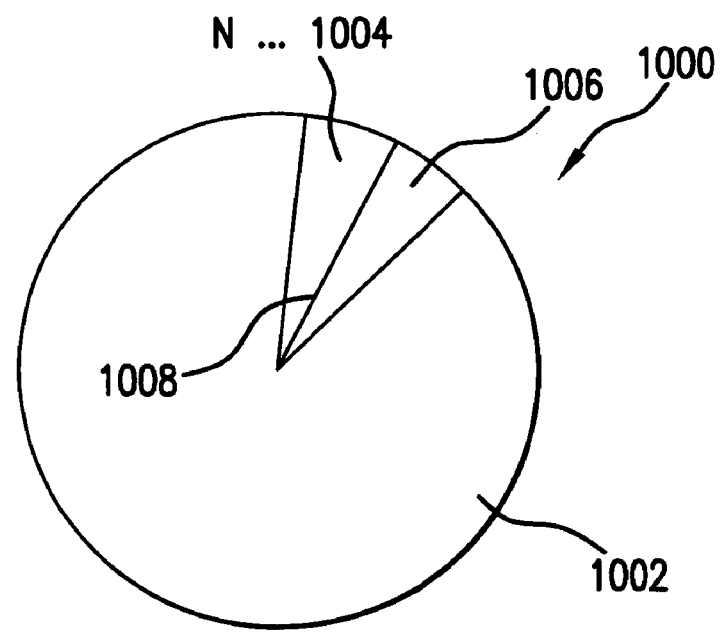
FIG. 10 is a top plan view of an x-ray filter wheel assembly.
Figure 11:
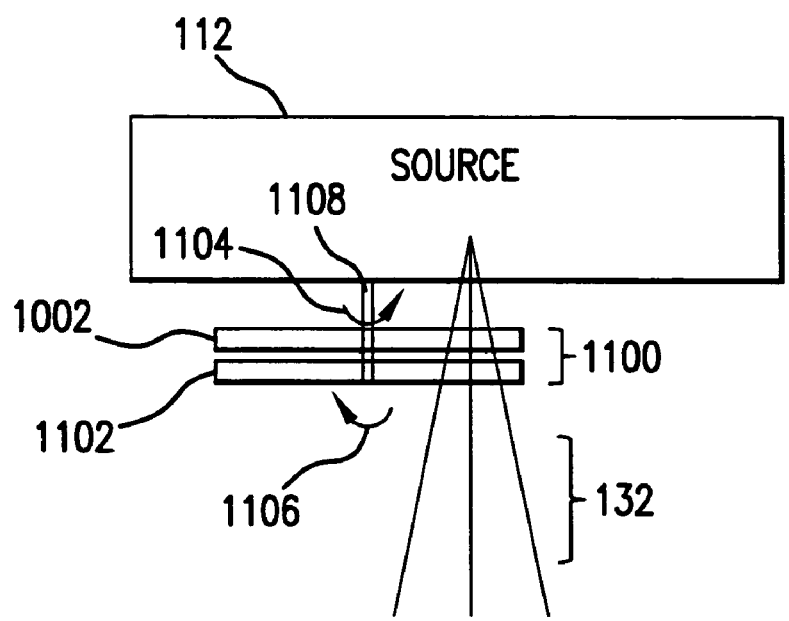
FIG. 11 shows a dual filter wheel assembly that may be selectively adjusted for combined filtering operation.

FIG. 10 shows a top plan view of one design for a dynamic subfiltration assembly 1000 that may be used as filter 154 (shown in FIG. 2). A filter wheel 1002 is made of a plurality of sectors 1004, 1006 (there may be a total of S sectors), each sector having a different material composition or a different thickness of the same material. Depending on the X-ray tube operation mode, whether pulsed or continuous, it may be advantageous to have overlapping sectors at boundary 1008 to ensure continuous transitions in filtration. FIG. 11 Illustrates a dual wheel filter assembly 1100, which provides a filter assembly design having increased flexibility. The filter wheel 1002 is mounted in selective rotational alignment with a second filter wheel 1102 for dual filtration purposes. The two filter wheels 1002, 1102 may be rotated in opposite directions and at different angular velocities 1104, 1106 by drive mechanism 1108. One of the wheels 1002, 1102, may be designed to vary the base filtration, such as by using aluminum, copper, etc., as a function of the temporally varying kVp from source 112, while the second wheel may contain sectors 1104, 1106, each or a subset of the sectors containing k-edge filters as is appropriate for the intended application.

TABLE 1

A few elements from the periodic table, with associated symbols and k-edges (in keV).

| Aluminum | Barium | Cesium | Copper | Gadolinium | Iodine | Lead | Samarium | Tin | Tungsten | Zinc |
|---|---|---|---|---|---|---|---|---|---|---|
| Al | Ba | Cs | Cu | Gd | I | Pb | Sm | Sn | W | Zn |
| 1.56 | 37.41 | 35.60 | 8.98 | 50.23 | 33.16 | 88.00 | 46.85 | 29.19 | 69.51 | 9.66 |

Within source 112, tube current (mA) variations also may be induced in a few milliseconds. As tube current affects only the quantity of X-rays at a given energy, but not the energy distribution, mA variations contribute linearly to the detected signal and may therefore be averaged or otherwise compensated for very accurately.

Section A.4—Configurations for Line-Integral Multiple Samplings

Figures 12A, 12B:
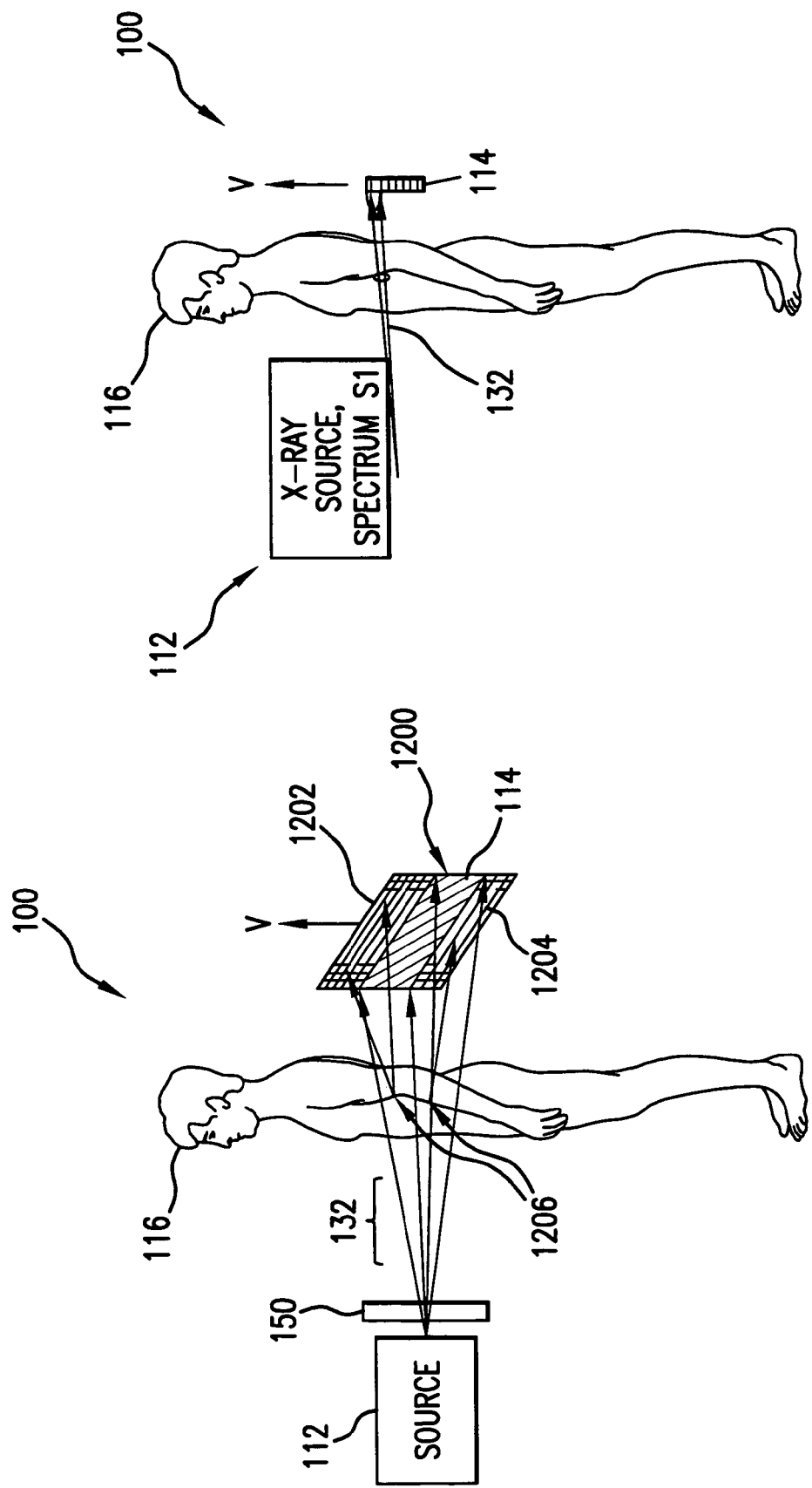
FIG. 12A shows a projection imaging system adapted for use in an upright patient imaging situation.
FIG. 12B shows a first scan at a first emission spectra in an upright imaging system.

Several alternative configurations are available for use in system 100 to provide multi-spectral sampling of the same line integral in an examination time that precludes motion artifacts. By way of example, up-right scanning may be beneficial to chest imaging, as illustrated in FIG. 12A, where source 112 projects primary paths 132 towards detector array 114, which has a primary detector array section 1200 directly in line with linear paths 132 and side sections 1202, 1204, aligned to receive scatters 1206 outside the projected primary beam. The detector array 144 may move at a tangential velocity V, in processing synchronicity with the spectra generation, data acquisition, and scanning of the image chain with respect to the body 116 (such as with the patient lying on a examination table). Scatter data may be used to enhance compositional analysis of the primary image obtained from the primary grid section 1200. The scanning procedure may be completed by any number of scan excursions to acquire $T_1$ measurements for the spectrum $S_1$. Thereafter, the source 112 may be reconfigured to emit a different spectrum, $S_2$ for a substantially exact replication of the same scanning procedure to acquire $T_2$ measurements for spectrum $S_2$. Alternatively, the spectra $S_1$, $S_2$ may be emitted simultaneously or in rapid succession during a single scan excursion to obtain $T_1, T_2, \ldots, T_M$ measurements for each of spectra $S_1, S_2 \ldots S_M$ during a single scan excursion.

Figure 12D:
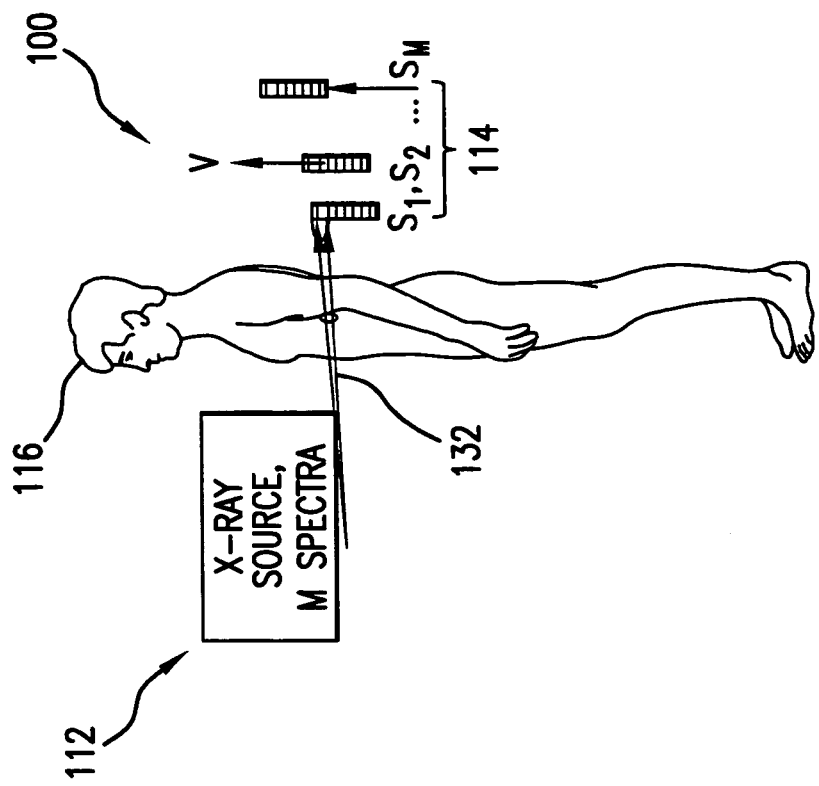
FIG. 12C shows the use of a multiplicity of source emission spectra in a single scan.
Figure 12C:
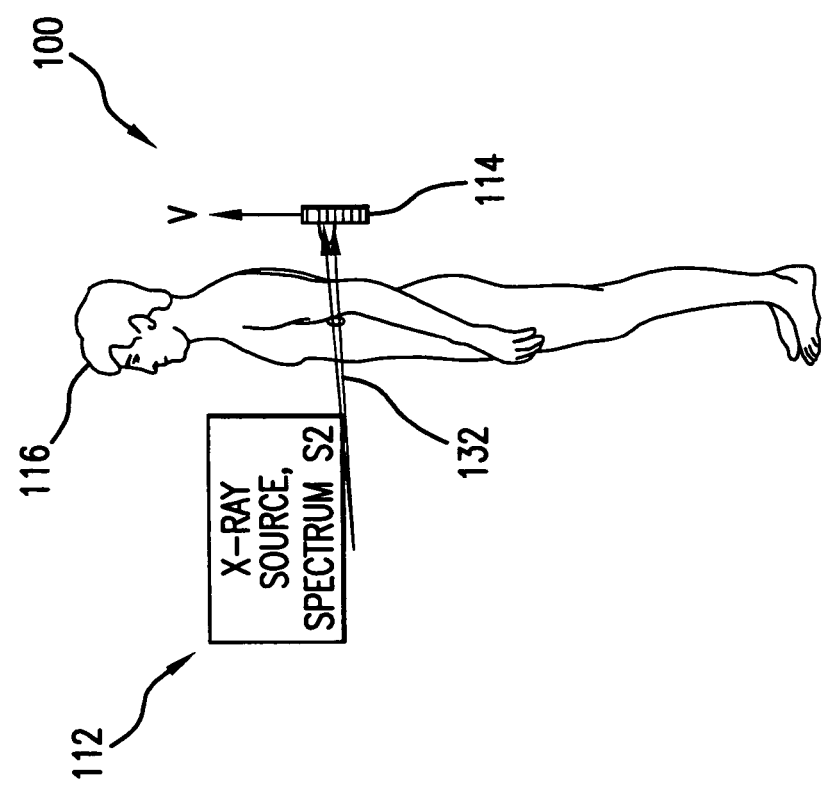

By way of example, FIGS. 12B–12D. In FIG. 12B, show use of a narrow-aperture, full-frame sampling detector 114 that is scanned behind the body 116 with a first spectrum S1 selected to acquire $T_1$ measurements for spectra S1. In FIG. 12C, the scan continues with a second spectra S2 selected to acquire $T_2$ measurements for spectra S2. FIG. 12D shows that a variety of M different spectra may be selected in turn in the time necessary for the detector to advance by a distance equal to its width using, for example, M spectra where the spectra may vary in synchrony with kVp, filter wheel selections, and/or mA.

Figure 13:
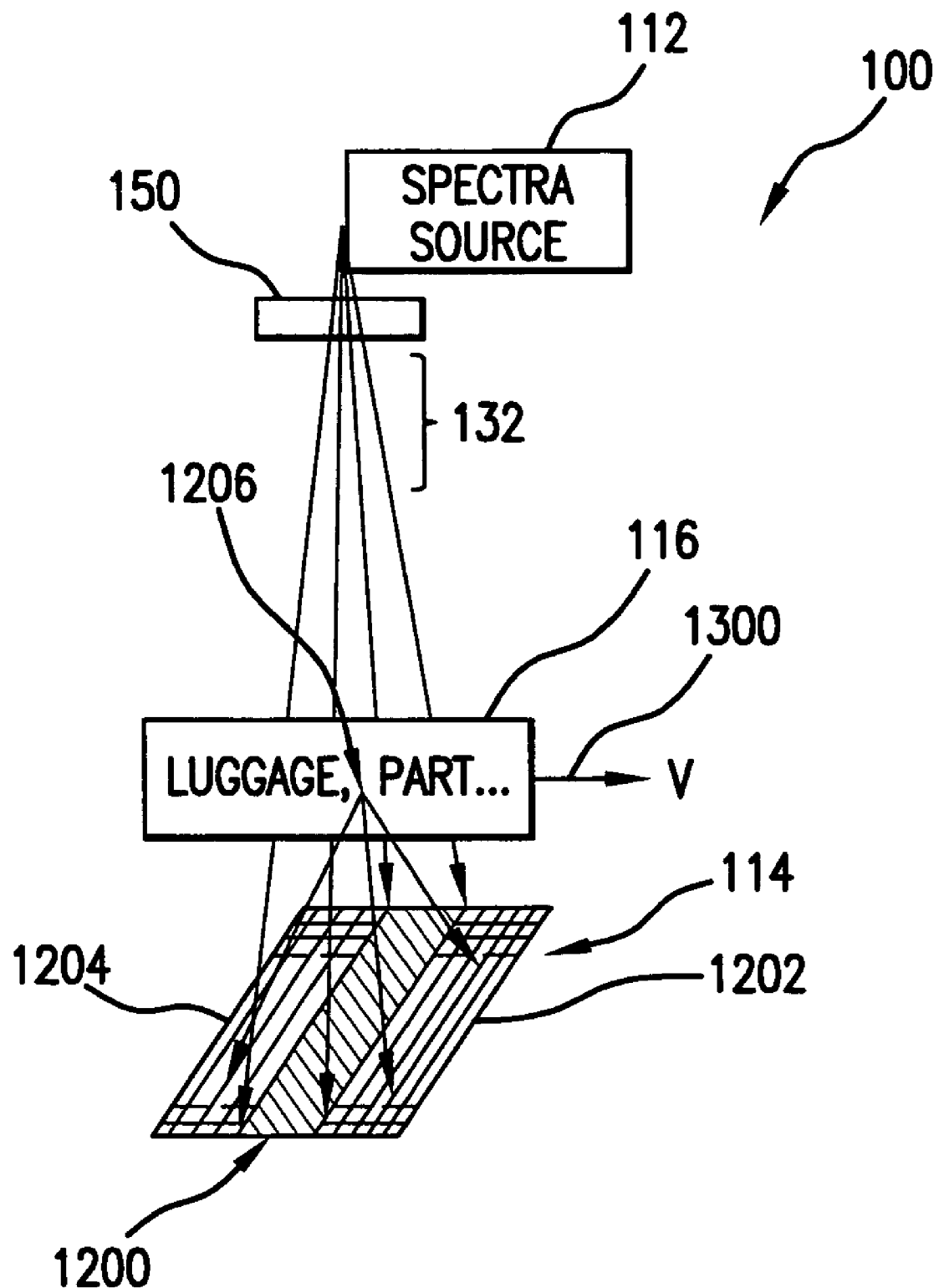
FIG. 13 shows an imaging system using luggage on a conveyor scanning assembly.

FIG. 13 shows that system 100 may be adapted to provide similar scanning processes for other objects, such as where the body 116 is luggage or a mechanical part and the tangential velocity V is here imparted by a conveyor belt system 1300.

Section A.5—Cyclical and Pseudo-cyclical Spectra Selection

To continuously image a volume of interest, the spectra may be repeated in a cycle. The cycle length depends on design and examination selections. In particular, the maximum number of spectra that can be separately detected on a particular slice of the patient under interrogation is given by the number of detector rows/columns that are fully included in the primary beam projection at any one-time, and the beam spectrum generation capabilities. A given spectra retained as input to the multi-spectral decomposition algorithms, as described below, may result from an average of particular time-varying parameters, such as the kVp. For example, the kVp may be continuously varied with time, so that the read-out data of an average of a given number of columns samples would correspond to a known average spectrum. Trade-offs between the numbers of distinct spectra, versus the number of samples available, can then be optimized for each application to reflect constraints of noise and dose limitation.

Further, access to the full-frame digital data allows dynamic and adaptive selection of the techniques (such as kVp and mA), to reflect varying attenuation condition encountered along the body being scanned. Such an "automatic exposure control" approach could be used to adaptively change the range of imaging parameters that will be used to image a particular slice of the patient. As a result, the kVp, mA, filtration, and anode-track selection waveforms would become pseudo-cyclical.

Section A.6—Data Preprocessing and Decomposition

X-ray projection standard data pre-processing methods include, for example, offsets and gain corrections, together with bad-pixel interpolation.

By relying on the selection of narrow, essentially non-overlapping spectra, there may be provided an estimate of the projection data—one given in each of a number P of energy intervals. Detector energy discrimination and photon counting may also be used for this purpose. Although the intervals are not necessarily of equal width, for simplicity the discussion below will assume so. A given line integral measurement then represents an average (possibly a weighted average as discussed above) of the detected events over such discrete intervals. The linear attenuation coefficients of Q basis function materials are known as a function of energy over the P spectra of interest, a given average attenuation coefficient being approximately obtained by integrating as follows:

$$M_i^j = \int_{E=0}^{E=kVp(\max)} \mu^j(E) \times rect\left(\frac{E - E_i}{\Delta E}\right) \times dE, \quad (1.23)$$

$$j = 1, \ldots, Q; i = 1, \ldots, P,$$

where rect( ) represents the usual function:

$$rect(x)=1; \; -\tfrac{1}{2} \leq x \leq \tfrac{1}{2} \quad (1.24)$$

$$rect(x)=0 \text{ otherwise.} \quad (1.25)$$

Accordingly, representing the Q basis functions (as measured at P energy intervals) in matrix form, the problem (in a linear approximation corresponding to equations (1.13) to (1.18)) is posed as:

$$[M]_{P \times Q} \times A_{Q \times 1} = D_{P \times 1}, \quad (1.26)$$

where M represents a matrix with P rows and Q columns, A is the vector of unknown decomposition coefficients (Q×1) (c.f. equation (1.17)), and D (P×1) represents the data (for one line integral through the patient in the X-ray projection) as a function of the P energy intervals.

The decomposition is now formulated as an inverse problem. Formally, the solution to equation (1.26) is given by the pseudo-inverse (where $M^T$ represents the transpose of matrix M):

$$M^T M A = M^T D \quad (1.27)$$

and if the resulting matrix is non-singular:

$$A = (M^T M)^{-1} M^T D \quad (1.28)$$

This solution to the normal set of equations (1.27) provides the least squares solution (Strang, 1988). It is also well known that the singular value decomposition (SVD) of a matrix may be utilized to provide a regularized solution to the original problem. SVD is a powerful approach to problems posed with matrices that are singular or near singular (Press, 1999). Regularization is a known tool in alleviating issues associated with noise and inconsistencies in the projection data (Stark, 1987; Lagendijk, 1991).

Recently, iterative and statistics methods have been the focus of a number of investigators (for a recent review, see Fessler, 2000). The availability of more powerful computers and the increased use of computed tomography (CT), together with related dose concerns, have combined to provide motivation to the search for more noise-efficient algorithms. Iterative algorithms allow inclusion of a-priori information in the image formation model. This information can include aspects of beam spectral contents, constraints on the observed data (such as positivity in CT), and noise considerations. In projection X-ray imaging, the noise is often modeled as Poisson. Simple application of the central limit theorem indicates that the summed data (for each selected spectrum) be well modeled as Gaussian. Other information that may be included relates to the geometry of the data acquisition and to the specifications of the imaging detector. Statistical data processing approaches have been applied to poly-energetic X-ray tomography (Elbakri and Fessler, 2002), as well as to dual-energy CT image reconstruction (Fessler et al., 2002).

Efficient implementation of these algorithms may facilitate signal-to-noise performance improvements and a decomposition time commensurate with clinical needs. Image decomposition noise is decreased by reducing both spectra overlap and spectra width. Decreased scatter-to-primary ratios will also contribute favorably to the image decomposition.

Section A.7—Multi-Spectral Scanning-Beam—Narrow Beam Advantages

Current slot-scanning systems rely on the time-and-delay-integration (TDI) mode available on specific charge-coupled-device (CCD) designs (Holst, 1998). CCD refers to a semiconductor architecture in which a charge is read out of storage areas ("wells"). In TDI mode, the charges are "rolled-over" from one CCD charge well to the next as a function of driving voltages ("phases;" this roll-over process is also illustratively referred to as a "bucket brigade"). Accordingly, the read-out occurs after integration of the signal over as many wells as there are CCD rows. This design allows integration of the signal while maintaining spatial resolution in scanning applications with a moving detector (if the detector velocity is exactly synchronized to the charge transfer internal to the CCD). Digital projection data corresponding to a fixed point in space are not available until the point's shadow has crossed over the entire width of the CCD chip (Besson et al., 2002).

In comparison, full frame digital sampling is one way to make multi-spectral imaging feasible. In this design, the entire detector array is sampled digitally at each sample interval. In scanning applications, this sample time interval corresponds to the time necessary for one detector row to move across the projection shadow of a fixed point in space. Accordingly, for each fixed projection bin (corresponding to the width of a detector row), as many digital samples are available as there are detector rows. Fast, low-noise CMOS technology (in one implementation, with back-panel read-out) is a key enabler for this imaging mode. Access to the full-frame sampling allows synchronized tuning of the X-ray spectra and sampling of all line-integrals through the patient at a multiplicity of energies. Additional unique advantages of the full-frame sampling narrow-beam scanning technology are now described.

In TDI scanning applications, automatic exposure control (AEC) is simply not feasible, as the data are available only with a delay corresponding to the integration time across the detector. In comparison, direct access to the digital datum for each sample allows additional tuning of the techniques as a function of the anatomy being scanned. This completely eliminates the need for a pre-scan or pre-exposure, and enables improved image quality at lower dose. The system may also scan in either direction, which is a feature not available with current TDI implementations.

As is well-known from CT applications, air-calibration is essential to the accurate estimation of the line-integral data, and to all ensuing physics corrections. With fast full-frame sampling the detector never saturates. This eliminates the well-capacity limitation associated with CCD designs. All TDI devices currently in medical imaging use operate in saturation mode in the air-field, which prevents an accurate air calibration. The resulting dynamic range is also well in excess of that practical with a-Si or a-Se large flat-panel detector arrays. The full-frame sampling design advantage will bring X-ray projection imaging significantly closer to quantitative imaging. The CMOS architecture according to the instrumentalities discussed below enables low-electronic noise and very large dynamic range, such that the system operates in quantum-limited mode under most relevant imaging conditions.

Narrow-beam approaches intrinsically benefit from a factor 2 decrease in dose (or increased DQE) by eliminating the scatter-rejection grid (Bucky grid)—assuming a given detector technology (Barnes et al., 1976; Rudin et al., 1995). In practice, however, a number of commercially available slot-scanning systems do not fully realize this dose advantage. To eliminate vibration image artifacts (induced by the relative motion of the beam with respect to the detector) in TDI designs the beam is over-collimated with respect to the active detector area. Over-collimation is also the main reason why early MDCT systems delivered 50% or more patient dose than single-slice systems (McCollough et al., 1999). In comparison in narrow-beam scanning application, penumbra imaging in conjunction with full-frame digital sampling will allow beam-tracking. Such an approach has already been implemented in MDCT to reduce dose and artifacts (Toth et al., 2000). By finely sampling the penumbra, the beam-position with respect to the detector can be determined from the (non-saturated) projection data. This tracking approach enables lower dose imaging by fully utilizing the penumbra photons. It will also ultimately lead to electronically controlled tube rotation around its focal point by allowing the beam to track the relative beam-to-detector motion via electronic feed-back. With such a design, the cumbersome mechanical link between the tube and detector is advantageously eliminated. A beam width on the order of 10 mm with a detector array that is about 25-mm wide may be used to derive these advantages. It also becomes possible to electronically steer the tube electron beam from one X-ray tube anode target track to another, in a time commensurate with the sampling interval (certain CT scanners use such "flying-spot" tubes to double the sampling rate per projection). With such an implementation the beam projection onto the detector would shift by a few millimeters when the electron beam switches from one target track to the next. Full frame digital sampling will enable beam profile tracking and digital signal integration without adverse image quality consequences From the beam and active detector widths listed above (10 and 25-mm respectively), it is clear that a full-frame sampling architecture provides a means to directly sample the scatter field. Scattered radiation differential cross-sections are known to vary relatively slowly in angle (Barrett and Swindle, 1983; Johns et al., 1983). Due to the detector low noise properties, a scattered intensity down to a fraction of the primary could be measured. A simple low-order polynomial correction (implemented on a column or channel basis) is likely to be effective in improving the scatter-to-primary ratio of the measured projections; generalizations are possible.

Full frame measurement of the primary and scatter fields allow dynamic primary X-ray beam width control to achieve a constant scatter-to-primary ratio. Such a constant scatter-to-primary ratio may be achieved by dynamically and adaptively adjusting the collimator width.

Scanning approaches that rely on the TDI integration process require very precise detector alignment in the scanning direction in addition to accuracy and invariance of the scanning velocity to match the electronic well-transfer rate. According to the present instrumentalities, availability of full-frame sampling allows re-sampling of the acquired data via interpolation methods on any pre-determined grid based on sample location information. Such information may be given in the scan direction by use of a servo-motor and linear-encoder based feedback loop. Alignment information may be determined from calibrated markers located outside of the patient imaging field or directly from the data (Tirumalai et al, 2000). Accordingly, variable beam-velocity imaging may be practiced.

Multi-spectral co-registered imaging offers potential to image various features of the lungs, including the vasculature, the bronchial airways, mediastinum, and bone structures. The system may allow recording of the EKG signal and subsequent data processing to record various phases of the heart and perform retrospective (or prospective) gating. Additional imaging modes are made possible by bi-directional scan imaging: region-of-interest (ROI) diagnostic imaging; low-dose stationary imaging to detect presence of contrast medium followed by computer-triggered scanning.

Another advantage of multispectral imaging is to tune the subspectra in use to detect specialized contrast media for medical imaging. Certain new media are targeted to specific molecules and/or allow delivery of drugs to specific sites. Multi-spectral approaches are well-suited to the X-ray imaging of new contrast agent with specific energy-attenuation characteristics.

Section A8—Detector Types and Noise Reduction

Any conventional detector for use in X-ray imaging may be used for the purposes of detector array 114 in system 100 including, for example, CCD's and flat panel detectors. The results obtainable from system 100 may be enhanced by the use of photon-counting and energy-discriminative detectors, for example, to allow linearization of the decomposition problem. In that regard, direct conversion materials such as Cadmium-Zinc-Telluride (CZT) and Mercuric Iodide ($HgI_2$) offer useful properties, such as the potential for very high X-ray efficiency and energy discrimination. CZT is notoriously difficult to obtain in the desired purity, particularly for large detector areas due to ingot size limitations, and applications to imaging lead to significant non-uniformity and noise issues (Ford et al., 2000). $HgI_2$ at its current stage of development suffers from lag (Zantai et al., 2002; Gilboa et al., 2002) and response non-uniformity (large broadening of the histogram distribution under constant exposure, likely due to grain size considerations (Street et al., 2001; Gilboa et al., 2002; Iwanczyk et al., 2001). Even so, these are useful detector materials, and the noted material deficiencies may be compensated by calibration or spectral and energy constraints imposed on the filtered emission spectrum.

Energy discrimination and photon counting have been long heralded. Studies shown below indicate that system 100 may operate, for example, in quantum-limited mode under a wide variety of lung imaging conditions. Accordingly, photon-counting by itself does not necessarily bring about a large signal-to-noise (SNR) advantage; however, when used in conjunction with multispectral energy discrimination, photon-counting may provide improved scatter characterization and corrections. Even so, energy discrimination does not resolve coherent scattering because as no photon energy is lost in such an interaction. Therefore, spectral beam shaping and full-frame sampling may reduce detector noise when used in combination with quantum limitations and energy discrimination.

CT reconstruction algorithms have evolved continuously since early theory was developed and first practical implementation efforts were successful. The advent of MDCT has further fueled interest into this topic. Recently, renewed efforts have been devoted to iterative algorithms with the goal of improving noise properties and fully leveraging the available projection data information. Image decomposition algorithms may leverage these continuing advances to reduce decomposition noise.

The following examples teach by way of example and provide different modeling techniques that may be applied according to the principles described herein.

EXAMPLE 1

Modeling of Beam Spectra Generation and Detection

It is possible to mathematically model X-ray spectra, filtration, phantom attenuation, and detector absorption, for example, including the spectral attenuation equation, as shown by equation (1.3). As will be seen below, this model confirms a physical basis for the feasibility of full-frame sampling and narrow-beam X-ray scanning, for example in lung imaging as well as for other applications described above. The output of this model may be used to provide test input sets for use in further modeling. In particular, key aspects of signal, noise, dose, and spectra separation have been modeled and confirmed by empirical studies.

In practical X-ray beam imaging, four parameters are available to shape the X-ray spectrum. These are the X-ray target material, the amount and type of filtration used, the kVp applied, and the tube current that is selected. Calculations to provide an X-ray spectra may, for example, be performed using the TASMIP model (Boone et al., 1997; Boone, 2000) for a Tungsten tube, where linear attenuation coefficients are available from various sources, such as the XCOM government database accessible from the National Institute of Standards (NIST) at http://physics.nist.gov/PhysRefData/Xcom/Text/XCOM.html.

Input parameters (in italics in this section's Tables) to the model included the source-to-image-detector distance (SID; 140 cm), X-ray beam-width, filtration materials, effective mAs at each retained kVp, the phantom to be imaged, scan length (430 mm), and various detector parameters including pixel size (127 microns), detection efficiency, electronic noise (400 e), and read-out time (4 ms).

Output parameters included entrance air exposure, detector entrance dose (behind phantom), absorbed spectra, total number of detector rows in the primary beam (given beam width and pixel size), number of X-ray photons and corresponding electronic signal per each digital sample, effective exposure and total scan time, SNRs. The model was built under the simplifying assumption of a constant tube current (mA); the mA was calculated (model output) as necessary to achieve the input mAs at each kVp. The number of samples at each kVp (equivalently, the number of detector rows) was calculated as part of the same algorithm. That is, given a number of detector rows in the primary beam, the program calculated the necessary tube current and distribution of rows (samples) for each kVp necessary to reach the input mAs.

The standard AAPM chest phantom was retained for all results reported herein. In terms of attenuation, the AAPM phantom consists of 101.6-mm of acrylic and a total of 3-mm of Aluminum (AAPM, 1998). Although the AAPM chest phantom attenuation data were used, the entrance air doses (technically, kerma values) were scaled to the entrance distance corresponding to the use of the NEXT Adult Chest Phantom thickness (230-mm) (Spelic et al., 2002). This allowed comparison to the extensive survey data reported by Spelic et al. Most computer experiments were run to simulate a detector entrance exposure in the range 4 to 8 μGy. Film-screen system entrance exposures are typically in the range of 4 μGy behind the Bucky grid (Aufrichtig et al., 2000). Due to the absence of a grid in the model design for corresponding tube techniques and filtration, a 4 μGy exposure to the detector would correspond to an 8 μGy entrance exposure on the model system (Rudin et al., 1995). This range of values were applied to experimentally set mAs input parameters. All graph fluences in this section are reported in photons per $mm^2$ at the detector surface. A simplified CsI absorption model using 6 attenuation values was used to calculate the electronic signal in air; all other results were obtained with attenuation curves and spectral data sampled every 2-keV. The following sub-sections report on the simulation results.

Single Spectrum for Conventional Digital Chest Imaging

A simulation was performed at techniques similar to conventional chest radiography. Table 2 provides the model input and output parameters.

Table 3 provides the corresponding beam characterization data including additional model input parameters and spectra characteristics:

TABLE 3

| | Techniques: kVp 120 mAs 1.6 |
|---|---|
| Air Exposure | |
| SID-scaled mAs | 0.8163265 |
| Fluence per mm**2 | 2146418 |
| μ-Gy (scaled to 117-cm) | 82.4 (118) |
| Samples per kVp: | 79 |
| Photons per sample: | 451 |
| CsI quantum efficiency: | 0.4 |
| Mean energy (keV): | 55.9 |
| Air Signal(electrons): | 396612 |
| HVL | 5.2 |
| Exposure behind AAPM phantom | |
| Fluence per mm**2 | 141112 |
| Entrance dose (micro-Gy) | 4.6 |
| Photons per sample: | 30 |
| Mean energy (keV): | 65.2 |
| CsI absorbed spectrum and signal | |
| Electronic noise (electrons): | 400 |
| Fluence per mm**2 | 115856 |
| Photons per sample: | 24 |
| Mean energy (keV): | 61.4 |
| Electron per X-ray: | 1002 |
| Integrated SNR: | 43.1 |
| Quantum SNR (no e-noise): | 43.2 |
| Phantom signal (electrons): | 24382 |
| Percent CsI absorption: | 82.0 |

Figure 14A:
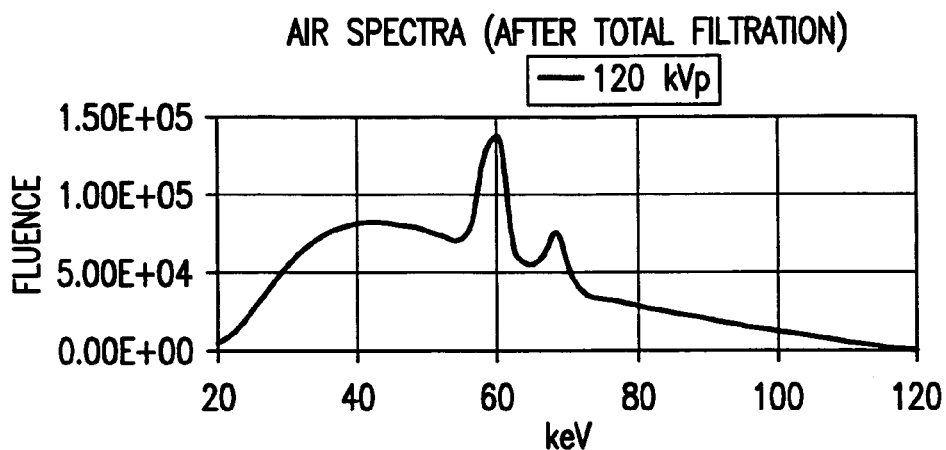
FIG. 14A shows model calculation results for a single X-ray spectrum in air after total filtration.
Figure 14B:
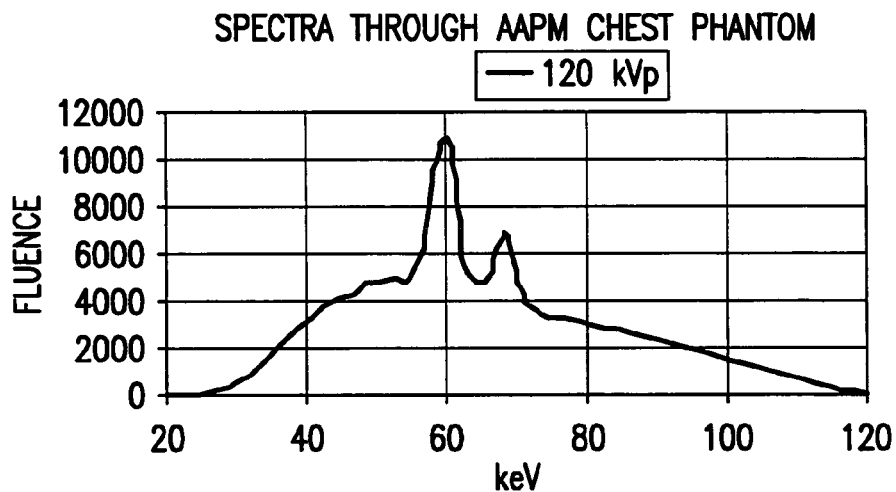
FIG. 14B shows X-ray spectrum after passage through a standard phantom target.
Figure 14C:
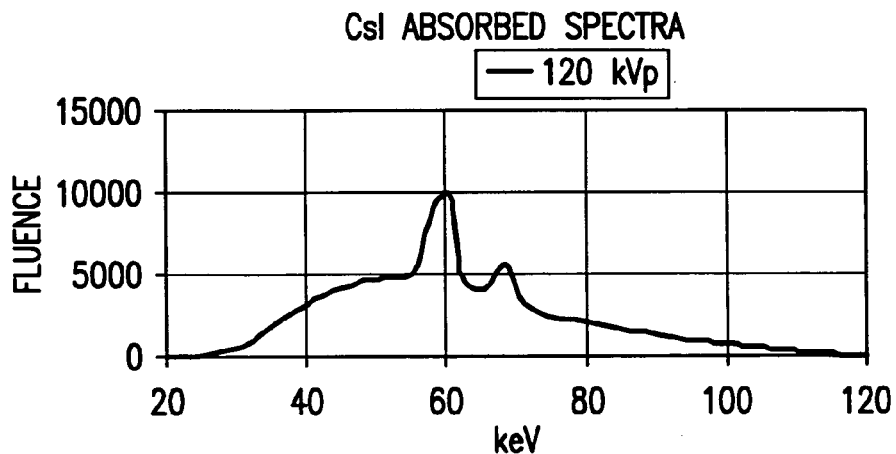
FIG. 14C shows model calculation results for detector adsorbed spectrum after passage through the phantom model.

FIGS. 14a, 14B and 14C provide the calculation results for air spectra after total filtration (FIG. 14A), detector entrance spectra through the AAPM chest phantom (FIG. 14B) and CsI scintillator detector absorbed spectra (FIG. 14C).

EXAMPLE 2

Single-scan Dual-energy Imaging

Initial multi-spectral investigations were modeled with a dual-energy scan configuration, using typical spectra as obtained at 120-kVp and 2-mm Al and 3-mm Cu filtration; and 60-kVp and 2-mm Al filtration, respectively. With a beam width of 10-mm at the detector, and a pixel size of 127-μm, the primary beam illuminated 79 pixels and the effective exposure time was 315-ms for any point in the object. Tube currents of 12 and 6-mAs at 120 and 60-kVp respectively led to a (constant) tube current of 60-mA, and 52 and 26 samples at 120 and 60 kVp respectively. Tables 4 and 5 below list various model input parameters and output relating to the phantom, dual-energy techniques, filtration, and detector parameters.

TABLE 2

Input and output parameters for a single-spectrum chest radiography scan

| Beam width mm | pixel size μm | # of pixels | Readout ms | Exposure ms | Tube current mA | Scan length mm | Scan time s |
|---|---|---|---|---|---|---|---|
| 10 | 127 | 79 | 4 | 315 | 5.2 | 430 | 13.5 |
| Total Al: | Al | 5 | | | | | |
| Filter | Al-filt: | 2 | | | | | |
| Filter | Cu | 0 | | | | | |
| Phantom | Acrylic | 100 | | | | | |
| Phantom | Water | 0 | | | | | |
| Phantom | Al | 3 | | | | | |

TABLE 4

Phantom, techniques, and filtration parameters for dual-energy single scan acquisition

| Beam width mm | pixel size microns | # of pixels | Readout ms | Exposure Time ms | Tube mA | Scan Length | Scan time |
|---|---|---|---|---|---|---|---|
| 10 | 127 | 79 | 4 | 315.0 | 57 | 430 | 13.5 |

|  |  | kVp: | |
|---|---|---|---|
|  |  | 120 | 60 |
|  | mAs: | 12 | 6 |
| Filter | Al-filt: | 2 | 2 |
| Filter | Cu | 3 | 0 |
| Phantom | Acrylic | 100 | 100 |
| Phantom | Water | 0 | 0 |
| Phantom | Al | 3 | 3 |

TABLE 5

Dual-energy characteristics.

| | Techniques: kVP: | |
|---|---|---|
| | 120 | 60 |
| | mAs | |
| | 12 | 6 |
| Air Exposure | | |
| SID-scaled mAs | 6.1 | 3.1 |
| Fluence/mm*2 | 678461 | 1142230 |
| u-Gy: (scaled to 117-cm) | 22.2 (31.8) | 61.5 (88) |
| Samples per kVp: | 52 | 26 |
| Photons per sample: | 209 | 703 |
| CsI quantum efficiency: | 0.4 | 0.5 |
| Mean energy (keV): | 86.9 | 37.7 |
| Air Signal (electrons): | 285583 | 589084 |
| HVL | 13.4 | 2.6 |
| Exposure behind AAPM Phantom. | | |
| Fluence/mm*2 | 74308 | 36137 |
| u-Gy: | 2.5 | 1.4 |
| Photons per sample: | 45 | 44 |
| Mean energy (keV): | 88.8 | 43.5 |
| CsI absorbed spectra and signals | | |
| Fluence/mm*2 | 43443 | 35430 |
| Photons per sample: | 14 | 20 |
| Mean energy (keV): | 85.1 | 43.5 |
| Electron per X-ray: | 1388 | 964 |
| Integrated SNR: | 26.4 | 23.8 |
| Quantum SNR (no e-noise): | 26.5 | 23.9 |
| Signal (e): | 19583 | 19000 |
| Percent CsI absorption: | 58.5 | 98.0 |

Figure 15A:
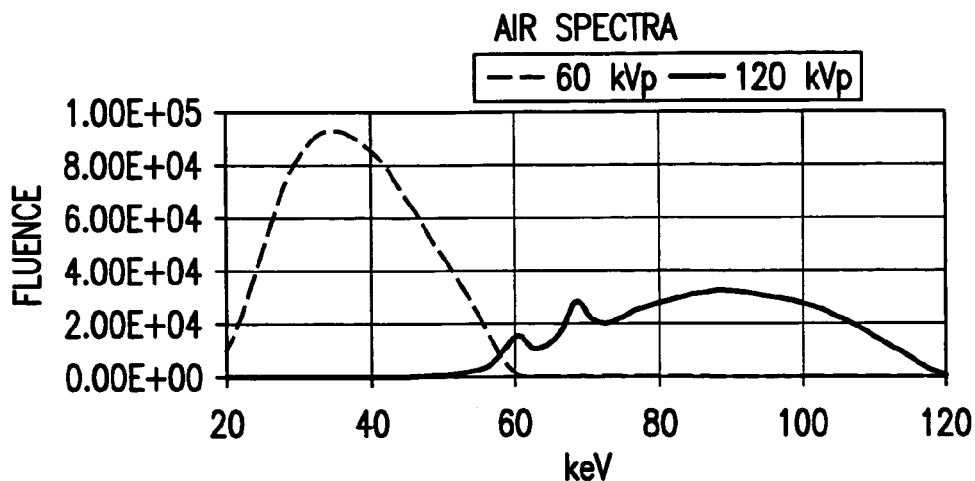
FIG. 15A shows different model calculation results for two X-ray spectra for a dual-energy application in air after total filtration.
Figure 15B:
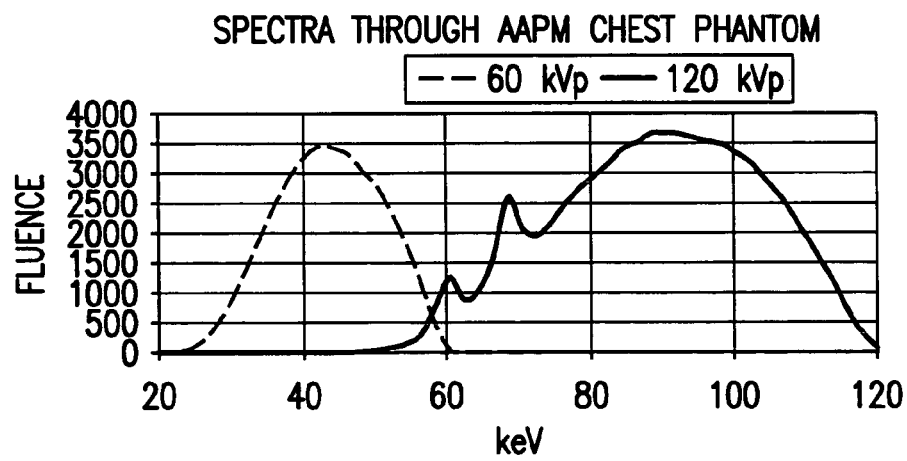
FIG. 15B shows X-ray spectra after passage through a standard chest phantom target.
Figure 15C:
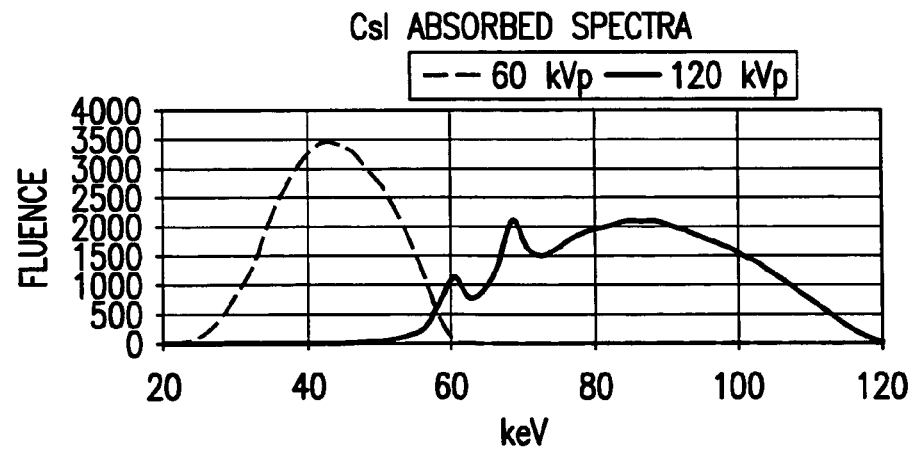
FIG. 15C shows model calculation results for detector adsorbed spectra after passage through the phantom target.

FIGS. 15A, 15B, and 15C show simulation results for single-scan dual energy imaging. The spectra shown represent, respectively, spectra in air after filtration (FIG. 15A); spectra behind the AAPM chest phantom (FIG. 15B); and spectra absorbed by CsI (FIG. 15C).

EXAMPLE 3

Single-scan Imaging with Six Spectra

A simulated a six-spectra acquisition is shown below for illustration of how this methodology may be applied in a more general sense. Tables 6 and 7 list the corresponding spectral characteristics. In this experiment, two additional low-energy spectra were designed to have mean energies just below and just above the K-edge of Iodine.

TABLE 6

Techniques for a six-spectra AAPM chest phantom simulation

| Beam width mm | pixel size microns | # of pixels | Readout ms | Exposure ms | Tube current mA | Scan length mm | Scan time seconds |
|---|---|---|---|---|---|---|---|
| 12 | 127 | 94 | 6 | 566.9 | 120 | 430 | 20.3 |

| | | kVp: | | | | | |
|---|---|---|---|---|---|---|---|
| | | 140 | 120 | 100 | 80 | 60 | 40 |
| Total Al: | Al | 5 | 5 | 5 | 4 | 5 | 5 |
| Filter | Al-filt: | 2 | 2 | 2 | 1 | 2 | 2 |
| Filter | Cu | 5 | 5 | 4 | 1 | 0 | 0 |
| Filter | Ce | | | | | 0.4 | 0 |
| Filter | Hafnium | | | | 0.2 | | |

TABLE 6-continued

Techniques for a six-spectra AAPM chest phantom simulation

| Filter | iodine | | | | | | 0.1 |
|---|---|---|---|---|---|---|---|
| Phantom | Acrylic | 100 | 100 | 100 | 100 | 100 | 100 |
| Phantom | Water | 0 | 0 | 0 | 0 | 0 | 0 |
| Phantom | Al | 3 | 3 | 3 | 3 | 3 | 3 |

TABLE 7

X-ray characteristics of a six-spectra AAPM-phantom simulation

| | | kVp: | | | | | | |
|---|---|---|---|---|---|---|---|---|
| | | 140 | 120 | 100 | 80 | 60 | 40 | 140–120 |
| | | | | mAs: | | | | |
| Settings: | | 5 | 7 | 15 | 6 | 15 | 20 | (or sum: Σ=) |
| *Air exposures* | | | | | | | | |
| SID-scaled mAs | | 2.6 | 3.6 | 7.7 | 3.1 | 7.7 | 10.2 | |
| Fluence/mm*2 | | 218134 | 124946 | 134016 | 109091 | 171207 | 318211 | |
| Kerma (scaled to 117-cm) | u-Gy: | 8.4 (12.1) | 4.3 (6.2) | 4.0 (5.8) | 3.2 (4.6) | 8.5 (12.2) | 24.0 (34.4) | Σ = 52.6 (75.2) |
| Samples per kVp: | | 7 | 10 | 21 | 8 | 21 | 28 | Σ = 94 |
| Photons per sample: | | 506 | 207 | 104 | 211 | 132 | 185 | |
| CsI quantum efficiency: | | 0.4 | 0.4 | 0.5 | 0.5 | 0.5 | 0.6 | |
| Mean energy (keV): | | 102.8 | 93.3 | 80.0 | 58.8 | 36.6 | 29.0 | |
| Air Signal (electrons): | | 759596 | 281963 | 120970 | 199530 | 90913 | 136779 | |
| HVL | | 15.2 | 14.3 | 12.5 | 8.6 | 3.3 | 1.8 | |
| *Entrance detector exposures behind the AAPM phantom* | | | | | | | | |
| Fluence/mm*2 | | 26932 | 14468 | 13863 | 8389 | 4801 | 3190 | |
| | u-Gy: | 1.1 | 0.5 | 0.4 | 0.2 | 0.2 | 0.2 | Σ = 2.6 |
| Photons per sample: | | 63 | 24 | 11 | 16 | 4 | 2 | |
| CsI quantum efficiency: | | 0.4 | 0.4 | 0.5 | 0.5 | 0.5 | 0.6 | |
| Mean energy (keV): | | 104.6 | 94.5 | 80.9 | 59.7 | 39.3 | 31.7 | |
| Electron per X-ray: | | 1500 | 1356 | 1161 | 947 | 564 | 503 | |
| Integrated SNR: | | 13.2 | 9.9 | 9.9 | 8.0 | 5.5 | 4.2 | |
| Quantum SNR (no e-noise): | | 13.2 | 9.9 | 10.0 | 8.1 | 6.2 | 5.3 | |
| Signal (e): | | 37514 | 13663 | 5604 | 7373 | 1048 | 512 | |
| *CsI absorbed spectra and signals* | | | | | | | | |
| SID-scaled mAs | mAs | 2.6 | 3.6 | 7.7 | 3.1 | 7.7 | 10.2 | |
| Fluence/mm * 2 | | 11938 | 7582 | 9212 | 7588 | 4715 | 3190 | |
| Photons per sample: | | 23 | 11 | 6 | 12 | 3 | 2 | |
| Mean energy (keV): | | 99.8 | 91.6 | 79.3 | 59.3 | 39.3 | 31.7 | 114.2 |
| Integrated SNR: | | 13.9 | 11.0 | 12.1 | 11.0 | 8.3 | 6.7 | |
| Quantum SNR (no e-noise): | | 13.9 | 11.1 | 12.2 | 11.1 | 8.7 | 7.2 | |
| Signal (electrons): | | 35214 | 14659 | 7198 | 12066 | 2296 | 1258 | |
| Percent CsI absorption: | | 44.3 | 52.4 | 66.4 | 90.4 | 98.2 | 93.7 | |

Figure 16A:
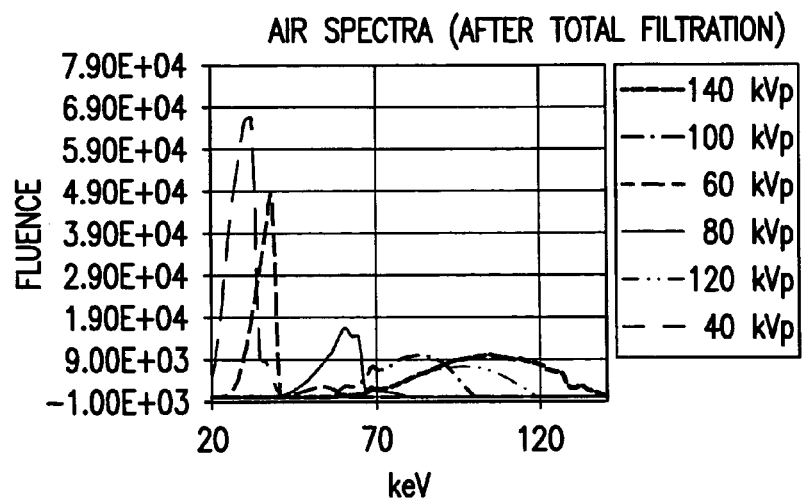
FIG. 16A shows total X-ray emissions in air after total filtration according to a plurality of X-ray sub spectral bands.
Figure 16B:
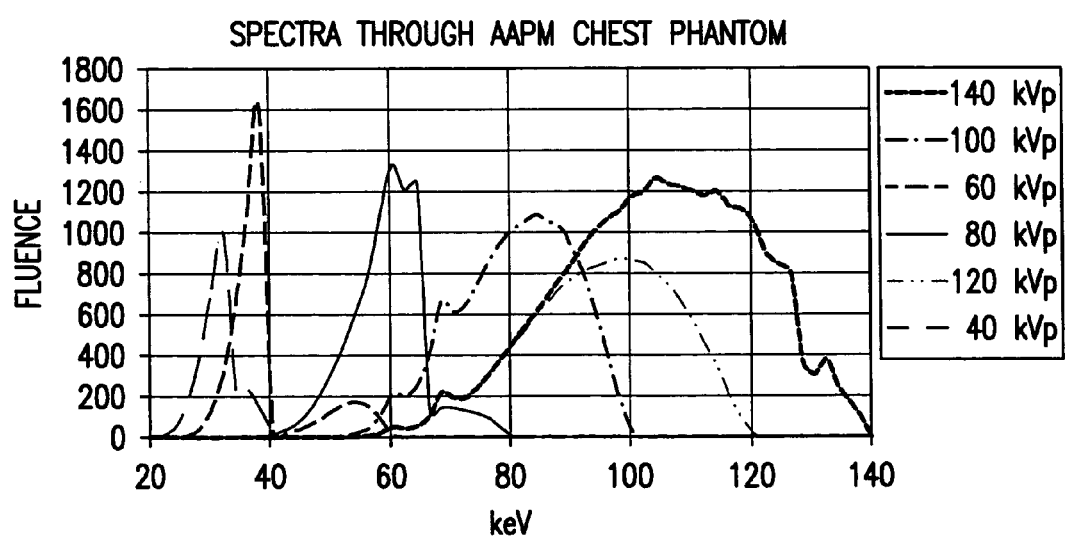
FIG. 16B shows multi-spectral passage after adsorption through a standard chest phantom target.
Figure 16C:
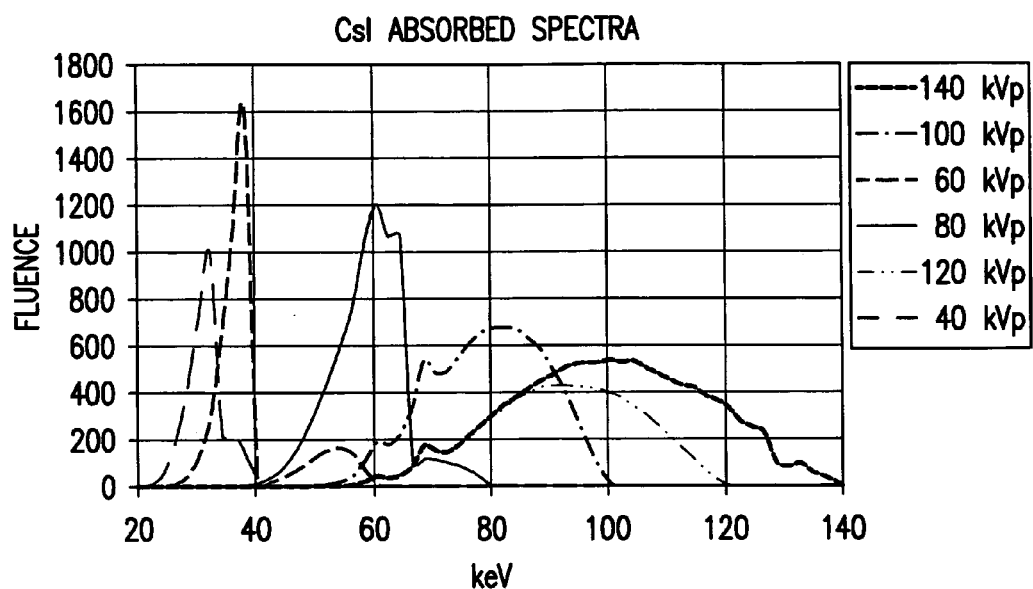
FIG. 16C shows multi-spectral detector adsorption.
Figure 16D:
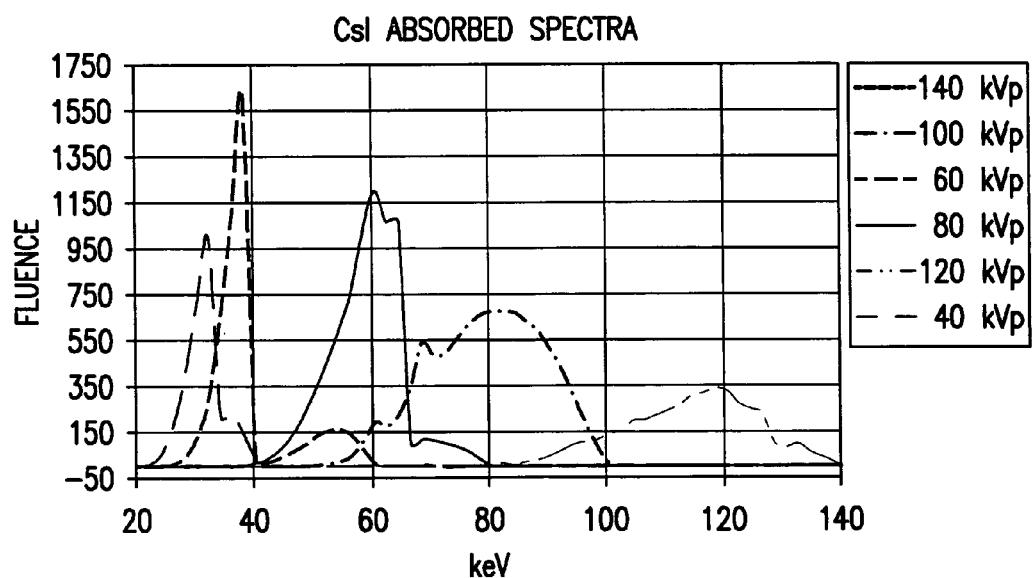
FIG. 16D shows detector signal emissions corresponding to the detector adsorbed spectra.

FIGS. 16A, 16B, 16C, and 16D illustrate the effectiveness of filtration to shape an initial broadband filter obtained with Tungsten at 140, 120, 100, 80, 60, and 40-kVp respectively., in a Single-scan multispectral acquisition with six spectra. The respective figures show air spectra after beam filtration (FIG. 16A); spectra behind the AAPM phantom (FIG. 16B); CsI-absorbed-spectra (FIG. 16C); and resulting five input spectra (FIG. 16D) (inputs to the image decomposition processing step).

EXAMPLE 4

Single-scan Dual-energy Imaging—Second Example

The filtration for the 60-kVp spectrum of Example 2 and 40-kVp spectrum of Example 3 were retained for a second dual-energy simulation. A layer of 10-cm of water was added to the AAPM phantom definition to simulate a larger patient. (Tables of input and output parameters not shown.) The mAs techniques were increased as compared to the first dual-energy experiment (10- and 20-mAs at 60- and 140-kVp in this simulation as compared to 6- and 12-mAs at 60- and 120-kVp). The entrance air-kerma was raised from 120-µGy to 140-µGy; the absorbed signal SNRs decreased to 5.6 and 11 for the low- and high-energy beams, as compared to 26 and 24 respectively. The entrance exposure to the detector (total 1.3-µGy) showed the effect of the increased attenuation introduced by the 10-cm water layer; this effect was compensated in part by the CsI larger absorption at lower energies (absorbed mean energies of 46- and 101-keV respectively). For this 10-mm beam-width simulation, the tube current was 64-mA.

Figure 17A:
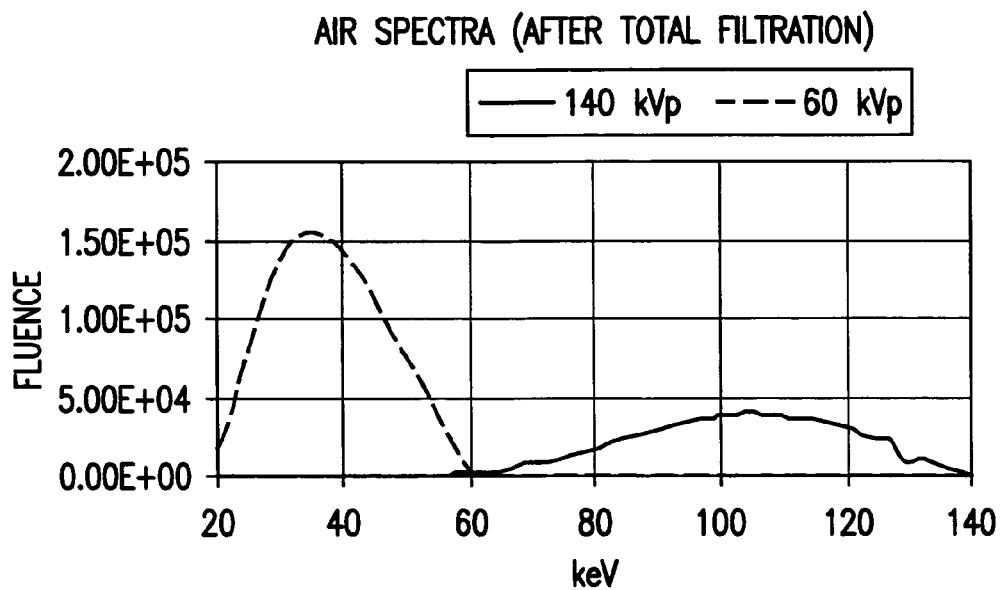
FIG. 17A shows total X-ray spectra in air for a dual-energy application after total filtration according to model calculations.
Figure 17B:
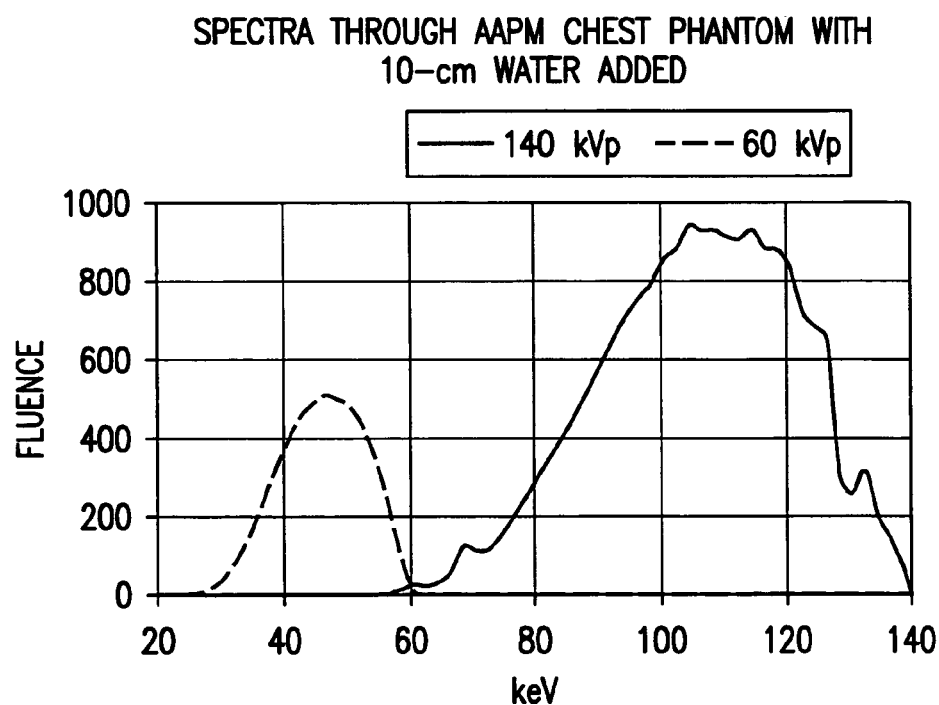
FIG. 17B shows model calculation results indicating remaining spectra after adsorption in a standard chest target.
Figure 17C:
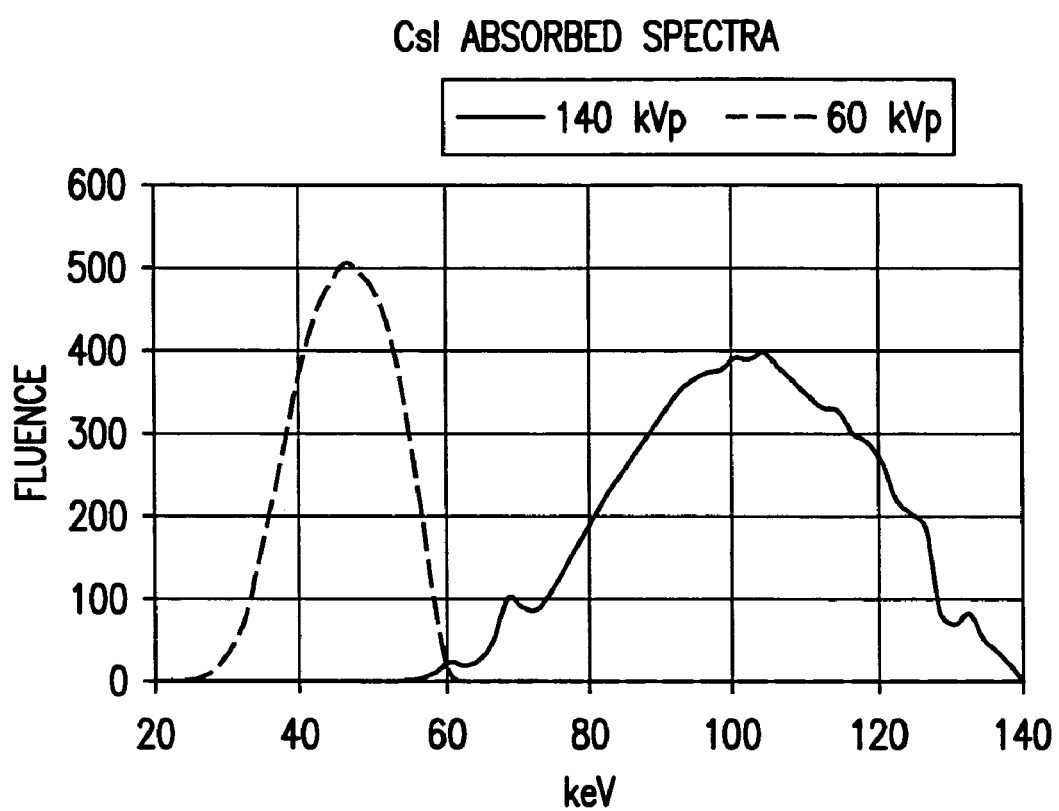
FIG. 17C shows detector adsorbed spectra.

FIGS. 17A, 17B, and 17C show the results including air spectra after total filtration (FIG. 17A); spectra through AAPM chest phantom (FIG. 17B); and CsI adsorbed spectra (FIG. 17C).

Model Validation and Discussion of Examples

Figure 1:
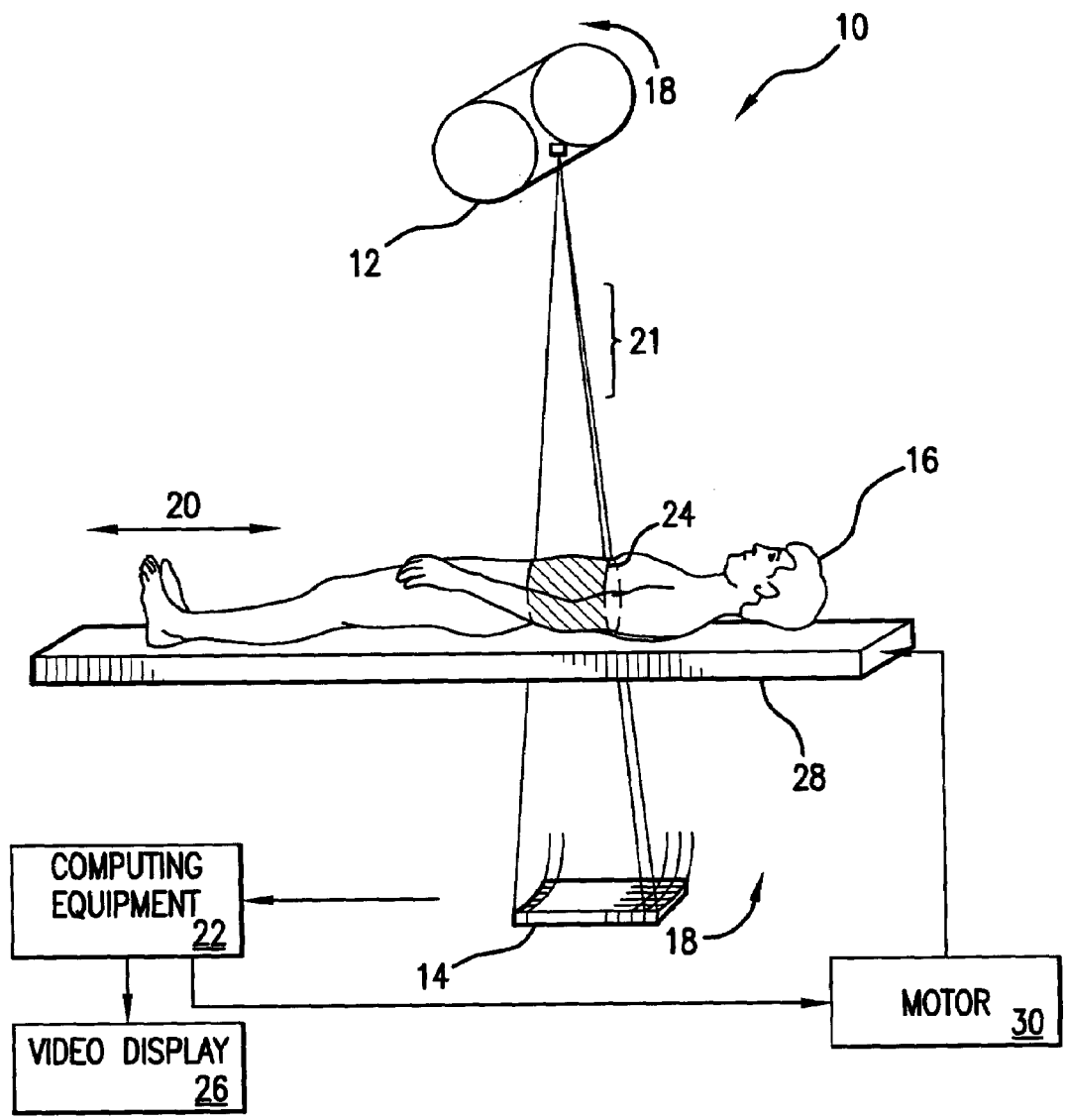
FIG. 1 is a schematic diagram illustrating a prior art imaging system for use in projection imaging or computed tomography (CT)

The half-value layer (HVL) values higher than expected in all experiments. For example, there was shown 5.2-mm in for the 120-kVp, 2-mm Al filter spectrum in Example 1, as compared to a mean of 4.2-mm in clinical practice (Spelic, 2002). One possible contributor to the higher HVL is the 2-kev bin width in the polynomial fit model used (Boone, 2000), which appears to smooth the Tungsten K-edges, and may have underweighted the corresponding fluences. Selection of a single beam spectrum at 120-kVp was made in part to cross-check model consistency. This spectrum exhibited significant beam hardening (from 56-keV mean energy in air to 65-kev behind the phantom, Table 3). The mean energy in air (56-keV) was in excellent agreement with that published by Boone (55-keV; Boone, 2000, FIG. 1. 39), and the data were consistent with the model. The absorbed spectrum (behind the phantom) reflected the decreased attenuation of CsI with increased energy. The CsI K-edge effect was seen in comparing the reduced absorption for the 40-kVp spectrum as compared to the 60-kVp spectrum: the 40-kVp spectral distribution led to an absorbed mean energy of 31.7 keV, just below the K-edges of Cesium (35.96 keV) and Iodine (33.2 keV) (Table 6); see also FIGS. 17A through 17C.

The following observations were made from the model results. First, it was found that for a target detector exposure (behind the phantom) of 4 to 8 µGy, the resulting tube currents were low (less than 120-mA) even when using a fraction of the full detector width (10 to 12-mm primary and 25-mm active detector width). Tubes are available from several vendors with significant higher specification than this. With a pixel size of 127 microns, it was found that the expected mean number of detected photons at all spectra of interest (with kVps in the range 60 to 140 keV) were comfortably larger than 0, and typically larger than 16 (except for the larger-patient dual-energy case). When combined with typical conversion factors between X-rays of various energies and number of electrons per X-ray in CMOS (based on CsI efficiency, light conversion factors, and CMOS spectral sensitivities), we found that the system was quantum noise limited. Even a factor two or more increase in the electronic noise didn't significantly change this finding: full-frame sampling will not lead to SNR degradations.

In the first dual-energy experiments, the incident numbers of photons per sample were respectively 23 and 22 for the two spectra. Accounting for the CsI attenuation led to 13 and 21 absorbed photons, this difference being compensated by the amount of light produced by CsI and electrons generated at mean energies of 85 and 44 keV, respectively.

The main findings were found to also extend to a single-scan six-spectra acquisition. Inspection of the associated results (FIGS. 16A to 16D and Tables 5 and 6) confirms spectra separation and quantum-limited SNR performance in all but the two lowest kVp spectra.

In the second dual-energy experiment of Example 4, the absorbed beam spectra were well separated, but the SNRs suffered from the 10-cm additional water absorption—at a relatively low 140-µGy entrance air kerma. In such a case, the input techniques might have to be increased, and the input spectra further optimized to improve SNR while keeping the patient dose relatively low. Imaging large patients will be facilitated by the use of at least 140-kVp for one of the single-scan spectra (Table 7).

In all multi-spectral data acquisition, beam-hardening was significantly reduced as compared to the single-spectrum acquisition. In the dual-energy case, the effective energy went from 87 to 89-kev (120-kVp) and 38 to 44-keV (60-kVp) respectively. Increasing the number of spectra while maintaining spectrum separation required use of higher filtration and tube currents (from 57 to 120-mA from two to six spectra). In all cases, the scaled entrance exposure to the patient, respectively, at 118,120, 89, and 94 µGy, was comparable or less than the mean values reported by NEXT for adult chest X-rays, which is 120 µGy for screen-film and 160 µGy for digital, as reported by Spelic, 2002. Except for the six-spectra experiment and the large-patient dual-energy simulation, where the 60 and 40-kVp spectra suffered from limited flux and penetration, the number of photons per digital sample was large enough to render electronic noise negligible, as evidenced by comparing the "quantum" and "integrated" SNRs. The CsI thickness used (0.9-mm) is consistent with the pixel size retained for these results (127-µm); optimized resolution-absorption trade-offs might result in a thinner CsI being retained. The maximum air signals calculated per digital sample were 852,944 and 1.4 million electrons (140-kVp at six-spectra, Table 8; and second dual-energy simulation). While the air signal was over-estimated by a factor 1.43, corresponding to scaling to the phantom entrance, higher techniques are expected for lateral views. The detector in its current design will not saturate until the signal reaches 100 million electrons. This indicates sufficient latitude to optimize the design for our application while ensuring the detector always records a usable air signal.

FIGS. 14 to 17 (including subfigures) and their accompanying Tables demonstrate that selected filter materials led to well-separated, relatively narrow-band spectra with sufficient X-ray flux. Taken in combination with the narrow primary beam-width, relatively low tube currents, and quantum noise-limited behavior, the results support early full-frame sampling single-scan multispectral design feasibility. Most of the filter materials investigated are commonly used in X-ray imaging; however, hafnium is not in common usage. Additional materials may be selected by following the pattern of modeling reported above.

The model may also allow optimization of beam width for intended applications. Results show that a 10-mm beam width with a 25-mm detector width will allow penumbra imaging, automatic beam tracking, and scatter detection and correction. At the illustrated sampling rate of (4 ms), the scan time for a full-field of 43-cm is less than 15 seconds, which is similar to helical CT scan times and well within the typical breath hold that is sustainable by most patients. Certain tradeoffs exist between tube power and focal spot size, SNRs, and detector design, that are associated with a significantly reduced sample time, e.g., to about 1-ms, with the goal of reducing practical scan times to 5-seconds or less.

Section A.9—X-ray Generation Optimization: Tube, Beam Filtration Sub-System

The X-ray tube of source 112 may be an off-the-shelf FDA-certified component. A number of commercial solutions are available from vendors such as Varian and Dunlee for the power requirements indicated by the model results, e.g., <200 mA; <20-s scan. Likewise, several companies including Del Electronics, Quantum Medical, and Medstone, have commercially available high-power generators that are suitable for these purposes. In principle system 100 could be operated in either pulsed or continuous mode, where 4-ms pulses are common in the art. By design, the system utilizes accurate techniques control. Fast and precise kVp switching has become possible with high-frequency generators. With this high-power technology, the tube power is modulated by the frequency of very short pulses (Sobol, 2002; Krestel, 1990). Tube and generator designs may be specified on commercial order for key aspects of electron optics, such as tube grid, focal-spot shape, distribution and size, as well as focal-spot blooming behavior. Other such specifications may include thermodynamic specifications for anode and housing thermal capacity and cooling delays. Power generation aspects such as input line requirements, on-board energy storage, and cable length specifications are similarly specified for the intended application.

The merits of K-edge filters versus standard materials such as aluminum and copper have been investigated in many studies (for example, Koedooder and Venema, 1986; Riederer et al., 1981). Variations in filter material tolerances, such as thickness and composition may be averaged across a number of rows and filter wheel arc dimensions.

Section A.10—Scanning

Attention to the design details of the scanning mechanisms assures that image quality will not be degraded by vibrations, initial velocity ramp-up, gantry flex and other related considerations. A linear scan trajectory and a servo-motor with a feed-back mechanism may facilitate control of the scan velocity well within a detector pixel dimension. By way of example, suitable devices for inclusion in gantry 610 (FIG. 6) are obtainable on commercial order include a motor from Danaher Corp. or Pacific Scientific, with a linear encoder provided by Minarik Corp. or Renishaw PLC. Such a design, when combined with the full-frame sampling approach, facilitates scanning with variable velocity.

Figure 18:
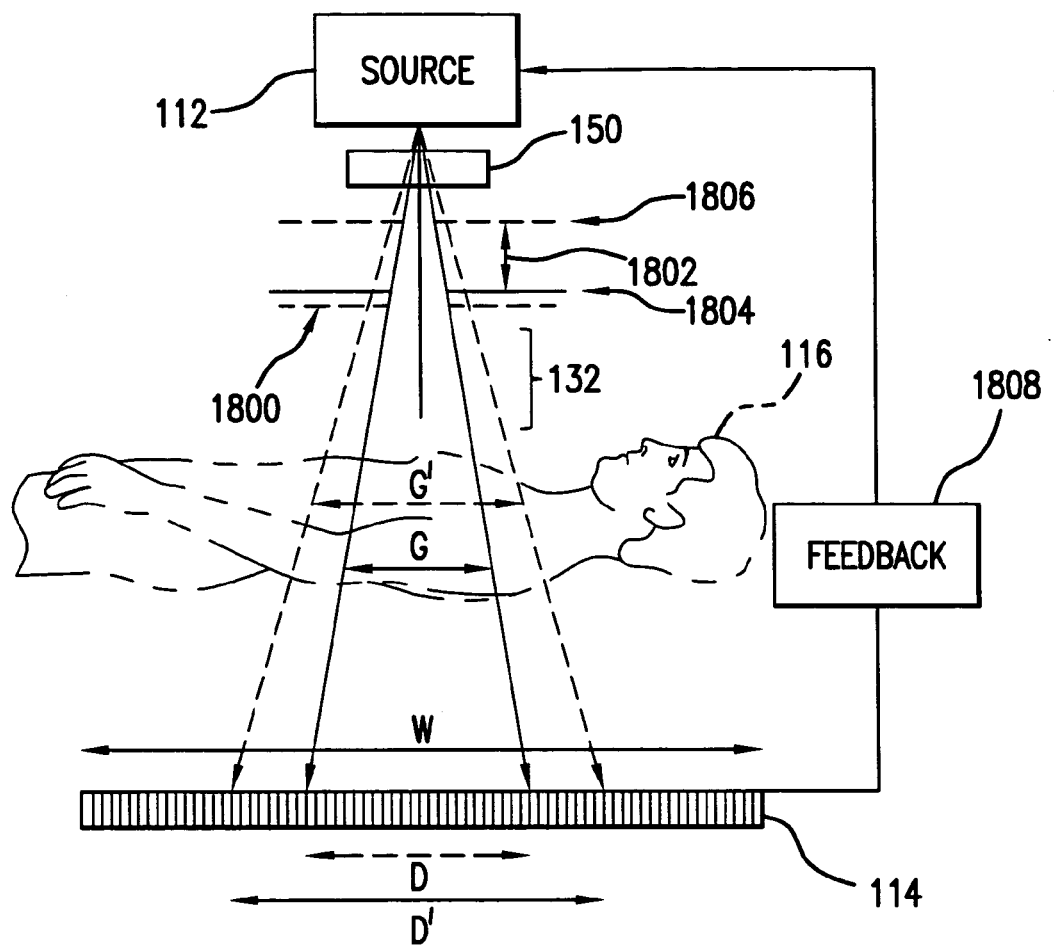
FIG. 18 shows feedback control of under-collimated source emission spectra to position an X-ray beam through a subject body.

FIG. 18 illustrates the principle of real-time electronic beam tracking via feedback-loop, and also adaptive beam width and scatter-to-primary equalization. Source 112 emits X-rays on paths, which may be dynamically adjusted to impinge upon detector array 114 in widths D or D' by virtue of positioning a motor-actuated collimator 1800 on track 1802 relative to source 112 at position 1804 to achieve width D or position 1806 to achieve width D' Computing equipment 122 is programmed with feedback instructions 1808 to select for a desired width D along the width W of detector array 114 by detecting impingement on a row-pixel or column-pixel basis and adjusting the distance on track 1802 between the source 112 and collimator 1800, or by adjusting the collimator aperture width by moving the collimator blades inwards or outwards. Sampling the beam penumbra on paths 132 with a few pixels allows automatic beam characterization and position determination by virtue of the feedback instructions 1808, and the relative beam projection width D or D' with respect to the detector width W can be accurately calculated from the data. These elements provide for tube-tracking of the detector without mechanical linkage, adaptive velocity scanning, and tracking beam following tube track switching. By way of example, with a typical nominal focal spot size of 0.6-mm, and typical SID of 160-cm, the projected beam penumbra may covers a relatively few detector pixels, such as 5 to 7, dependent on collimator design. The beam spot may be adjusted for any detector size of configuration.

In a first approximation, and assuming constant techniques, the scatter-to-primary ratio is proportional to the beam width G: the recorded scatter is proportional to the product of amount of scatter generated (itself proportional to the beam width G) times the amount of image scatter recorded (proportional to the active image formation width on the detector (D∝G)). The primary is proportional to G. Accordingly:

$$S/P \propto {(G \times G)}/{G} = G,: \quad (1.29)$$

and:

$$S/P \xrightarrow[G \to 0]{} 0 \quad (1.30)$$

Figure 19:
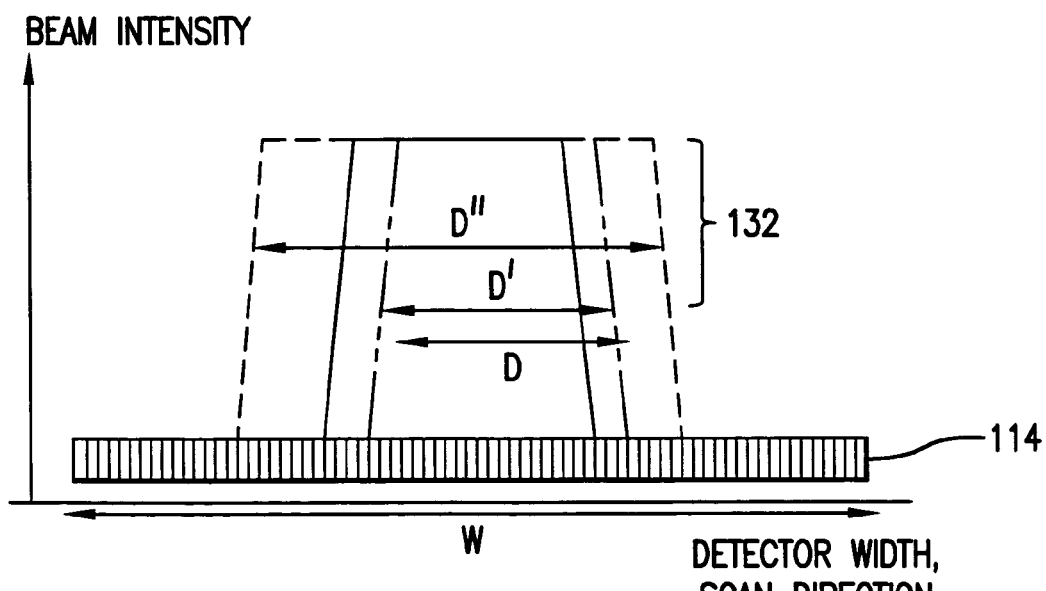
FIG. 19 illustrates different positioning options that may be obtained by virtue of collimation, positioning, or selection of a different x-ray tube anode track.

FIG. 19 shows, generally, that the beam width may be adjusted to any dimension D, D', or D", as the beam intensity from source 112 through the patient and the amount of scatter radiation detected outside the projected primary beam decreases or increases. This approach facilitates variable velocity scanning and elimination the mechanical linkage between the tube and detector. Additional benefits include real-time X-ray tube anode track switching and adaptive primary beam-width. Anode track switching may be associated with a shift of the beam position with respect to the detector, as illustrated in FIG. 19. Patient-dependent beam-width adaptation makes it possible to acquire data with a constant scatter-to-primary ratio, where the scatter-to-primary ratio S/P vanishes with smaller beam widths, as shown in FIG. 19 Finally, determination of the scanning orientation may be made, whether vertical or horizontal, depending upon the demands of a particular environment of use.

Section A.11—Image Decomposition

In the general imaging case for P wide-band input spectra, with or without the use of energy-sensitive and photon-counting detectors, the projection data are weighted by spectra of various distributions. With proper input spectrum normalization, a photon counting and energy-discrimination approach would be treated just as described above. More generally, a given projection measurement reflects a weighted average over a larger energy band. When data are collected for P spectra($\Im_i$),i=1, . . . , P, each spectrum S may be decomposed onto R energy intervals so that in a discrete representation, and assuming linearity:

$$\Im_i = (S_{i,1}, \ldots, S_{i,R}) \quad (1.31)$$

Accordingly each projection datum d is given by:

$$d_i = \sum_{q=1}^{q=Q} a_q \times (\Im_i)^T M_q, \quad (1.32)$$

where $M_q$ represents the q-th column vector of matrix M (R rows and Q columns) (c.f. equation (1.26)). In matrix equation:

$$D_{P \times 1} = ([\Im]_{R \times P})^T \times [M]_{R \times Q} \times A_{Q \times 1} \quad (1.33)$$

If we now set:

$$M_{P \times Q}' = ([\Im]_{R \times P})^T \times [M]_{R \times Q} \quad (1.34)$$

then it is clear that the problem is again posed in the form of equation (1.17), and the solution for decomposition onto known basis-functions is obtained by inversion of the system, as shown in equation (1.34). It should be noted that the Q basis functions might be given either by known elemental materials, or may be theoretically calculated or experimentally measured for known tissues, such as cancer types, or materials, such as iodine. Equation (1.34) reflects the assumptions of a linear model. It is reasonable to use a linear model, as above, considering that the absorbed spectra were very well separated with little overlap in the aforementioned model results. The problem may be linearized around the mean effective energy for each spectrum. Given the known Q materials onto which to decompose the linear-attenuation coefficients as a function of energy, it is clear that proper choice of the spectra-defining matrix [ℑ] contributes to the matrix singularity, and this is a design consideration when selecting filtration materials for use in filter 150. Numerical techniques are available to help select spectra and ensure that the matrix to be inverted is non-singular, or will reduce the degree of singularity, as measured for example by the number of singular values less than a given threshold. Due to noise, limitations in the practical number of spectra, and other practical and numerical considerations, it may be desirable to seek the decomposition onto a subset Q' of basis function that best explain the projection data.

In a more general approach when the spectra may not be considered narrow-band, the linear approximation of equation (1.34) does not hold and it is necessary to return to the general image formation model of equation (1.3). Inversion of such a more realistic model, for example, with overlapping spectra, requires the use of iterative methods, but allows modeling of a-priori information and the representation of the X-ray quantum statistics where the central limit theorem indicates that measured noise will be Gaussian following data summation. Inverse problems often are formulated in the context of noisy or incomplete projection data. To account for noisy data sets, such as due to X-ray quantum noise, or underdetermined data sets, much emphasis has been placed on statistical approaches, with inclusion of a-priori information into the model. For instance, in imaging a particular body organ with contrast medium, the presence of iodine in some of the anatomy may be known beforehand. A-priori information may also take the form of constraints on the decomposition coefficients, such as spatial constraints, for example, those related to the decomposition coefficient rate of change from one line-integral (pixel) to its neighbors. Methods that may be applied include Bayesian approaches, such as maximum a-posteriori. Practical approaches to solve such problems include various maximization methods, such as simulated annealing (Geman et al., 1984), use of concave surrogate functions (Ortega et al., 1970; Fessler, 2000), and several other numerical approaches (Press et al., 1999).

Figure 20:
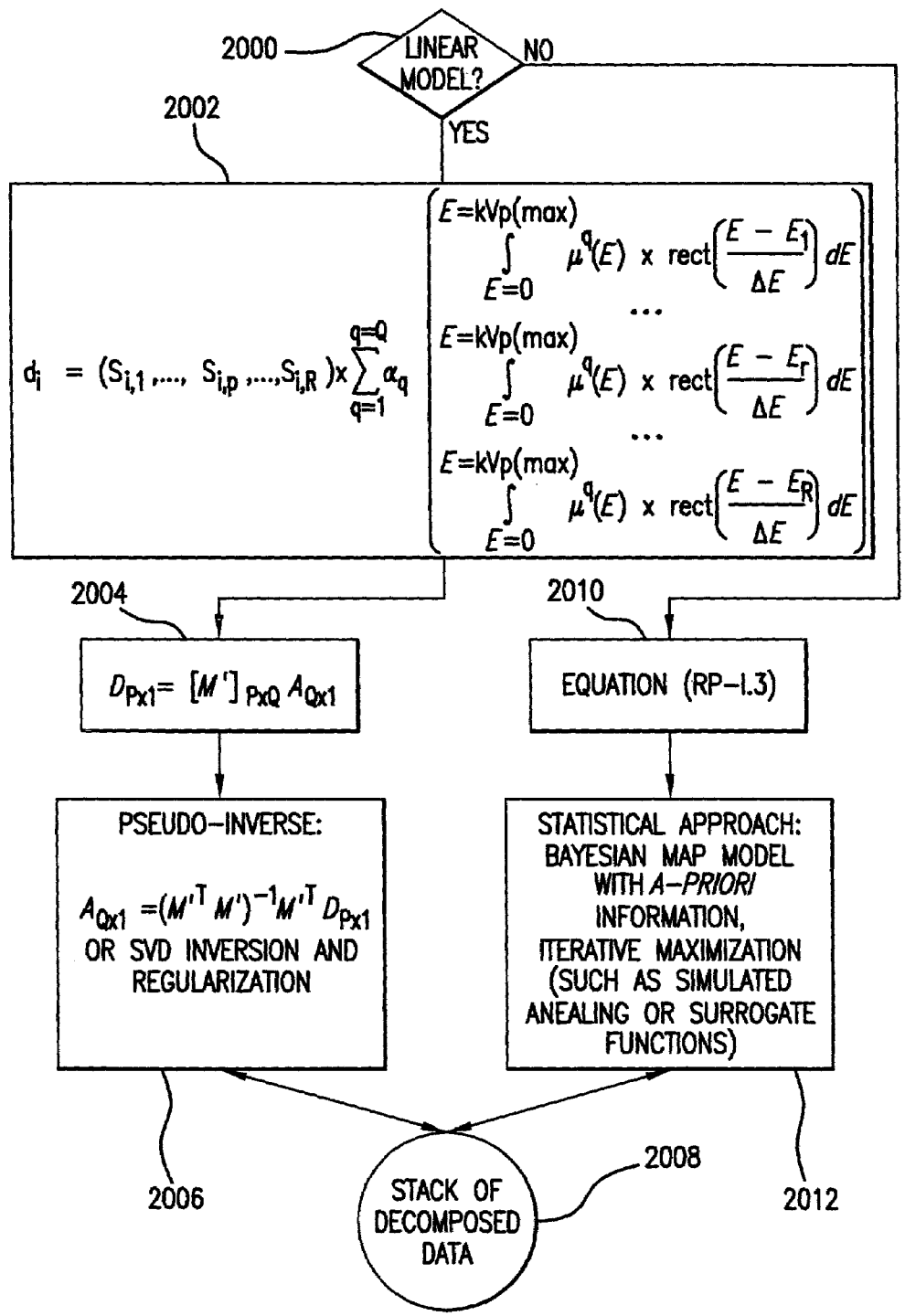
FIG. 20 is a flowchart representing model calculations for data decomposition.

FIG. 20 illustrates program logic for two possible data processing approaches in data decomposition. A first inquiry 2000 is whether the model is linear. If so, a simplified linear model in steps 2002 and 2004 associates each detector-absorbed spectrum with rectangular functions according to equations 1.23, 1.28, 1.32 and 1.33. The model may be inverted according to equation (1.28) in step 2006 to provide a stack of decomposed data 2008.

If the model is not linear, a more general image formation model, such as described by equation (1.3) is taken into account in step 2010, and decomposition proceeds per iterative methods allowing inclusion of a-priori information in step 2012. Data processing as per the left-branch requires linearization around the mean spectra energies. Narrow-beam imaging and reduced spectra overlap should allow useful first results to be obtained via linearization.

In general regarding FIG. 20, the line-integral decomposition onto a set of basis-functions in steps 2002–2006 may be performed by methods of linear algebra, such as the Singular Value Decomposition and/or principal component analysis. Alternatively, the decomposition may be performed iteratively in steps 2010 and 2012, such as by the use of a Bayesian model that includes the X-ray statistics and body attenuation processes. Such model then may lead to a solution by iterative methods such as conjugate gradients, use of surrogate functions with simple analytical extrema, or other relevant approaches. The statistical processing on the decomposed basis-function may, for example, be done by Bayesian mapping onto a set of empirically or theoretically derived base functions that indicate a suspected diagnosis, for example, a normalized multispectral line function observed from a cancer tumor. In this instance, the Bayesian mapping may identify curve characteristics that are unique to line-integral functions of this type.

Alternatively, an artificial learning algorithm, such as a neural network, may be trained to make this comparison and identification. For example, the neural network may be trained using full spectrum line functions that have been divided into bands. The line functions may be divided into healthy tissues and diseases according to a one of more types of disease. After training, the model may be inverted and used to produce a code assigning disease identifier to the line-integral function.

Section A.12—Alternative Multispectral System Design with Flat-Panel Detector and Scanning Narrow Beam, with Applications to Small-animal Imaging, Sample Imaging, Patient Imaging, and Security Imaging Several configurations are possible for multi-spectral sampling of the same line integral in an examination time that precludes motion artifacts. In one implementation, the detector is fully sampled at each location, corresponding to a given integration time. In such a situation, for a line-integral through the animal, T samples are acquired with possibly as many as M different spectra, at a frame rate mostly dictated by the desired signal-to-noise ratio (SNR) and the detector integration rate.

Figure 21:
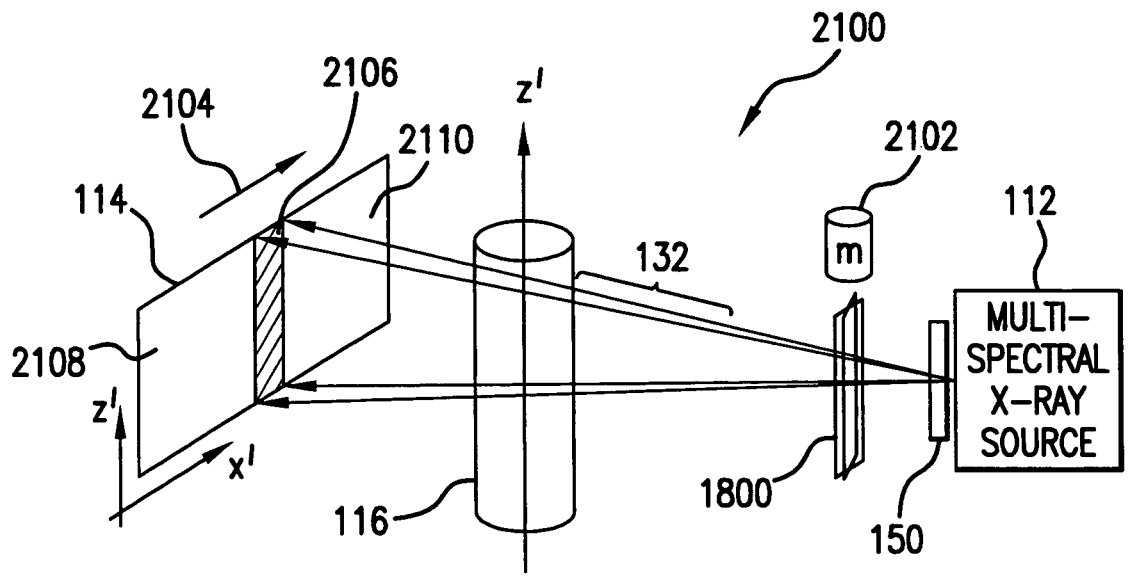
FIG. 21 shows multi-spectral source emissions applied to a sample container or object, such as may hold a small animal or industrial part, and illustrates the use of a narrow beam being scanned across the face of an area detector.

In one configuration 2100, system 100 uses a narrow beam-scanning system as shown in FIG. 21 in combination with a fast area detector array 114. A stepper motor 2102 moves the beam collimator 1800 (here a slot collimator) in synchrony with the data acquisition and spectral selection. The body 116 in this case is shown as a container that may, for example, hold a sample or small animal. As the beam on paths 132 scans across the body 116 in direction 2104, an active area 2106 of the detector array 114 may be electronically steered to sample the beam, or a full-frame of data is sequentially acquired on different areas 2106, 2108, 2110 of the detector array 114. As a result, M samples of essentially the same line-integral are acquired, where M depends on the number of detector rows/columns fully in the in primary beam projection, the relative motion of the beam with respect to the detector and detector sampling rate, and the type of binning (or data combination) selected. A high-frame rate, e.g., 1000 frames/s, may be provided by the CMOS detector design described below, and allows full scanning across the detector area in about one second—depending on field-of-view and other system specifications. Thus, a multi-spectral scanning beam geometry occurs along x' in synchrony with the detector read-out and the spectrum selection. Volumetric imaging is made possible by rotating and/or translating the body 116 with respect to the image chain.

Figure 22:
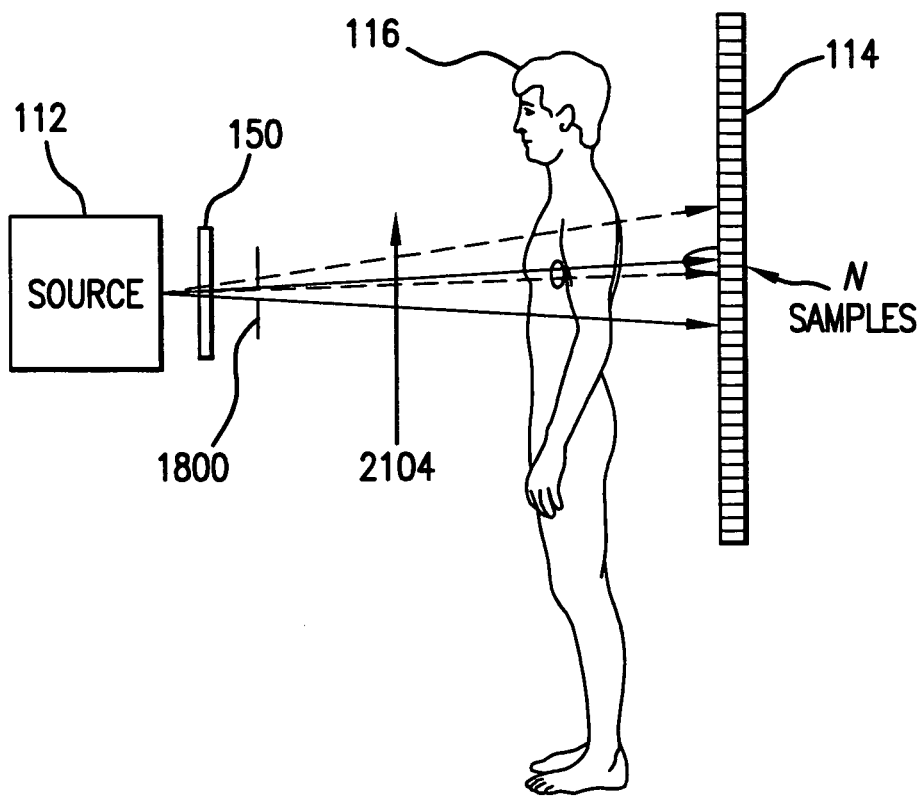
FIG. 22 shows an upright projection system for use in multi-spectral emissions with beam scanning.

In FIG. 22, the beam position and spectral contents vary with time, in synchrony with the data acquisition. As a result, up to T multi-spectral samples are acquired where T is related to the number of detector rows/columns that are fully illuminated at any time.

In scanning-beam approaches as currently implemented in the prior art, the samples corresponding to each detector row are typically summed. Current slot-scanning systems rely on the time-and-delay-integration (TDI) mode available on specific CCD designs. CCD refers to a semiconductor architecture in which a charge is read out of storage areas. In TDI mode, the charges are "rolled-over" from one CCD well to the next as a function of driving voltages or "phases." Accordingly, the read-out occurs after rollover and integration of the signal over as many wells are there are detector rows (or multiple of detector rows, in multi-phase CCDs) in the CCD design. This design allows integration of the signal while maintaining spatial resolution in scanning applications with a moving detector, if the detector velocity is exactly synchronized to the charge transfer internal to the CCD), but does not provide access to each sample. Indeed, the only sample available results of the integration over the entire width of the detector.

The configuration shown in FIGS. 21 and 22 offer one advantage over the prior art in that full frame digital sampling facilitates dynamic multi-spectral imaging, either with or without detector motion. It provides increased parameter selection flexibility and opens the door to leveraging the detected scatter radiation. Coherent (Rayleigh) scattering is an important attenuation phenomenon at low X-ray energies (10–30 keV) relevant to small animal imaging. Rayleigh scattering is predominantly forward directed, and accordingly may contribute a large component to the detected signal in the rows/columns directly adjacent the primary beam projection. Further away from the primary beam, Compton scatters are expected to be dominant. Both types of detected events may be leveraged to improve upon tissue characterization (Barrett and Swindell, 1981; Davidson et al., 2002). Additional research paths relevant to such system design include phase-contrast imaging (Wilkins et al., 1996).

System 100 may provide at least three user-selectable modes of operation:

(1) Dynamic multispectral data acquisition. In this mode, a pre-patient or animal collimator is scanned across the beam, so that the beam projections scans linearly across the width of the detector. By way of example, with a beam width of 2-mm at the detector, and a pixel size of 75-microns, about 27 detector columns (or rows, depending on the geometric arrangement retained) are in the beam umbra. With a beam scanning speed of one detector cell per sample time, a width of 100-mm is covered in 1.33 seconds. This mode allows essentially co-temporal and co-registered multispectral projection data acquisition.

(2) Multi-spectral sequential volumetric data acquisition. In this mode the full detector area is always illuminated by the beam, and the spectra are changed every sample time. In a dual-energy application, 500 projections can be acquired for each spectrum around the patient in a 1-second rotation.

(3) Fast-volumetric imaging, with acquisition of one full projection per sampling time (about 1-ms). This mode will allow three-dimensional data acquisition on a dense set of projections around the animal, so that to allow multiple volumetric CT samples to be acquired over a period of about 10-seconds (dynamic imaging of lung function will thus be made possible). The spectrum may be kept constant, or changed from one "full-data" acquisition to the next ("full-data" meaning one half-rotation plus fan-angle, one full-rotation, or one helical/spiral data acquisition depending on the level of tomographic accuracy required).

The system design may also allow for variable magnification. The use of a scanning narrow-beam such as 2-mm width indicated in Table 2, may enable excellent scatter rejection even with a "near contact" geometry (that is, with the animal holder being a few millimeters (10 to 20) from the detector). Such a geometry permits the use of a large focal spot tube, such as 0.3-mm or greater, while maintaining spatial resolution consistent with a 75-microns pixel (as demonstrated by a digital mammography system offering about 25-microns spatial resolution with a 0.3-mm focal spot tube (Besson et al., 2002)). A 0.3-mm Tungsten tube will support high techniques (such as the 81 -mA retained for the simulation shown in Table 2) (Besson et al., 2002). The geometry to be used in the other imaging modes will be optimized based on scatter-to-primary investigations, SNR considerations, and available X-ray tube specifications.

Section B—CT and Limited-angle CT

Section B.1—Input Beam Spectral Decomposition

EXAMPLE 5

A CT Beam Spectral Model

A CT beam was modeled as before using filtration to shape an initial broadband emission obtained from Tungsten at 140 and 80-kVp respectively. As before, all X-ray fluences are calculated from the TASMIP model (Boone, 1997; Boone, 2000). Although CsI is not appropriate for tomography (due to afterglow effects) it was used to provide a first indication of the effect of absorption efficiency and for compatibility in comparison with other model results reported herein. Table 8 shows the model input and output parameters.

TABLE 8

|  | Settings: kVP: | |
|---|---|---|
|  | 140 | 80 |
|  | mAs: | |
|  | 0.5 | 0.5 |
| Air Signal: | | |
| Photons per sample: | 85639 | 140503 |
| Mean energy (keV): | 102.8 | 59.8 |
| Behind phantom: | | |
| Photons per sample: | 1956 | 1407 |
| Mean energy (keV): | 105.9 | 62.6 |
| Absorbed: | | |
| Photons per sample: | 842 | 1223 |
| Mean energy (keV): | 101.4 | 61.9 |
| Percent CsI absorption: | 43.2% | 87.1% |

Figure 23A:
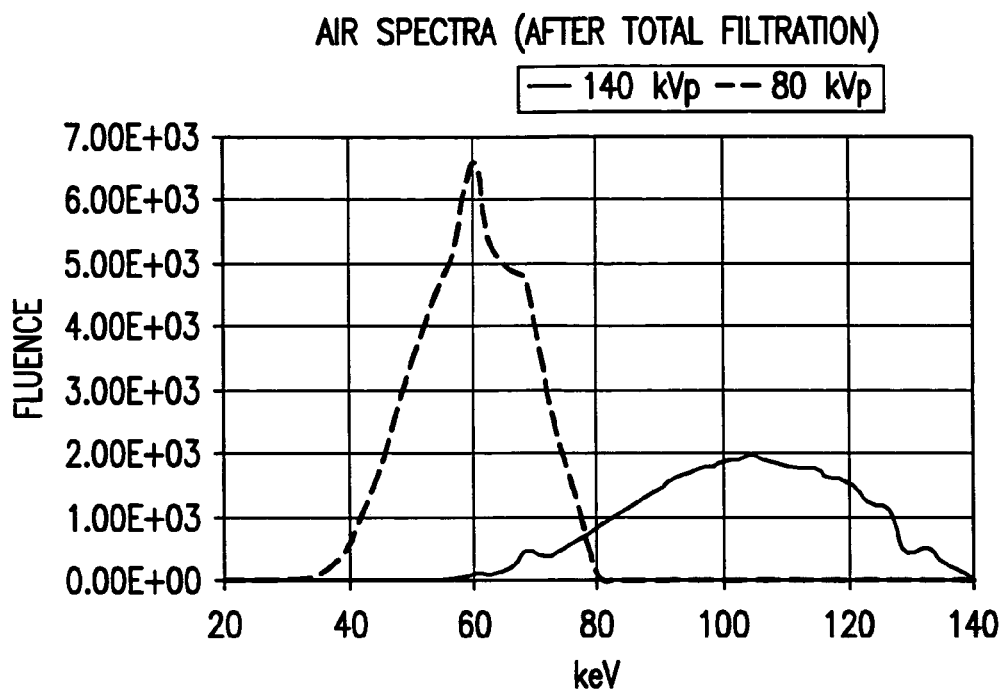
FIG. 23A shows CT model results for total X-ray emissions in air after total filtration for a dual-energy application.
Figure 23B:
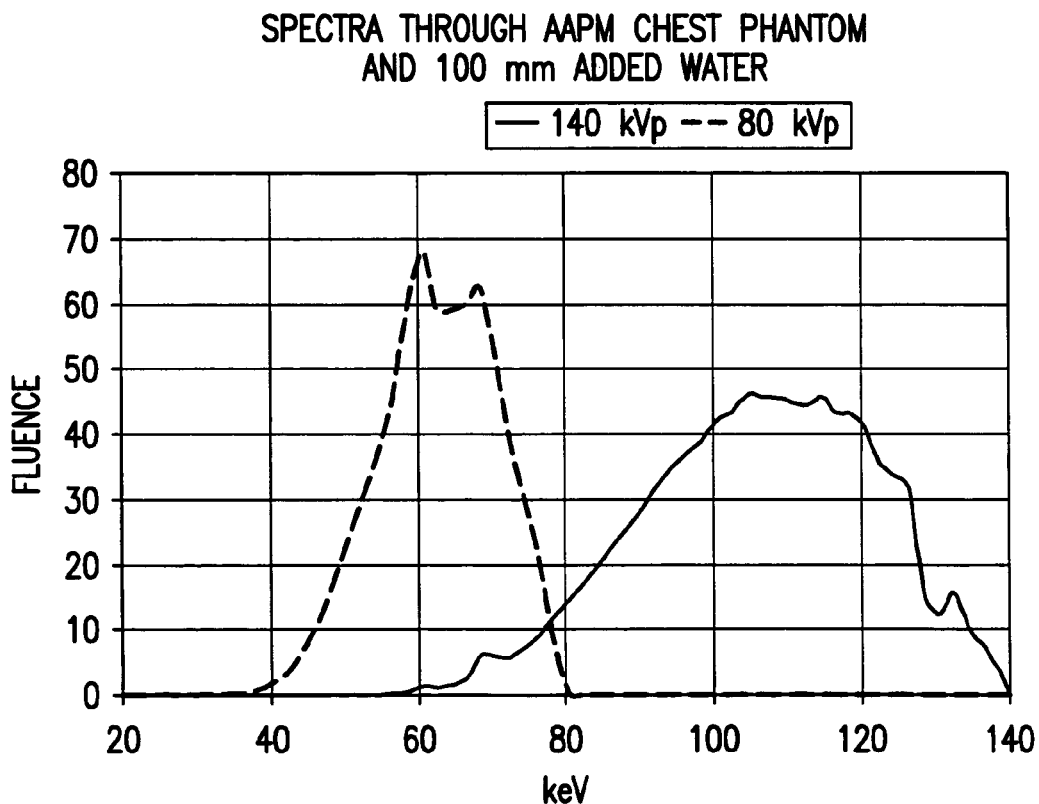
FIG. 23B shows CT spectral emissions after adsorption through a standard chest target.
Figure 23C:
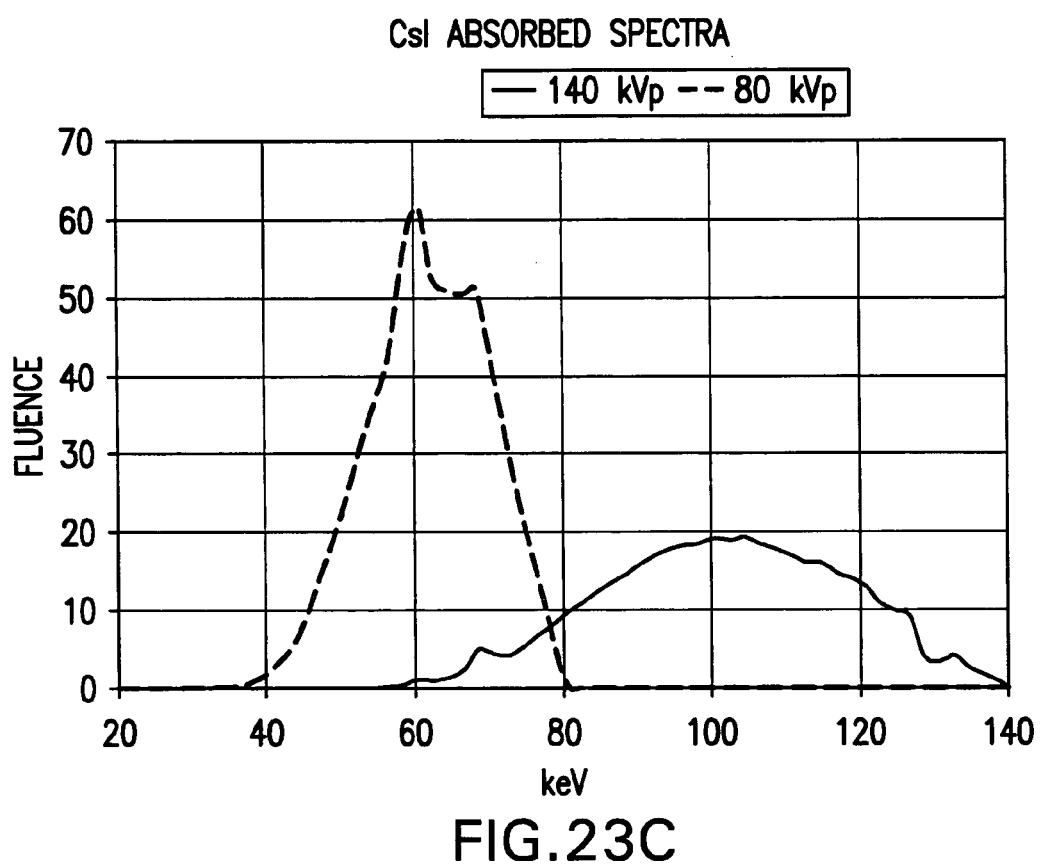
FIG. 23C shows model calculation results for detector adsorption in CT.

FIGS. 23A, 23B, and 23C show the model results for tungsten spectra obtained at 140- and 80-kVp and, respectively, using 2-mm Al, 5-mm Cu and 1-mm Al, 1-mm Cu filtration. The figures include Air spectra after filtration (FIG. 23A); spectra behind the AAPM chest phantom, here composed of 101.6-mm of Acrylic and 3-mm of Aluminum plus 100-mm of water; and spectra as absorbed by 0.9-mm of CsI (FIG. 23C). All X-ray fluences expressed as photons per $mm^2$ at 100-cm. The simulations assumed a 100-cm source to detector distance and a 1-mm detector area.

Figure 24:
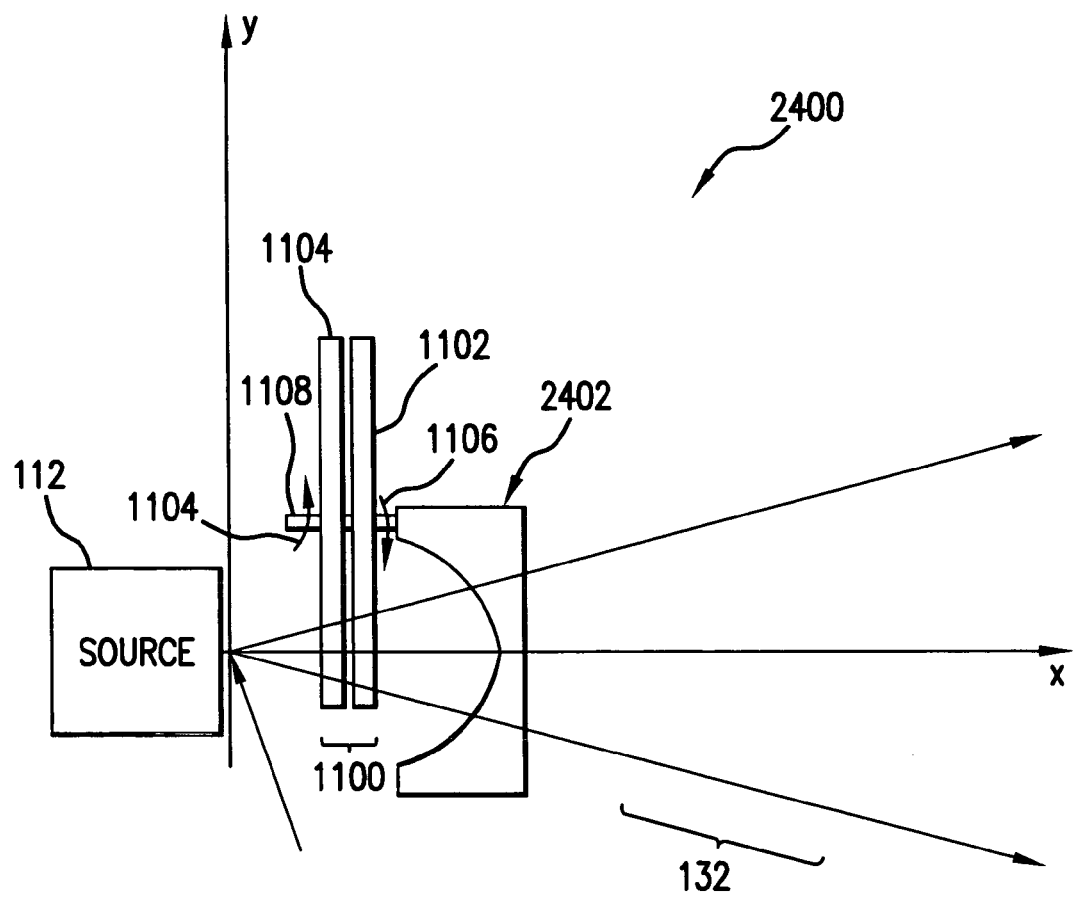
FIG. 24 shows the use of a dual wheel filter assembly in combination with a bow tie filter.

FIG. 24 shows a filtration assembly 2400 that is similar to that shown in FIG. 11, except an optional bowtie filter 2402 is additionally provided in paths 132 to heavily attenuate peripheral portions of the combined paths 132 for use in CT embodiments. A bowtie filter may be made, for example, of graphite, Teflon or aluminum. The profile of the bow-tie filter may vary along the z axis (not shown—parallel to paper) to provide either a plurality of discrete bow-tie filters or a continuity of variable path attenuations; such discrete or continuous variations being activated by a stepper motor advancing the bow-tie filter along the z-axis and in front of the x-ray source. As before, the filter wheels 1102, 1104 may be operated in specially selected combinations addressing different voltages and currents that tare applied to energize source 112. Accordingly, both kVp and filter materials waveforms may be optimized in a number of ways, so that a large number of spectra and imaging configurations are possible. Modern high-frequency X-ray generators and tubes allow peak tube kilo-voltage (kVp) to be switched, for example, from a low to a high setting, in the order of a few micro-seconds, such as (20 to 100 micro-seconds depending on design. Tube current (mA) variations also may be induced in a few milliseconds for rapid sampling speed.

Section B.2—Configurations for Line-integral Multiple Samplings

Figure 25A:
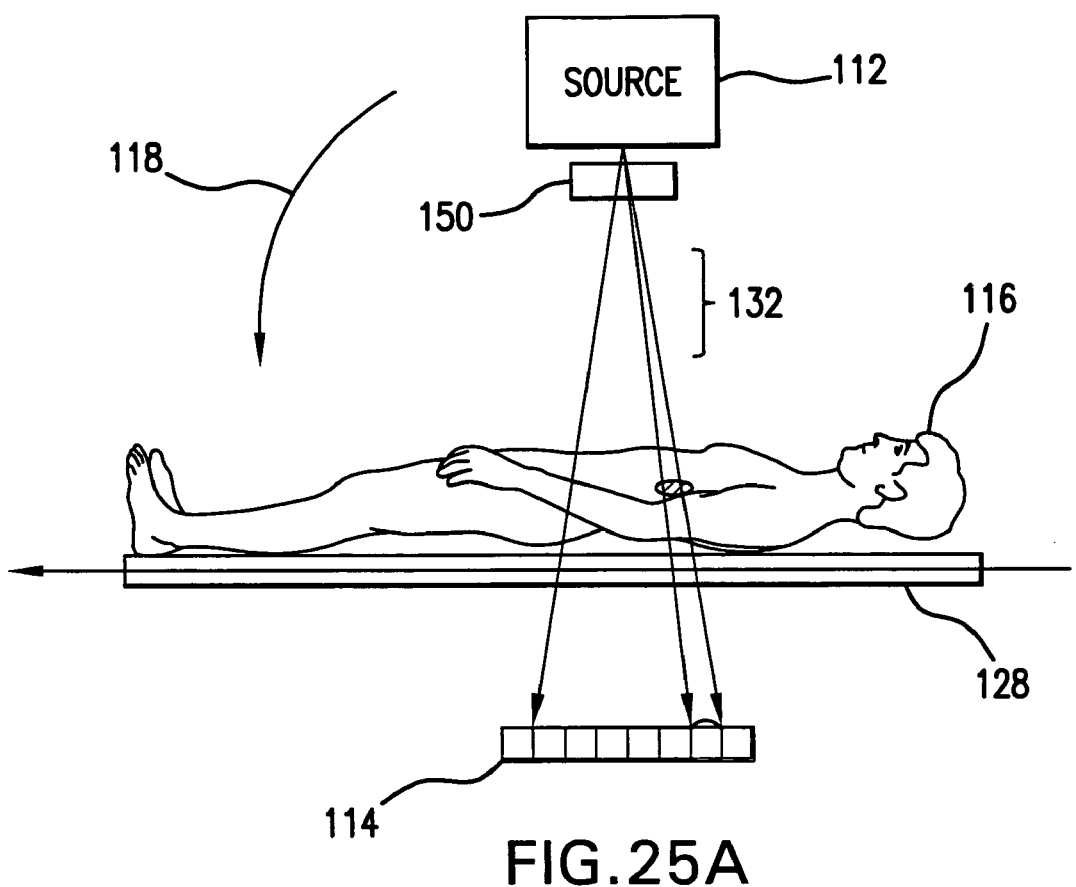
FIG. 25A and FIG. 25B show the projection of the same object volume of interest at two different spectra and at two different times, with the paths through the volume of interest corresponding to essentially the same line integrals.
Figure 25B:
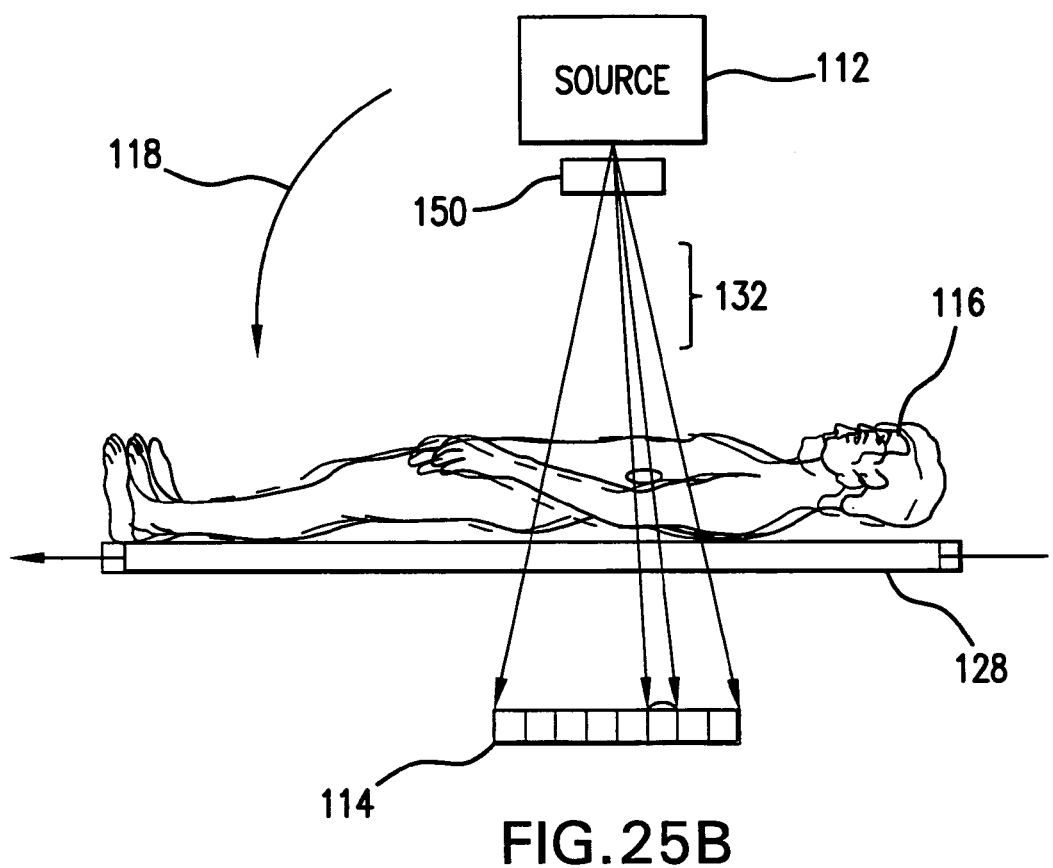

Several configurations are available for multi-spectral sampling of the same line integral in an examination time that precludes motion artifacts. In MDCT these are (a) Scout imaging and (b) helical scanning. Cone-beam effects are accommodated in protocol and reconstruction algorithm designs. FIGS. 25A and B show one of multiple sampling of a given line-integral through low-pitch helical scanning. This geometry corresponds to either "scout" scanning or line-integral sampling every rotation. These figures show how the projection of a given point of the interest through the patient projects onto one of the detector rows or row segments for one of the T measurements; after one half or full source rotation, the same body point of interest now projects onto another detector row or row segment. By iterating upon T measurements at M different spectra, M multi-spectral measurements of substantially the same X-ray path through the body are acquire in a single scan. As a result, T sets of projection data each sufficient for tomographic reconstruction of at least one slice through the body are acquired at a multiplicity M of spectra.

Section B.3—Cyclical and Pseudo-cyclical Spectra Selection

For continuous imaging of a volume of interest, the spectra may be repeated in a cycle. The cycle length depends on design and examination selections. In particular, the maximum number of spectra that can be separately detected on a particular slice of the patient under interrogation is given by the number of detector rows/columns and helical pitch. Trade-offs between the number of distinct spectra and the number of samples available can then be optimized on an application-basis to reflect constraints of noise, dose limitations, and helical scanning speed.

Rapid data processing allows adaptive selection of the techniques, such as kVp and mA, to reflect varying attenuation condition encountered along the body being scanned. Such an "automatic exposure control" approach may be used to adaptively change the range of imaging parameters that will be used to image a particular slice of the patient. As a result, the kVp, mA, filtration, and anode-track selection waveforms would become pseudo-cyclical.

B.4—Multi-spectral Data Decomposition

By relying on the selection of narrow, essentially non-overlapping spectra, (or alternatively using detector energy discrimination and photon counting) an estimate of the projection data is given in a number P of energy intervals. Although the intervals are not necessarily of equal width, for simplicity the discussion below will assume so. Formally, a given line integral measurement then represents an average (possibly a weighted average as discussed above) of the detected events over such discrete intervals. The linear attenuation coefficients of Q basis function materials are known as a function of energy over the spectra of interest, a given average attenuation coefficient being approximately obtained by integrating as follows:

$$M_i^j = \int_{E=0}^{E=kVp(\max)} \mu^j(E) \times rect\left(\frac{E-E_i}{\Delta E}\right) \times dE, \quad (1.35)$$
$$j = 1, \ldots, Q; i = 1, \ldots, P,$$

where rect( ) represents the usual function:

$$rect(x)=1; \; -\tfrac{1}{2} \leq x \leq \tfrac{1}{2} \quad (1.36)$$

$$rect(x)=0 \text{ otherwise.} \quad (1.37)$$

Accordingly, representing the Q basis functions (as measured at P energy intervals) in matrix form, the problem (in a linear approximation corresponding to equations (1.13) to (1.18)) is posed as:

$$[M]_{P \times Q} \times A_{Q \times 1} = D_{P \times 1}, \quad (1.38)$$

where M represents a matrix with P rows and Q columns, A is the vector of unknown decomposition coefficients (Q×1) (c.f. equation 1.17), and D (P×1) represents the data (for one line integral through the patient in the X-ray projection) as a function of the P energy intervals.

The decomposition is now formulated as an inverse problem. Formally, the solution to equation (1.38) is given by the pseudo-inverse (where $M^T$ represents the transpose of matrix M):

$$M^T A M = M^T D \quad (1.39)$$

and if the resulting matrix is non-singular:

$$A = (M^T M)^{-1} M^T D \quad (1.40)$$

This solution to the normal set of equations (1.38) provides the least squares solution (Strang, 1988). It is also well known that the singular value decomposition (SVD) of a matrix may be used to provide a regularized solution to the original problem. SVD is a powerful approach to problems posed with matrices that are singular or near singular (Press, 1999). Regularization is a known tool in alleviating issues associated with noise and inconsistencies in the projection data (Stark, 1987; Lagendijk, 1991).

The description above may be generalized to the case of P wide-band input spectra. In the general imaging case (with or without the use of energy-sensitive and photon-counting detectors), the projection data are weighted by spectra of various distributions. With proper input spectrum normalization, a photon counting and energy-discrimination approach would be treated just as described above. More generally a given projection measurement reflects a weighted average over a larger energy band (and overlapping spectra as typically obtained with a broad-band X-ray source such as a Tungsten anode), data are collected for P spectra($\Im_i$),i=1, . . . ,P. Each spectrum may be decomposed onto R energy intervals so that in a discrete representation (and assuming linearity):

$$\Im_i = (S_{i,1}, \ldots, S_{i,R}) \quad (1.41)$$

Accordingly each projection datum is given by:

$$d_i = \sum_{q=1}^{q=Q} a_q \times (\Im_i)^T M_q, \quad (1.42)$$

where $M_q$ represents the q-th column vector of matrix M (R rows and Q columns) introduced in (1.37). In matrix equation:

$$D_{P \times 1} = ([\Im]_{R \times P})^T \times [M]_{R \times Q} \times A_{Q \times 1} \quad (1.42)$$

If we now set:

$$M_{P \times Q}' = ([\Im]_{R \times P})^T \times [M]_{R \times Q} \quad (1.43)$$

then it is clear that the problem is again posed in the form (1.37) above, and the solution, i.e., decomposition onto known basis-functions, is obtained by inversion of the system (1.43). It should be noted that the Q basis functions might be given either by known elemental materials, such as given by the periodic table of elements. The basis functions may also be theoretically calculated or experimentally measured for known tissues, such as cancer types, or materials, such as iodine. Equation (1.43) reflects the assumptions of a linear model. Given the known (as a function of energy) Q materials onto which to decompose the linear-attenuation coefficients, it is clear that proper choice of the spectra-defining matrix $[\Im]$ will contribute to the matrix singularity. Numerical techniques are available to help select spectra (based on physics constraints) that will ensure that the matrix to be inverted is non-singular, or will reduce the degree of singularity (as measured for example by the number of singular values less than a given threshold). In a linear model it is possible to perform the image reconstruction for each acquired spectrum and then perform-the spectral decomposition on a pixel-by-pixel basis.

In a more general approach when the spectra may not be considered narrow-band, the linear approximation of (1.43) does not hold and it is necessary to return to a more general image formation model, such as that of equation (1.3). Inversion of this model, e.g., in the case of overlapping spectra, requires the use of iterative methods, but allows modeling of a-priori information and the representation of the X-ray quantum statistics. Given that often inverse problems deal with noisy data sets, such as those including X-ray quantum noise, or underdetermined data sets, much emphasis has been placed on statistical approaches, with inclusion of a-priori information into the model. For instance, in imaging a particular body organ with contrast medium, the presence of iodine in some of the anatomy may-be known beforehand. Thus, a-priori information may also take the form of constraints on the decomposition coefficients, such as spatial constraints. By way of example, a spatial constraint may be related to the decomposition coefficient rate of change from one line-integral (pixel) to its neighbors. Methods that may be applied include Bayesian approaches such as maximum a-posteriori. Practical approaches to solve such problems include various maximization methods, such as simulated annealing (Geman, 1984), use of concave surrogate functions (Ortega, 1970; Fessler, 2000), and many other numerical approaches (Press, 1999). In such a non-linear model, the spectral decomposition will be performed on the projection data; each decomposed data set will then be reconstructed in a cross-sectional image.

Section B.5—Limited Angle CT Image Reconstruction

Availability of even a few projections of a given object has been shown very effective in providing information about the low frequencies of the object. In particular, the low frequencies of the object projection vary very slowly from projection angle to projection angle (Besson, 1999). Indeed, it is well known that the DC component of the object may be determined directly from a single projection. Accordingly, measurement of even a few projections (as, for example, along the target of an electron-beam CT system) contributes significant tomographic information (Besson, 2000). It has been shown that using a finite source segment of a straight line, it is possible to reconstruct images with quality comparable to those obtained when the source points are distributed along a circle (Smith and Singh, 1993).

Beyond acquisition of a few projections, the design of system 100 may allow reconstruction of a tomographic image with image quality properties equal to or superior to those of conventional computed tomography systems. These systems include those using acquisition of a multiplicity of projections with the source focal spot describing a circle or arc of a circle around the body to be imaged. Although in a practical implementation the length of the target is necessarily limited, it is possible to obtain exact tomographic reconstruction from source data extending on an infinite straight line past the object being imaged. It is clear that projections acquired past a given dimension contribute only marginal additional information, and so it is useful and efficient to limit the projection length. Therefore, an approximate tomographic reconstruction is possible from data acquired on a limited linear source trajectory.

Iterative image reconstruction approaches offer advantages as compared to filtered-backprojection for limited-angle situations. In particular, a-priori information as well as specific image chain model information may be included in iterative approaches to yield improved image quality.

Multiple configurations are available for multi-spectral sampling of the same line integral. Here the term "multi-spectral" may mean either of overlapping or non-overlapping spectra, and/or use of photon-counting and energy discriminating detectors. The following examples demonstrate how this disclosure may be carried out. The goal is to achieve multiple sampling of "essentially the same line-integral" of the object under consideration, in an examination time that precludes motion or other artifacts. The term "essentially the same line-integral" includes cases where it is recognized by the person skilled in the art that some minor, second-order variation in the exact analytical expression of the line-integral may exist, but such differences are secondary to the characterization/imaging goals. Such secondary effects include limited cone-angles, such as in multislice CT or projection X-ray imaging. The synchronization of data acquisition, table or source-detector assembly advance (motion), and spectra selection is key to an effective implementation of the disclosure.

Figure 26:
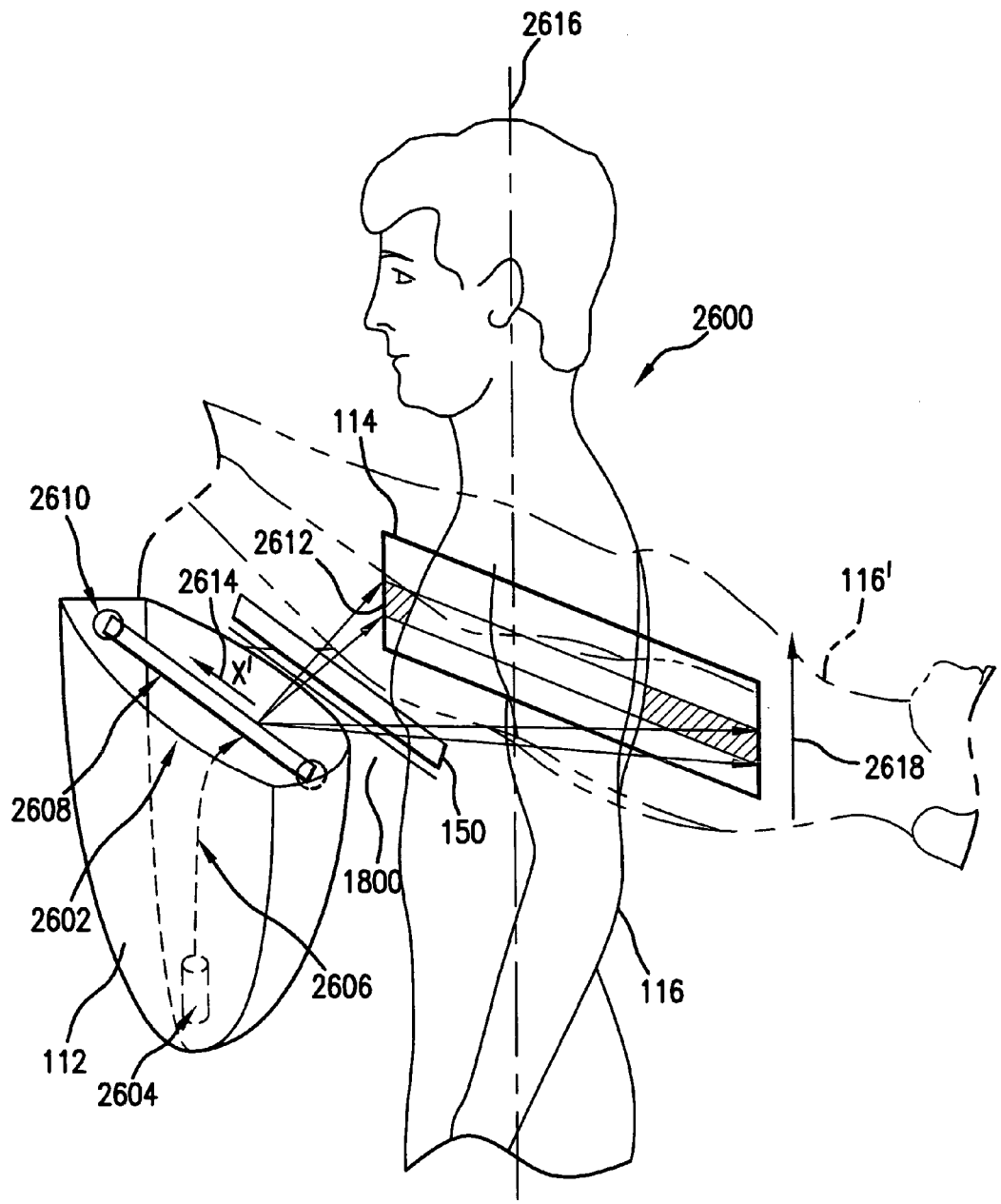
FIG. 26 shows use of an under-collimated beam in an imaging system that includes an electron-beam x-ray tube in a vacuum envelope and the use of a fixed or rotating tube target (anode)

Section B.6—Projection and Volumetric Limited-angle Multi-spectral Tomographic Imaging with an Electron Beam System FIG. 26 illustrates one implementation of system 100 as an up-right multi-spectral limited angle electron-beam X-ray imaging system 2600. Source 112 contains a vacuum envelope or housing 2602 that holds an electron gun 2604 capable of directing an electron beam 2606 to target anode 2608. The electron beam 2606 may be internally processed by conventional electron optics (not shown), such as various focusing electrodes and ion-clearing electrodes. The anode 2608 may be stationary, or may be rotated by a rotor/stator mechanism 2610. A pre-patient collimator 1800 defines the beam on the electron-beam side of the object to be imaged, so that a fan-shaped X-ray beam is emitted from the electron-beam instantaneous focal position to the detector on paths 132. The beam covers several rows 2612 of detector array 114, but not necessarily the entire detector dimension with respect to the direction 2618 orthogonal to the scanning direction 2614. The collimator and detector assembly may be rigidly connected by an arm (not shown). As the electron beam is deflected along the x' axis, a multiplicity of projections are acquired. The beam position along the longitudinal axis of the body 116 may be further defined by angulation or rotation of the anode 2608. Vector 2618 defines a relative motion of the body 116 as compared to the detector array 114.

System 2600 allows multi-spectral data acquisition at a multiplicity of projection angles for each slice with respect to the long axis orthogonal to the electron beam scanning direction of the body to be imaged. Tube focal position variation of a few degrees allows image reconstruction, via such methods as tomosynthesis or limited-angle computed tomography (CT) image reconstruction, of various planes in the body to be imaged. Experience with limited-data reconstruction confirms that image low and mid-frequencies are very well estimated from a few projections (Besson, 1999a; Besson, 1999b). This facilitates fast multi-spectral limited-angle CT imaging of a body.

Although FIG. 26 illustrates the system 2600 for relative scanning direction of the patient/object with respect to the gantry (image chain) along the long axis of the body 116, it is clear that a similar system could be designed such that the scan occurs laterally across the body, for example, as shown by the position of body 116'. The orientation of body 116 or 116' may enhance or facilitate discrimination of specific features, such as lung nodules or cancerous tumors, and acquisition of a multiplicity of views along a particular axis may be further advantageous. Lateral scanning may also take place on an up-right system. A variety of other geometric configurations are also available. For example, a longitudinal scanning system may be designed for use in conjunction with a patient table where the detector is scanned below the patient, or alternatively in such a geometry the detector may remain fixed and the object to be imaged may be advanced along the axis, such as by a conveyor belt system for a luggage inspection device.

The electron beam-target anode 2608 is generally an anode of a material that emits the X-ray spectra. Anode 2608 may be stationary or may be mounted on a cylindrically shaped rotatable core. Rotation of the target presents controllability advantages in terms of target heat loading. This disclosure describes a novel X-ray tube technology for improved X-ray imaging with applications to medical imaging, homeland security, and industrial inspection. The technology described will support various imaging modes including multi-spectral single-scan limited-angle computed tomography (CT) and phase contrast imaging. The novel X-ray tube approach allows: (1) increased duty-cycle and lifetime; (2) moving the X-ray focal spot along a target for acquisition of a multiplicity of X-ray projections of a given object (limited-angle CT); (3) alternating target materials for dynamic multi-spectral data acquisition; (4) acquiring multiple samples of the object line integrals at a multiplicity of dynamically and adaptively selected X-ray techniques; and (5), acquiring multiple samples of the object line integrals with various focal spot sizes and parameters.

In an imaging system application, a multi-target tube may provide increased scan speeds; improved sensitivity to findings, such as detection of suspicious tissues or objects; and improved specificity in the characterization and classification of suspicious findings. A multi-target tube may facilitate limited-angle tomographic imaging and image reconstruction with image quality similar to that of a CT system. This disclosure also describes a means to perform a multi-energy imaging and analysis of a body in a single examination scan. It describes configurations for limited-angle CT imaging in a multi-spectral approach. It further describes how methods of limited angle CT image reconstruction may be combined with multi-spectral data acquisition to obtain tomographic data on a multiplicity of basis-function decompositions.

Target surfaces may be disposed in such a manner as to allow continuous rotation of the target anode ("cylinder"). In such an arrangement, the surface geometry of each segment is designed to allow continuous anode rotation at a fixed rate while presenting the electron beam focal spot at an essentially fixed angle with respect to the detector (for a given electron beam scanning velocity). This focal-spot angle may then be adjusted by changing the phase between the electron-beam scanning waveform and the anode rotation waveform. The scanning period in one direction on the target is typically of the order of a few milliseconds. After beam retrace (during which time the electron beam is directed to a beam stopper, not the anode), the electron beam is redirected to the beginning of the next target segment, thereby allowing heat dissipation in the previous segment as well as possible selection of a new spectrum (via X-ray techniques (generator peak kilo-voltage (kVp), tube current (mA)), filtration, and anode target material). Alternatively, the surface of a cylinder of appropriate diameter can be used directly to deposit the target materials; in such a geometry, the relative timing of the sweep and rotation phase is not a important as in the multi-facet case. Alternatively, the target may be stationary and may comprise one, two, or more target segments made of different materials with properties appropriate for x-ray imaging. Therefore this tube and system design presents unique advantages for practical implementation of a multi-spectral limited-angle tomography system.

Figure 27:
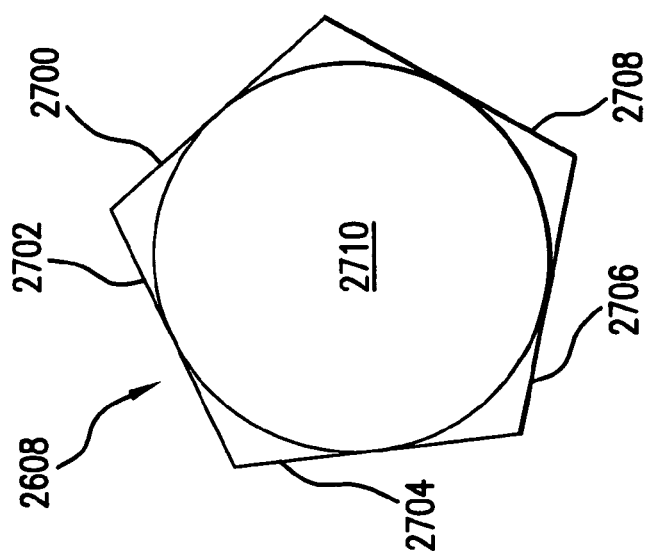
FIG. 27 shows a multi-faceted target for use in an X-ray emission source.

FIG. 27 is an end view of showing one possible embodiment of anode 2608 representing a multi-target anode design. Facet surfacings include targets 2700, 2702, 2704, 2706, 2708, which are mounted on a cylindrical hub 2710 that may be rotated by the rotor/stator mechanism 2610 (see FIG. 26). This rotation occurs under control of computing equipment 122, such that for a given electron-beam scanning velocity and a given anode angular velocity, the instantaneous focal spot position of electron beam 2606 on a selected one of surfacings 2700–2708 is substantially at the same angle determined with respect to the desired travel of the primary X-ray beam axis on paths 132. Besides assuring constant imaging focal spot geometry with respect to the patient and detector, this design allows improved heat capacity by distributing the heat onto the various target segments. The surface targets 2700–2708 may each be formed of different target materials, such as Tungsten on target 2704 and Rhodium on target 2708, or alloy compositions.

Figure 28A:
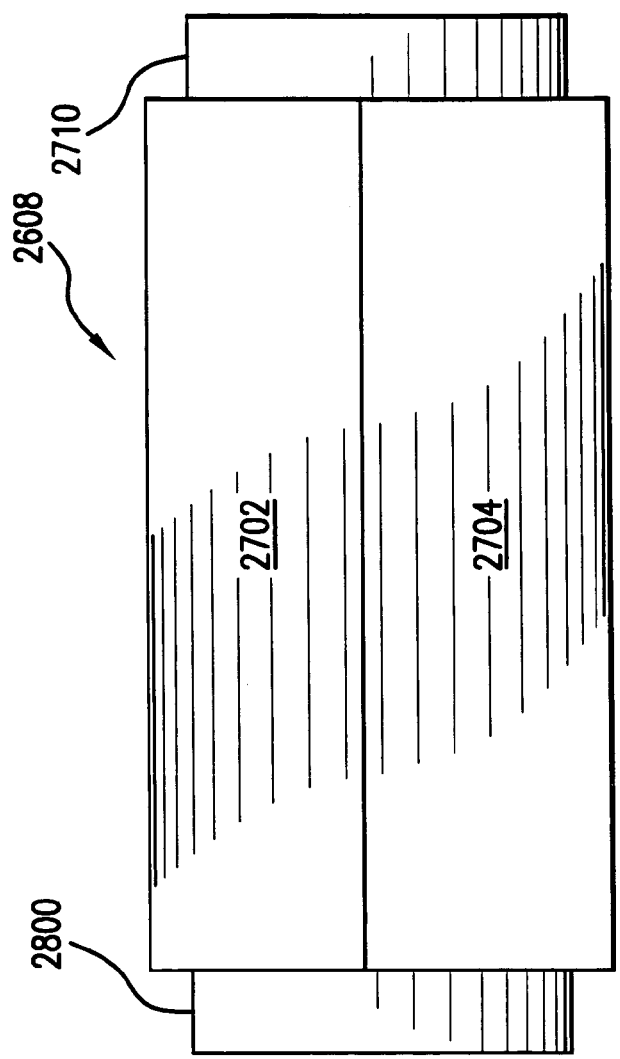
FIG. 28A provided additional detail with respect to the target.
Figure 32:
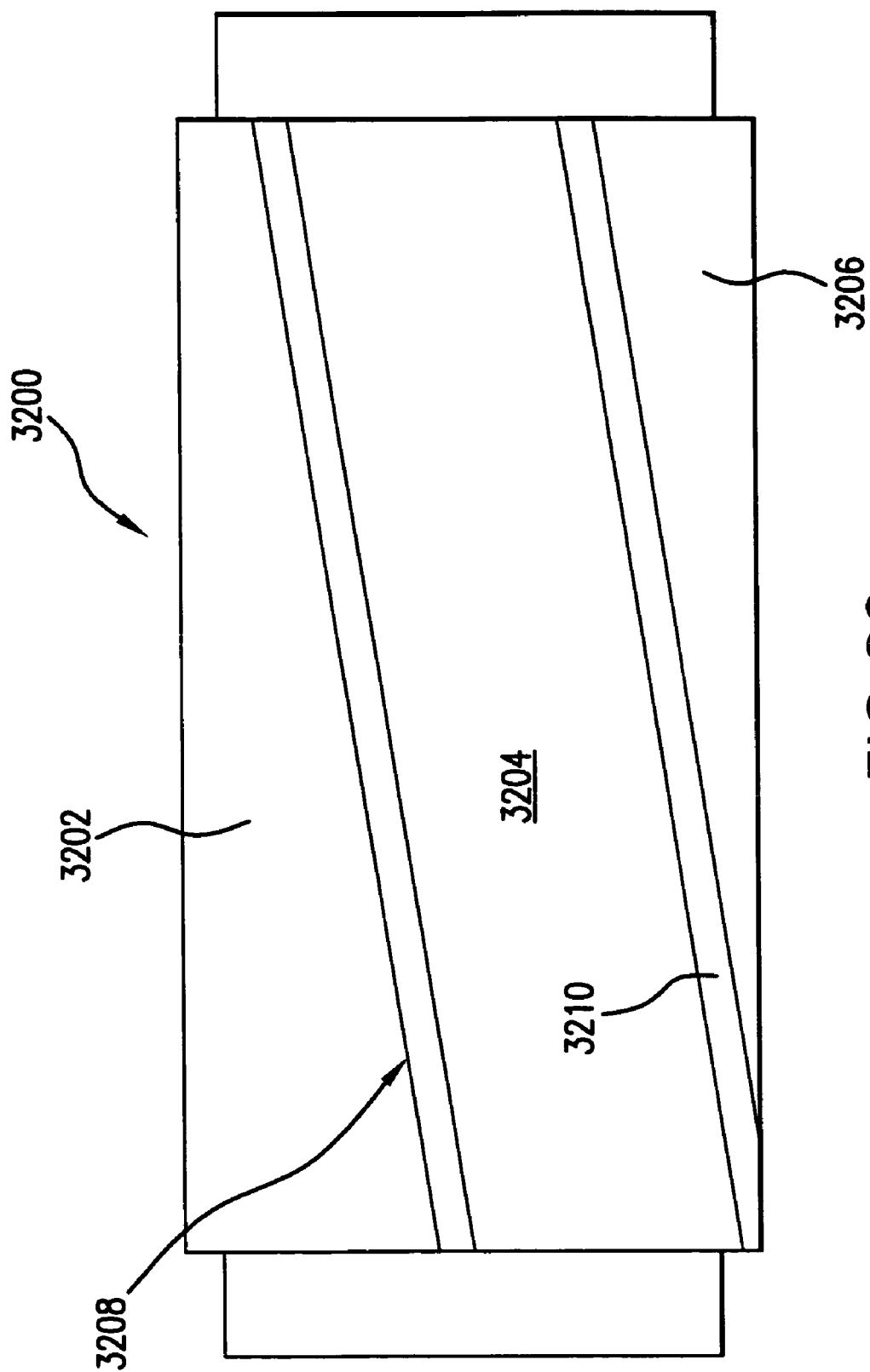
FIG. 32 shows an additional embodiment for the multi-source target including channels or grooves that may be used for cooling purposes, and illustrates the use of slanted target surfaces.

As will be shown below, for example, in context of FIG. 32, and also in context of FIG. 28A through FIG. 28C, the electron beam 2606 may target a multifaceted anode where the anode has various target materials on planar facets, and the incident angle of the electron beam 2606 may be precisely maintained or adjusted with respect to the angle of the electron beam striking the planar surfaces. FIG. 28A shows a side elevation view of anode 2608 confirming targets 2702 and 2704, and showing a second hub 2800 positioned remotely from hub 2710.

Figure 28B:
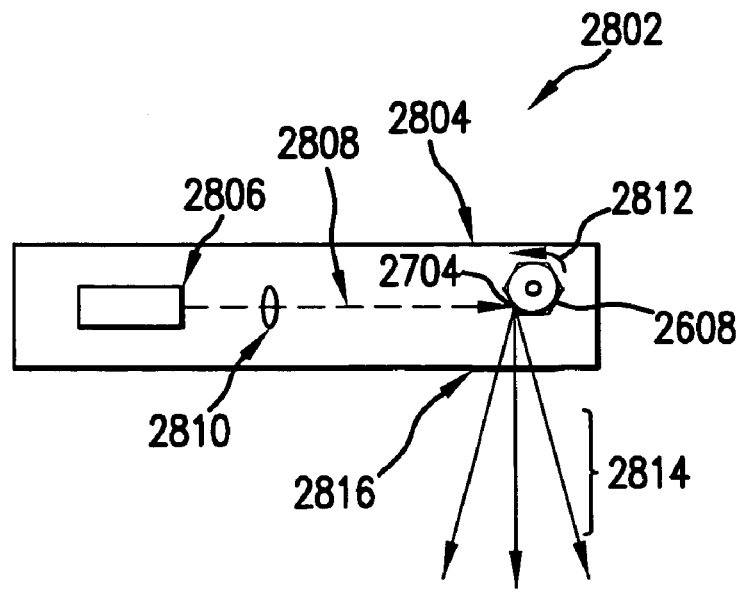
FIG. 28B shows the multi-spectral target in use within an electron-beam X-ray source assembly.
Figure 28C:
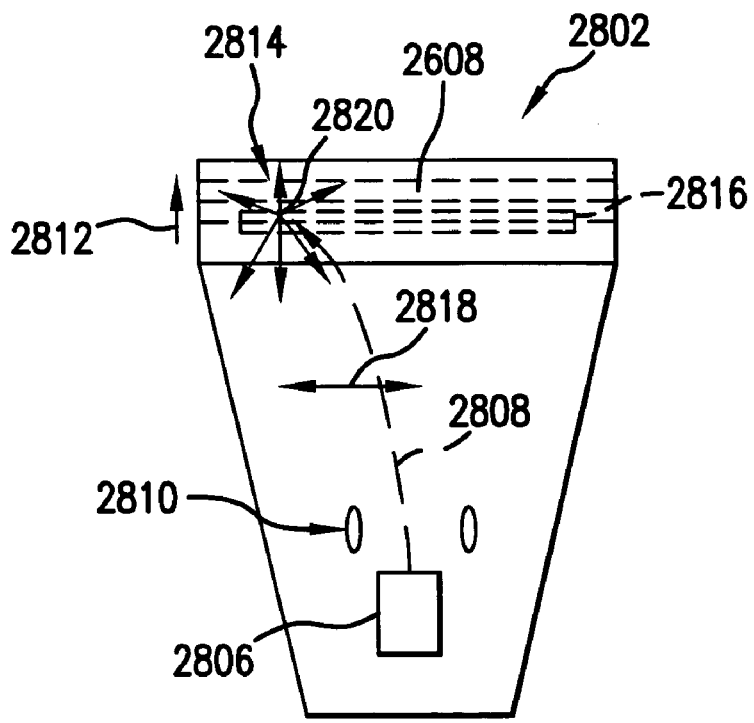
FIG. 28C provides additional information with respect to electron beams steering within the X-ray source assembly.

FIG. 28B shows a midsectional side view of source 2802, which may be used as source 112. Anode 2608 is installed within a vacuum envelope 2804. An electron gun 2806 emits an electron beam 2808, which is directed towards anode 2608 by steering electrodes 2810. As the anode 2608 (and associated targets) rotates according to arrow 2812, the electron beam 2808 impinges upon the targets, e.g., target 2704 of anode 2608 to emit X-rays on path 2814 through tube port 2816. FIG. 28C provides additional detail to show that the steering electrodes 2810 may drive consecutive sweeps the electron beam 2808 along sweep path 2818 to generate the X-ray beam 2814 at a continuum of locations along the anode 2608. The point or area of impingement 2820 of the electron beam 2808 on anode 2608 may be referred to as the focal spot.

By intrinsic design, the anode 2608 provides multiple target surfaces, each being swept by the focal spot 2820 in turn as a result of the rotation 2812. By way of example, anode 2608 may present one of targets 2700 to 2708 per unit time or per Δt, e.g., at a design of 10 ms per target presentation according to rotational velocity. Typical CT imaging systems allow for source motion of ~4-mm assuming a 650-mm source-to-isocenter distance, which permits 1000 imaging views per rotation. Allowing a design factor of two for source-motion blurring, or as with pulse sampling, allow for ~8 mm/view. In the aforementioned tube-target design, this translates into a sweep speed of ~16-mm/ ms at Δt=0.5 ms. For comparison, a 4" anode rotating at 3,600 RPM, with the focal track center at r=40-mm, leads to a focal-spot velocity with respect to the target of ~15-mm/ ms. One commercially available scanner, the EBT made by Imatron, has a target length of 2,800 mm, which may be covered in high-resolution mode by a 100-ms sweep. Accordingly, in that system, the focal spot linear velocity is about 30 mm/ms, which accommodates up to 1,000 mA tube current. For comparison, the tube design illustrated in FIGS. 28A to 28C permits a sampling time of Δt=0.25 ms to allow a linear focal spot velocity of 30-mm/ms, similar to the Imatron EBT. A target length of 300-mm would be scanned in 10 ms and provide about 40 views for limited-angle CT reconstruction or tomosynthesis.

Using the numbers above, for a target length of 300-mm, and M sections on anode 2608, the angular rotation time is N×10 ms per rotation. For example, M=6 leads to: 60-ms/ rotation, or 1,000 RPM, which is a relatively low rotation speed. This rotation speed can be slowed down by increasing the number of facets on the anode surface. Such a low RPM contributes to increased bearings and tube life.

Using N=6 and a 300-mm anode length, 1,800 mm of focal track are available for imaging under the above assumptions. For comparison, a large 10" anode would provide less than 700-mm of focal track. Table 9 provides various design parameters that are obtainable as variations on the foregoing assumptions.

TABLE 9

Target design parameters.

|  | EBT | 4" anode | 7" anode | Multi-target design (300-mm) |
|---|---|---|---|---|
| Focal-spot sweep speed | 30 mm/ms | 16 mm/ms | 86 mm/ms | 15 mm/s (at 0.5 s sample) |
| RPM | NA | 3,600 | 3,600–10,000 | 1,000 |
| Track length | 2,800 mm | 280 mm | 520 mm | 1,800 mm |
| Maximum mA | 1,000 | 250 | 500 | 500–1000 |

Target design may accommodate focal spot sizes ranging from a few (10) microns to 1.0 mm or higher, depending upon the intended environment of use. For a 70° angle, which is commonly used in CT applications and accounting for a NEMA tolerance of 100%, the minimum target width is: 16.3 mm. Using 20-mm, and N=6 segments, the approximate outer circle defining the anode cross-section is about 55 to 60-mm in diameter.

Several design solutions are available for the composition of anode 2608. For example:
  (1) Standard Metal: The material for a given focal track or sector of material, for example, Tungsten 90% and Rhenium 10%, is layered onto a titanium zirconium molybdenum substrate;
  (2) Brazed Graphite: This may be installed over a graphite backing. Graphite does not transfer heat quickly, but has a high storage capacity; and
  (3) CVD graphite target: Target material is deposited onto a high purity graphite substrate. This design is light and has good heat storage, but low focal spot loading due to lack of heat dissipation.

Possible target materials for use as sectors on anode 2608 include Tungsten, Rhodium, Molybdenum, and other high-Z materials, such as U, Pb, Ta, Hf, Pt, Au, Ti, Zr, Nb, Ag, U, Co, and Cu. High Z materials are generally those known to be more effective for X-ray production.

System design generally accommodates a principle that more than 99% of the energy in electron beam 2808 is transformed into heat. Using parameters of 140-kVp and 500 mA, the power input to the target is about 70 kWatts. A 6-second scan leads to a deposition of about 420 kJ.

Figure 29:
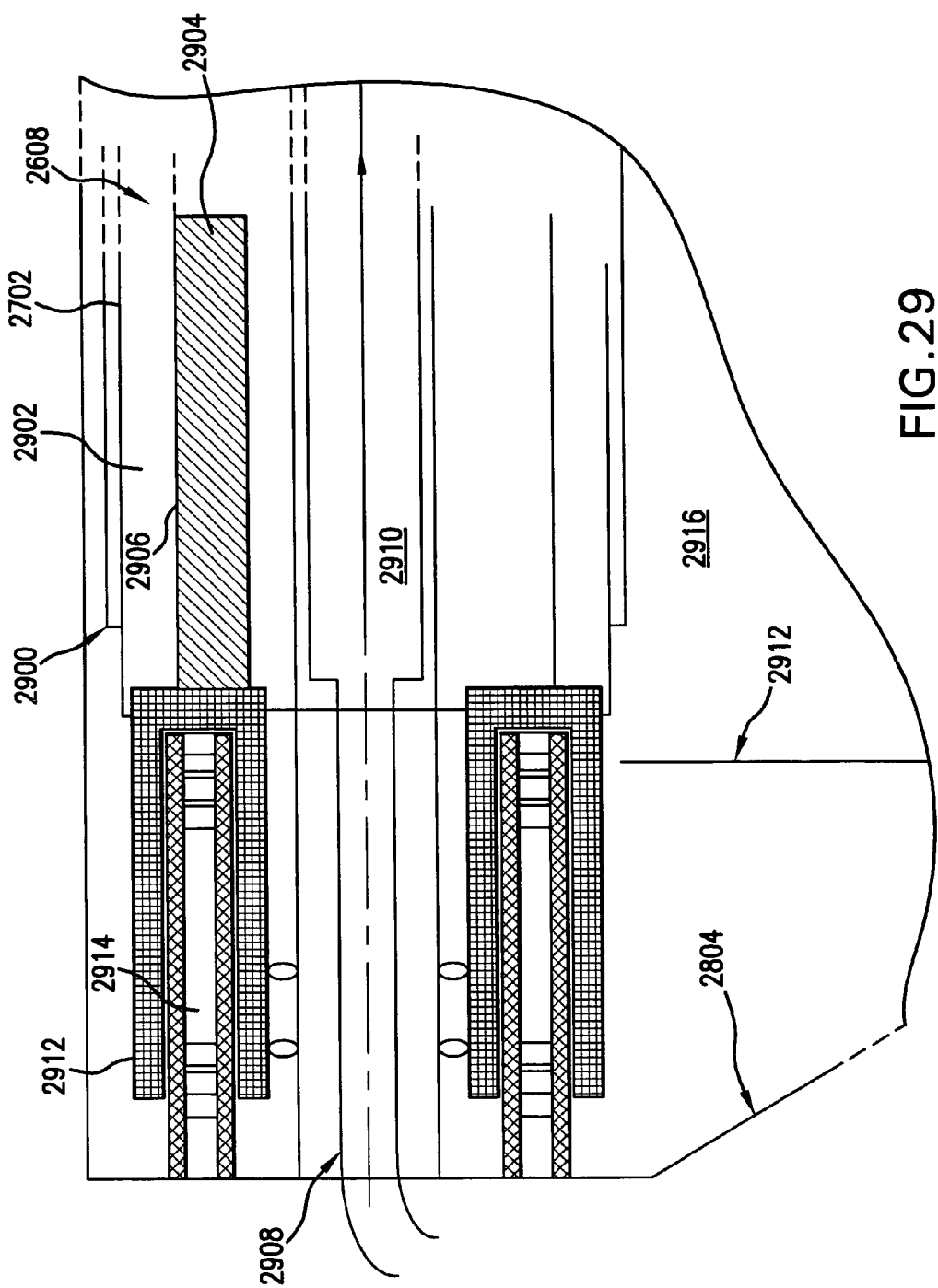
FIG. 29 provides additional detail with respect to construction of a multi-source target, according to one embodiment, to provide active internal anode cooling.

FIG. 29 is a partial midsectional view that shows one embodiment to provide internal active cooling for the anode 2608. The respective sectors are provided with target material, for example, as target 2702 is formed of target material 2900 atop a conductive substrate 2902. The target material 2900 may be any target materials, for example, as described above. The substrate may be, for example, TZM as described above. A plurality of strips, such as strip 2904 may be high-heat storage materials, such as graphite. Strip 2904 may be brazed to the internal surface 2906 of substrate 2902 to establish superior stability in rotation and improved heat transfer. The volume of strips 2904 may be selected for a particular use as an optimum design trade-off balancing heat transfer and heat storage capacity. A cooling circuit or passage 2908 is provided to circulate a coolant 2910 for heat dissipation purposes. The passage 2908 may extend centrally through race bearings 2912 and stator windings 2914. Passage 2980 is in contact with the outside surface of the vacuum envelope 2804 (not shown) for coolant circulation. An electromagnetic shield 2912 blocks transmission of radiation from cavity 2916.

Figure 30:
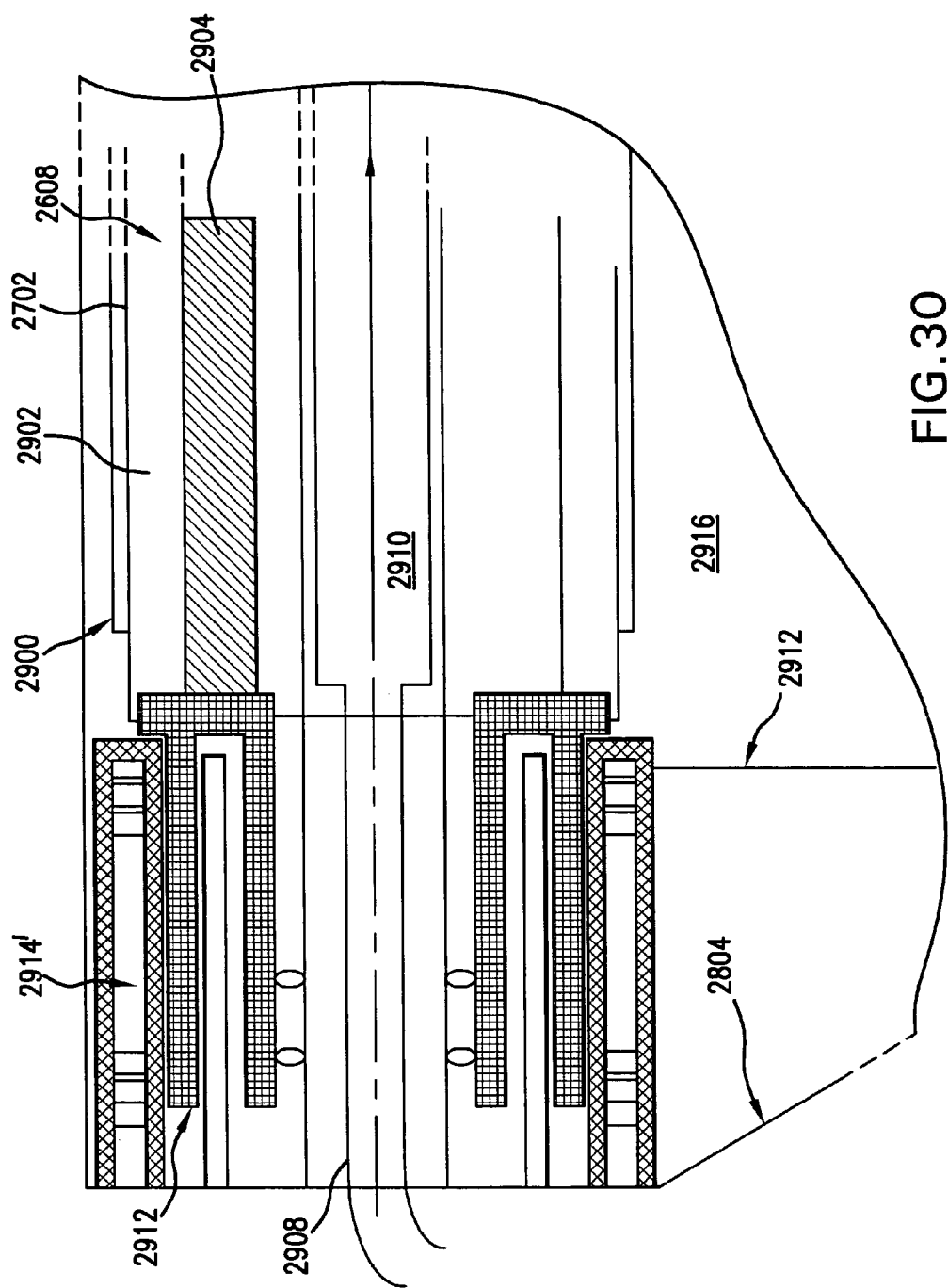
FIG. 30 provides additional detail with respect to construction of a multi-source target, according to one embodiment.
Figure 31:
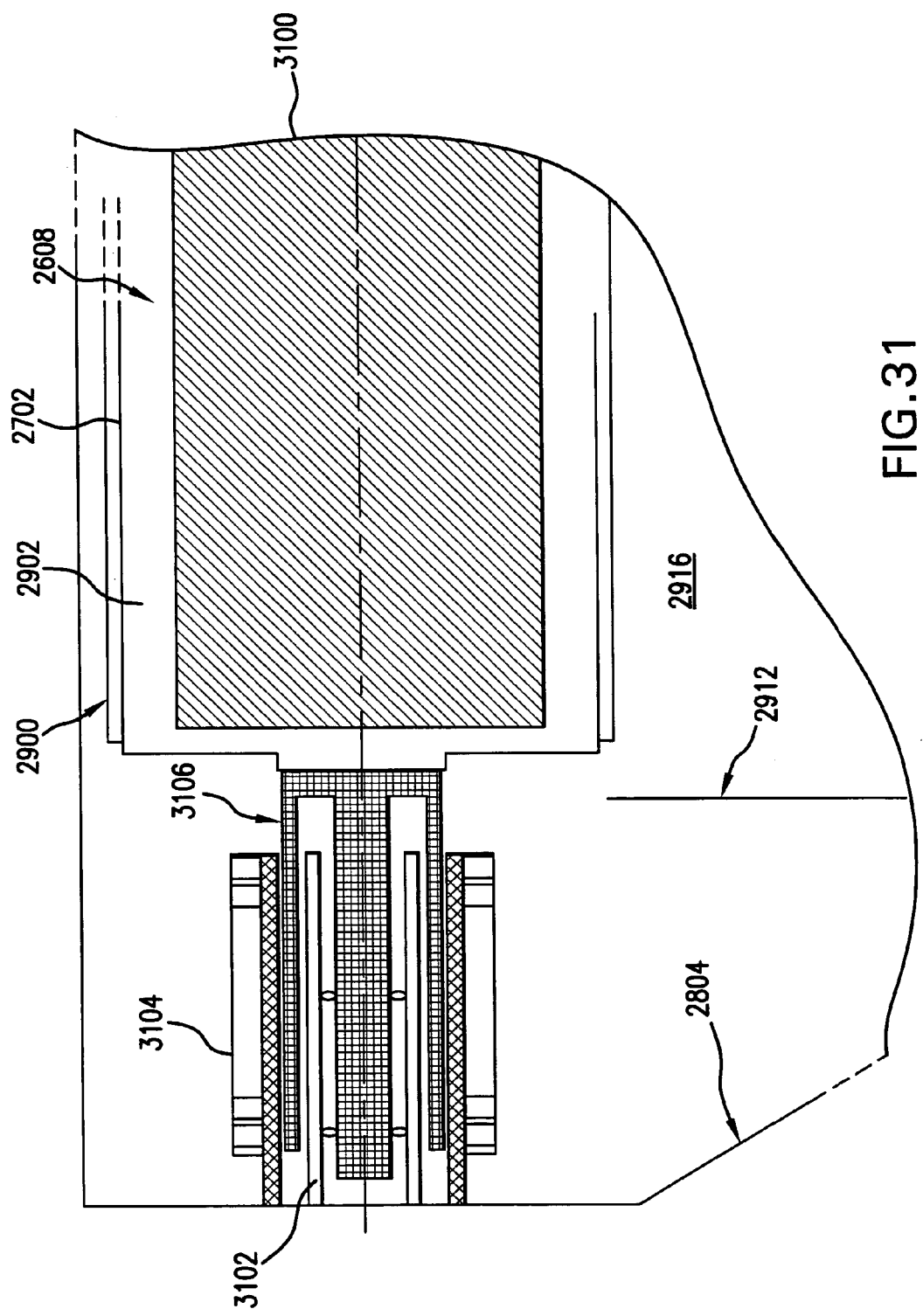
FIG. 31 provides additional detail with respect to construction of a multi-source target, according to one embodiment.

FIG. 30 illustrates an alternative embodiment that is identical to that shown in FIG. 29, except the stator windings 2914' are located at a radially outboard position with respect to race bearings 2912. FIG. 31 illustrates an alternative embodiment without internal cooling where a large central graphite core is centrally positioned internal to substrate 2902. Stator windings 3104 are located centrally with respect to armature 3106. By way of example, a large CT tube (7") with graphite backing can provide up to 5,000,000 HU anode heat storage. Using a 2" graphite depth for illustration, the total volume of graphite is 1.2 L. A 300-mm long anode with a 100-mm diameter would provide a volume of up to 2.3 L available for graphite inside the anode cylinder (0.85 L at 60-mm diameter). Accordingly, the tube heat storage capacity can be made to be twice larger than that of the largest CT tubes available on the market.

As shown in FIGS. 28 and 29, the rate of heat dissipation may be increased by using a cooling passage 2908 internal to the anode 2608. FIG. 32 illustrates an alternative target 3200 in which he respective target sectors 3202, 3204, 3206 are separated by cooling channels 3208, 3210 to facilitate dissipation of heat away from the target 3200.

The race bearings 2912, 3102, may be dual axis bearings, i.e., one on each side of anode 2608 at hubs 2712, 2800. This may decrease vibrations. In combination with the low target RPM (for example <1,000 RPM depending on sweep speed and target diameter),this may increase tube life and allow for very high duty cycles. Most bearings should not be operated at temperatures greater than 300 to 500-degrees Celsius, which is a limit generally imposed by lubricant failure. Specific materials are used in the composition of the target stems or hubs 2712, 2800 to prevent heat from reaching the bearing assembly and raising the temperature to such a point that target life is impaired. Use of emissive coatings on the target may be effective in preventing heat transfer from the anode to the bearings.

In a design using an internal active cooling, the weight of the target 2602 of a given length may be minimized by reduced substrate material thickness to improve heat transfer through the active cooling apparatus and circuit. This reduced weight combined with the low rotation speed may contribute to effective target life or duty cycle.

A metal vacuum envelope 2804, rather than glass, provides longer tube life, reduced off-focal radiation through grounding of the envelope, reduction in tube—spits, and elimination of arcing.

A typical vacuum requirement for an electron-beam X-ray tube envelope is of the order of $5 \times 10^{-8}$ Torr (space charge mode); and $10^{-6}$ to $10^{-5}$ Torr under ion-focused mode (in this mode, a gas is deliberately introduced into the vacuum chamber).

A line-of-focus principle may be used to increase the surface area struck by the electron beam 2808 without increasing the apparent size of focal spot 2820. In radiography applications, the target angle is about 20-degrees, while it is typically 7-degrees in CT applications. In this design, the target angle may be adjusted by changing the phase of the electron beam sweep wave-form with respect to the anode angular rotation. It may be desirable to include an encoder and feedback loop mechanism (not shown) to fine-tune the anode rotation and ensure that the rotation phase remains in a specified relationship with respect to the electron beam sweep cycles. Alternatively, the anode rotation phase information may be fed-back to the electron-gun and electron optics to synchronize the two waveforms based on electron-beam controls.

Section C.1—Scatter

Scattering may occur by Compton or Rayleigh phenomena. In Compton scattering x-rays are deflected from their original direction and lose energy in the interaction (the energy loss depends, among other factors, on the scattering angle).

Scattered radiation summed to the primary radiation (and not identified as scattered energy) contributes only noise to the image formation process. Accordingly, means of subtracting the scattered signal from the primary, or of discriminating the scattered radiation, improve image information first by reducing noise, and, in specific situation, by providing additional information with respect to the tissues or objects that generated the scatters. Compton discrimination is useful, for example, as an aid to computer assisted diagnosis where diseased tissue has a different composition from surrounding tissue, such as is the case with metastasized cancer or calcareous growths. Scatter detection is facilitated by the use of a narrow, undercollimated beam geometry.

Compton radiation may be recognized as such on the basis of a photon energy lower than that of the primary radiation in the spectral band of interest. In chest imaging, coherent (Rayleigh) scattering is a proportionally higher projection component for bone and mediastinum structures. Rayleigh scattering is predominantly forward directed and contributes a larger component to the detected signal in the rows/columns directly adjacent the primary beam projection. Farther away from the primary beam, Compton scattering is usually dominant. Both types of detected events may be leveraged to improve upon tissue characterization (Barrett and Swindell, 1981; Davidson et al., 2002).

Multispectral X-ray scatter imaging and analysis combines the elements of energy decomposition, as described above, with the use of scattered radiation for further identification and characterization of materials and tissue. More particularly, by utilizing an under-collimated beam in a narrow-beam geometry coherent scatter imaging and energy decomposition may be combined to achieve superior tissue and material characterization. In the frame work of a narrow-band input spectra decomposition, or when using a broad-band input spectrum in combination with photon counting and energy discrimination, this disclosure describes how Compton scatter detection and analysis contributes to improved material or tissue characterization.

In the framework of the x-ray measurement model given by equation (1.18), additional constraints may be imposed that increase the number of measurements available per line integral For instance, the length of the line-integral may be determined in X-ray modalities where compression is applied, or from a simple segmentation of a reconstructed CT image. In any CT image of the body, there is a sharp CT number jump from air at about −1000, to soft tissues at about 1000, or bone at up to 3000. These CT numbers use a definition based on a 1000 multiplier. In such a case, the linear system of equations (1.10) becomes:

$$P_i = N(E_i) \times E_i \times \exp\left\{-\sum_{r=1}^{R} \alpha_r \times \mu_r(E_i)\right\} \quad i = 1, \ldots, M \tag{1.44}$$

subject to (s.t.):

$$\sum_{r=1}^{r=R} \alpha_r = L \quad (1.45)$$

where L denotes the length of the line integral under consideration. This results into a system of M+1 equation, with potentially allows solving for M+1 unknowns. Additional constraints may also be imposed, such as lower and upper bound of the line integral, based on the an a-priori knowledge of the tissue or material interrogated (for example, from prior X-rays, it may be clear that the patient does not have any metal (clips, bullets, etc) in his or her body. In computed tomography, at least with the projection problem reformulated over parallel projections, it is well known that the total integral over the 2D plane of the line attenuation coefficient is a constant from projection to projection. Other constraints maybe derive in the context of CT, such as by considering the derivatives of the line integrals.

When used in combination, energy discrimination and spectral basis functions facilitate calculations to refine the line integral estimates, for example, to compensate for Compton scattering which is predominant above 50-keV and occurs with loss of energy to introduce a bias in the line integrals. Use of narrow beam spectra may assure that detected photons with an energy lower than that of the narrow beam are rejected as scatters, or may be analyzed separately from the primary beam data. Accordingly, scatter rejection is significantly enhanced in the combinative approach.

Some modifications to the foregoing equations may be made considering an energy interval of width ΔE. Although in projection imaging, 3D information might not be available regarding the subject composition, so that in a first approximation, and retaining the effective energy of the beam for the energy interval ΔE described above, equation (1.2) may be replaced by:

$$P = I_0 \times \exp\left\{-\int_{path\,L} \mu(l, E_{Eff}) \times dl\right\} \quad (1.46)$$

Knowledge of the path length, lgth(L), such as obtained from segmentation of the reconstructed image in CT, or through a compression device in mammography, or through a positioning device in radiography, leads to the following estimate for the linear attenuation coefficient at the effective beam energy:

$$\bar{\mu} = -\frac{1}{lgth(L)} \times Log\left(\frac{P}{I_0}\right) \quad (1.47)$$

The linear attenuation coefficients at diagnostic X-ray energies are given by the following equation:

$$\mu(l, E) = \{\mu_C(l, E) + \mu_R(l, E) + \mu_{PE}(l, E)\} \quad (1.48)$$

where the subscripts C, R, and PE stand for Compton, Rayleigh, and Photo-Electric respectively. The two first terms represent scattering of the impinging primary X-ray, while the photo-electric effect leads to the complete absorption of the X-ray and local energy transfer to the lattice/tissue structure. X-rays may be scattered once as single scatters, or multiple times in the subject under interrogation, and as is now described single scatters carry significant information about the local interaction site. Due to the stochastic nature of scattering, multiple scatter events do not carry information that is easily leveraged. Accordingly, in this invention disclosure means to estimate the multiple scatters will be described, so that following subtraction of the corresponding term, detected events correspond either to primary radiation or single scatters.

The single scatter analysis is first conducted for the Compton phenomenon. The collision cross-section $\sigma^C$ determines the probability that an incident photon will undergo a Compton scatter. In a thin layer of thickness dx, the probability of scattering is given by the fraction of the beam that is occluded by the scattering sites [HH Barrett]:

$$Pr[\text{scatter}] = -\frac{d\phi}{\phi} = n_e \times \sigma^C \times dx \quad (1.49)$$

where $\phi$ is the photon fluence in photons per square centimeters, $n_e$ is the electron density ($cm^{-3}$), $\sigma^C$ is the Compton collision cross-section ($cm^2 \times g^{-1}$), and $\mu_C$ is the Compton linear attenuation coefficient. The electron density $n_e$ is given by:

$$n_e = N_0 \times \rho \times \frac{Z}{A} \quad (1.50)$$

where $N_0$ represents Avogadro's number, $\rho$, A, and Z are respectively the material density, atomic weight and atomic number of the material under consideration. The number of photons scattered per unit volume is then given by:

$$\frac{dN_s}{dV} = -\frac{d\phi}{dx} = \phi \times n_e \times \sigma^C \quad (1.51)$$

The differential cross-section $$\left(\frac{d\sigma^C}{d\Omega}\right)_\Psi$$

is defined such that $d\sigma^C$ is the probability that an incident photon will be deflected into the elemental solid angle $d\Omega$ when passing through an attenuator containing one scattering per unit area, at angle $\psi$. According to this definition:

$$\sigma^C = 2\pi \int_0^\pi \left(\frac{d\sigma^C}{d\Omega}\right)_\Psi \times \sin(\Psi) \times d\Psi \quad (1.52)$$

Differentiating equation (1.51) with respect to Ω leads to:

$$\left[\frac{d^2 N_s}{dVd\Omega}\right] = \phi \times n_e \times \left(\frac{d\sigma^C}{d\Omega}\right)_\Psi \quad (1.53)$$

The amount of energy $d^2 E_s$ that is scattered into an elementary solid angle $d\Omega$ from the elemental volume $dV$ is:

$$\left[\frac{d^2 E_s}{dVd\Omega}\right]_\Psi = (h\nu') \times \phi \times n_e \times \left(\frac{d\sigma^C}{d\Omega}\right)_\Psi \quad (1.54)$$

$$= (h\nu_0) \times \left(\frac{h\nu'}{h\nu_0}\right) \times \phi \times n_e \times \left(\frac{d\sigma^C}{d\Omega}\right)_\Psi$$

Considering now an annulus of radius dr located at distance r from the scattering center M, the amount of scattered energy from M into this radius is given by:

$$S_C = \int_{l=0}^{l=L} I'(l) \times \exp\left[-\bar{\mu} \times \frac{L-l}{\cos\Psi}\right] \times \left(\frac{d^2 E_s}{dVd\Omega}\right) \times d\Omega \times dV(l) \quad (1.55)$$

where $dV(l) = A \times dl$ and $I'(l)$ represents the illuminating intensity at position $l$ along the line-integral path $L$. The term within the exponential represents the attenuation from the elemental volume dV at position I along the line-integral path L to a point M' (in the annulus of radius dr); the term below the integral sign represents the amount of energy scattered into an elementary solid angle $d\Omega$ from the elemental volume dV.

A simple geometric argument shows that the solid angle $d\Omega$ is given by $$\frac{dA}{R^2}$$

where the elemental area dA is given by $dA = 2\pi \times r \times dr$ and $R^2 = [L-l]^2 + r^2$. The intensity I' is given by $I' = I_0 \times \exp(-\bar{\mu} \times l)$ and accordingly:

$$s = \int_{l=0}^{l=L} \left\{ I_0 \exp(-\bar{\mu}l) \exp\left(-\bar{\mu} \times \frac{L-l}{\cos\Psi}\right) \times n_e \times h\nu_0 \times \right. \quad (1.56)$$

$$\left. \left[\left(\frac{h\nu'}{h\nu_0}\right)(\Psi) \times \left(\frac{d\sigma^C}{d\Omega}\right)_\Psi\right] \times \left(\frac{2\pi \times r \times dr \times \cos\Psi}{[L-l]^2 + r^2}\right) \right\} dV(l)$$

The term in the square bracket is the well-known Klein-Nishina function, that lists the differential cross-sections as a function of incoming photon energy $h\nu_0$ and scatter angle $\Psi$. This function also gives the scattered photon energy as follows:

$$\frac{1}{h\nu'} - \frac{1}{h\nu_0} = \frac{1}{m_0 c^2} \times (1 - \cos\Psi) \quad (1.57)$$

and accordingly at diagnostic energies the scattered photon retains most of the impinging energy.

Assuming that all the atomic electrons participate in Compton scattering equally, then the Compton mass attenuation coefficient is given by:

$$\left(\frac{\mu}{\rho}\right)^C = \sigma^C \times (N_0 Z/A) \quad (1.58)$$

and accordingly the Compton mass attenuation coefficient is seen to depend on energy and Z/A. For all but the lightest elements, $$Z/A \approx 0.5. \quad (1.59)$$

Therefore almost all matter has essentially the same Compton mass attenuation coefficient. This is why CT scanners are often said to measure tissue density; the CT image really represents the distribution of linear attenuation coefficients (the characteristics measured by the line-integrals). However, $$\mu^C = \left(\frac{\mu}{\rho}\right)^C \times \rho \quad (1.60)$$

and as the term in braces is approximately constant, the Compton attenuation coefficient is seen to scale mostly with density and energy.

Figure 33:
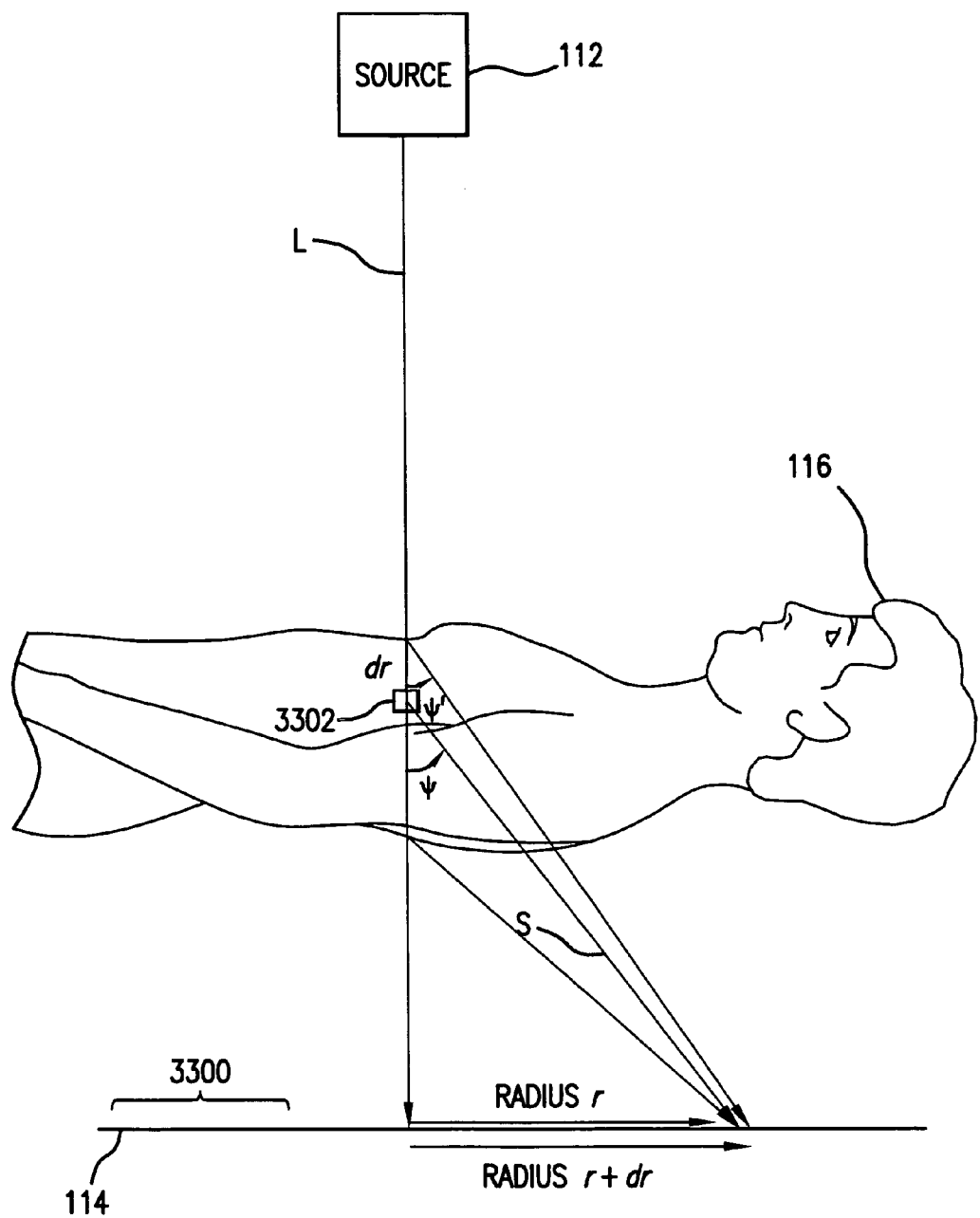
FIG. 33 illustrates the effect of scattering on a primary X-ray emissions path.

FIG. 33 shows physical processes for a single scatter forward calculation. A scatter center 3302 redirects radiation from primary path L along scatter path S from source 112 to detector array 114, and has elemental volume dV. In a first backprojection estimate, the total observed linear attenuation coefficient for linear path S is uniformly distributed along the path L between source 112 and surface 3300 of detector array 114. The scatter of rays is then estimated at each radius r+dr from the angle Ψ, as is the energy of the incoming radiation, and an estimate of the attenuation. This estimate is calculated for both Rayleigh and Compton scattering, according to the differential angular cross sections. The calculation may be repeated for angle Ψ' originating from a different scattering center. In computed tomography, voxel information allows a more accurate estimate of the forward scatter.

In a single-ray geometry, scatter energy measured outside of the primary detection pixel is integrated along circular bands of radii (r, r+dr). Starting with relatively large radii, the Rayleigh component may be considered small as compared to the Compton component. Accordingly, knowing the energy entering an elemental volume dV at location 3302 along the path L, the total energy scattered by the Compton phenomenon into the elemental area (at the detector surface between radii (r and r+dr) maybe calculated and compared with the actual data. A correction factor corresponding to the difference between the observed and calculated measurements can then be back projected along the ray. In this way, an improved estimate of the line attenuation coefficient is obtained. The calculation may be carried away for several radii in sequence and in an iterative manner.

By comparing the new estimate of the line integral with the original data, an estimate of the scattered radiation detected at the pixel where the primary radiation is measured is also obtained. Therefore scatter detection and analysis outside the primary beam may provide scatter compensation for those pixels directly illuminated by the primary beam.

In a scanning system, the object edge may be determined by monitoring the intensity of the primary radiation. It is clear that as the primary beam starts impinging onto the object to be imaged, only part of the beam is occluded, and this knowledge may be leverage to build a scatter-based refinement to the line integrals that is sequential in nature. In context of FIG. 33, the total scattered energy projected into an annulus centered onto the primary ray projection and of radius (r, r+dr) may be estimated knowing the impinging energy impinging on the object being imaged, and knowing an estimate of the line integral along path L. This estimate is compared to the measured scattered projection data, and the difference is back projected along the ray to provide an improved estimate of the line-integral.

In a fan-beam geometry, the energy collected at a given pixel outside of the projected primary beam corresponds to a finite sum of small annuli of various radii centered on each of the discrete projection pixel corresponding to the fan-beam projection. Accordingly, the scattered energy detected on a pixel-by-pixel basis must be compared against the sum of each ray contribution to the annulus intersecting this particular pixel, and weighted by the relative percentage of area of the pixel versus the annulus under consideration. The difference is then calculated as above, and distributed along each of the (discrete number of) projection rays in proportion according to the total relative contribution of a given ray to the pixel considered.

Section C.3 Volumetric CT Imaging with a Flat-Panel or Multi-Row Detector

A volumetric CT system may be designed with a flat-panel detector array 114, the longitudinal extent of which may be sufficient to geometrically allow imaging of a given object/patient/organ of interest in a single rotation. It is clear that with such a system, and with the benefit of sub-second rotation, it is possible to acquire multiple data sets, each corresponding to one rotation of the source at various beam spectra. Accordingly, M rotations permit decomposition of each line integral onto a subset of N (N<=M) spectral representations. These decompositions onto N spectral representations may be carried out through the CT image reconstruction, as chosen appropriately to the imaging configuration, through each image pixel, so that each reconstructed image pixel may now be represented onto N spectral basis functions. By way of example, under-collimation may occur in one embodiment where the primary beam projection covers only a subpart of a longitudinal or elongate primary detector area without covering other areas which collect scatter data only. The scatter data may be analyzed as described above for improved estimates of the line integrals.

Section C.2—Multi-row Detector CT Imaging in Spiral Mode

Figure 34A:
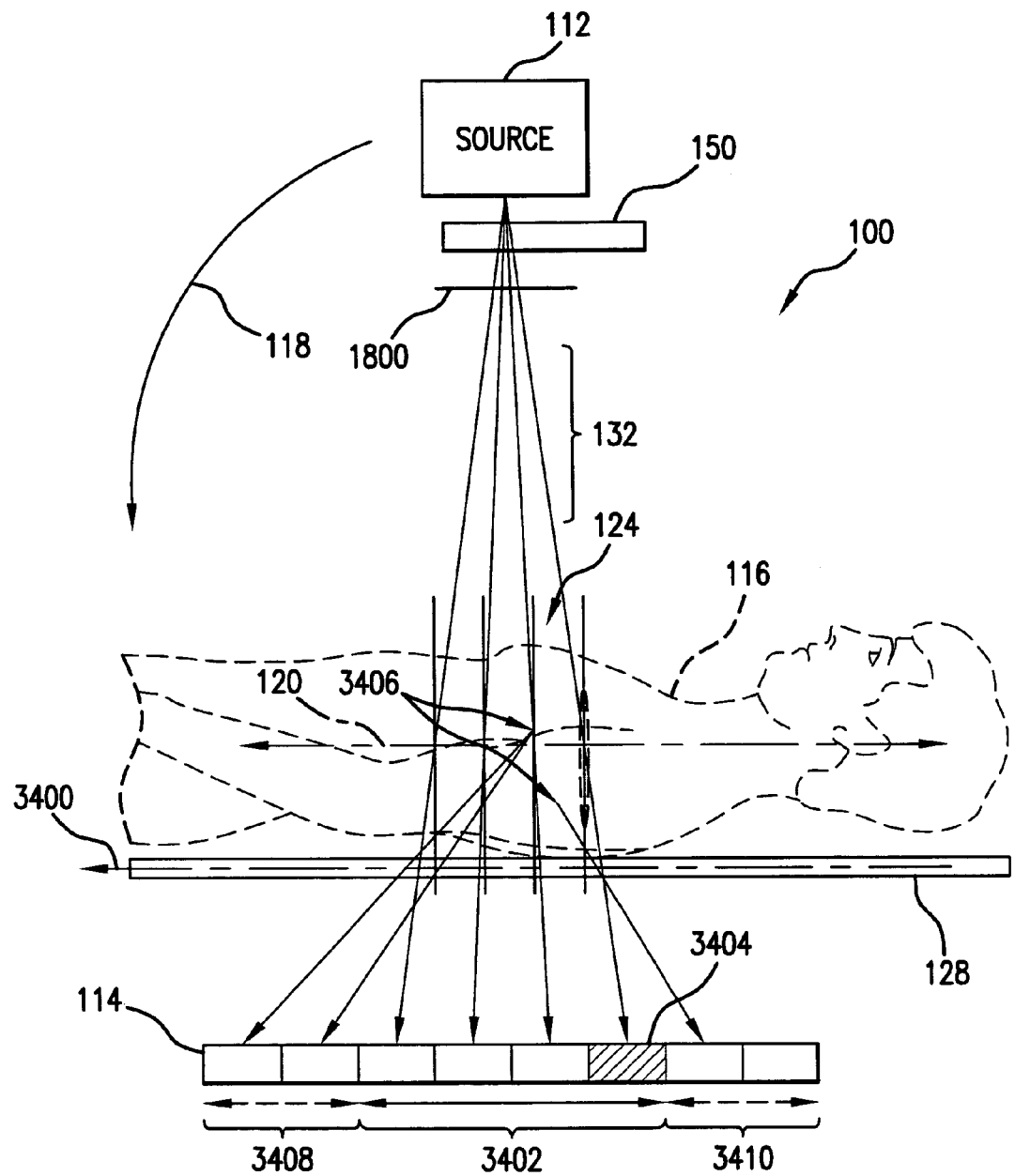
FIGS. 34A and 34B illustrates the effect of scatter in an X-ray imaging system, and illustrate the multiple sampling of essentially the same line-integral paths at two different spectra.

As shown in FIG. 34A, system 100 may be operated in a multi-slice spiral or helical mode where substantially the same line-integral is sampled at various source locations/detector row increments to provide multi-row computed tomography. This may be done, for example, by varying emissions spectra from the X-ray source 112 and filter 150 in synchrony with advance of the patient table 128 in direction 3400, and with a periodicity that reflects the number of rows and the row overlap per rotation or helical pitch. In one embodiment, the detector array 114 may have C columns and R rows, where the primary beam on paths 132 is directed towards primary rows 3402. Attenuation from a given structure of interest represented as dashed area 3411 in body 116 projects onto different rows at successive ones of T iterations. Scatters 3006 travel towards scatter rows 3408, 3410, and may be processed as described above to improve the primary image of body 116. In this geometry, under-collimation of the primary beam by collimator 1800 makes available selected active detector rows 3402, 3408, 3410, for scatter detection and measurement. The line-integral estimate improvements described above are carried through the reconstruction process, for example, in an iterative manner, to provide improved reconstructed voxel values. Successive scans of substantially the same line integrals may be performed with successive spectra. Accordingly system 100 may be a multi-slice CT system, and can be operated either in a scan/preview or helical/spiral mode.

Figure 34B:
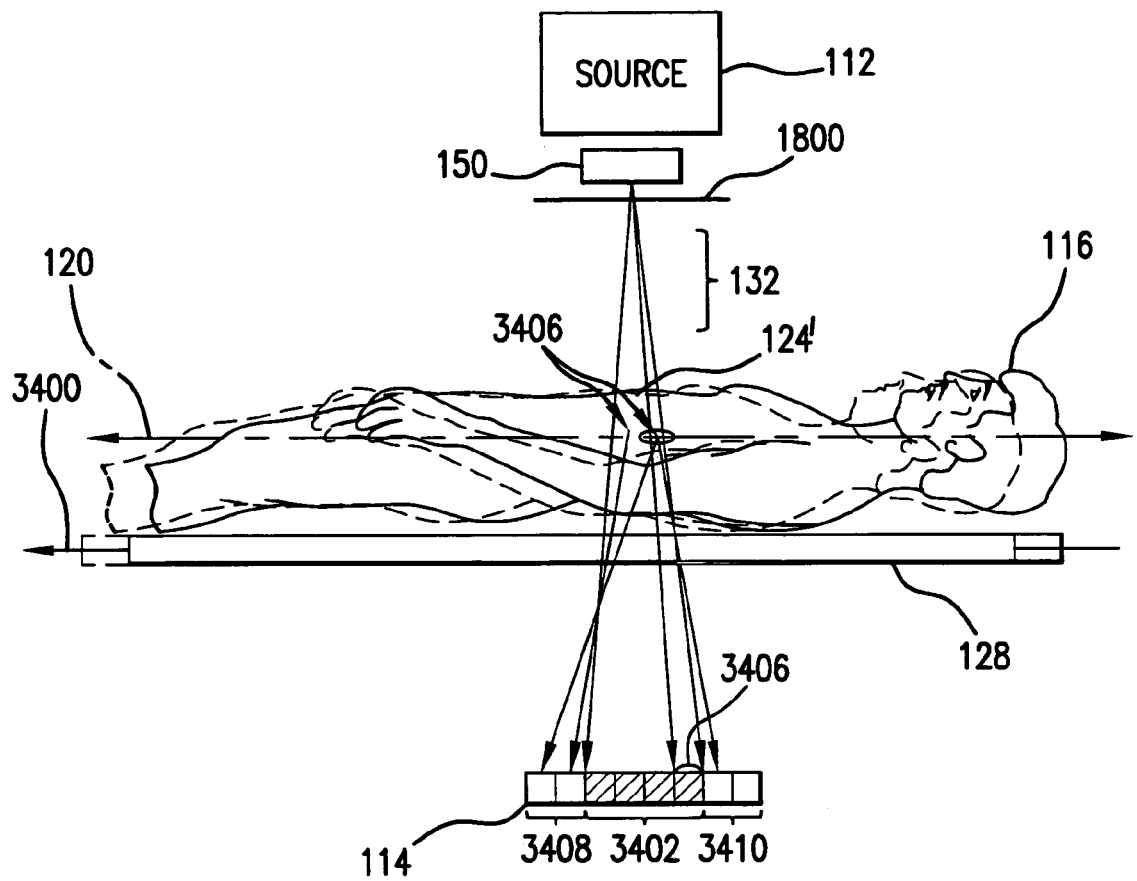

FIG. 34B shows an incremental advance of the body 116 through the system for additional scans rotations or half-rotations where the region 124' is spatially different from region 124 shown in FIG. 34A. By way of example, system 100 may be used for cardiac imaging with multi-slice CT, where the cardiac cycle may be decomposed into a number of segments, and each segment is imaged by a corresponding "sector" defined as a combination of source angular range (a T setting) and detector row and channel indices (a subset of the measurements corresponding to the spatial sector in synchronicity with patient advance). Each temporal segment in the cardiac cycle may be imaged with different spectra.

It is not necessary that the number of R rows equal the number of T iterations where, for example, the R detector rows may be classified or logically grouped into subdivisions. In this manner, a total of one hundred detector rows might be classified into subgroups of 40/60 or 20/20/20/10/30 and each subgroup may take on an iterative value of T with various ones of M spectra for a given X-ray path through the body. Each one of the paths 132 each for one of the T measurements may be defined as the direct distance of travel from the center of source 112 to the center of detector row groupings to the center of a detector row, depending upon the row-grouping schema.

Section C.4 Projection X-ray Imaging

Figure 35:
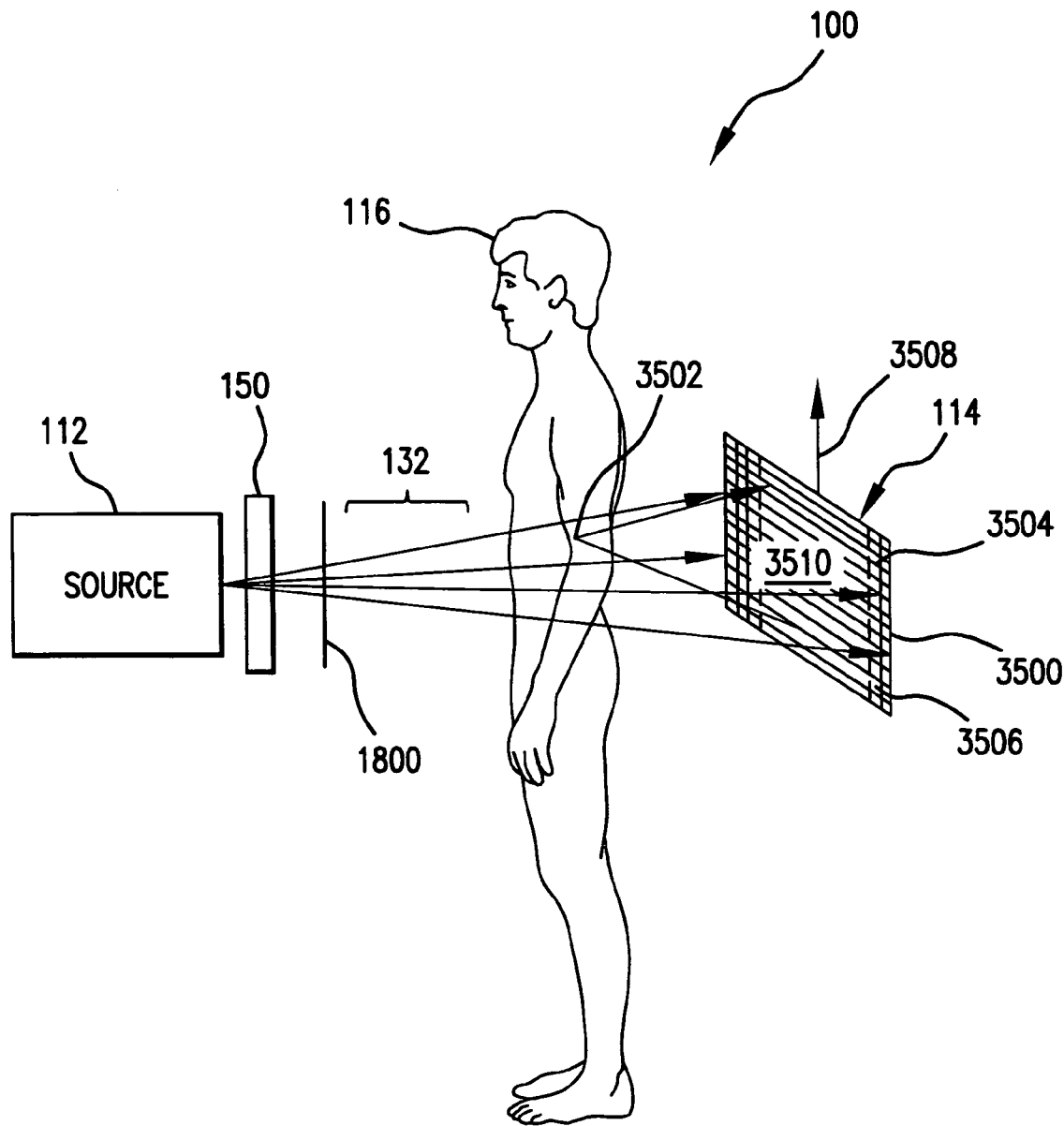
FIG. 35 illustrates the effect scattering in an X-ray imaging system and the use of an under-collimated beam.

System 100 may be operated in a variety of ways to perform projection imaging with direct scatter estimation from areas that impinge upon the detector array 114 outside of the projected primary beam. For example, FIG. 35 shows the body 116 being imaged in an upright configuration such that the undercollimated beam on primary paths 132 targets primary rows 3500 on detector array 114 with scatters 3502 impinging on scatter rows 3504, 3506. A vector 3108 indicates relative velocity between the primary beam on paths 132 and the detector array 114, for example, where the beam on paths 132 may be scanned from the source 112 and the collimator 1800 onto a stationary detector array 114, or the detector array 114 may itself be advanced for the scan. Where the detector array 114 has C columns and R rows, the primary rows 3500 may form a rectilinear overlay on area 3510 that is in parallel with the primary beam on paths 132.

Figure 36:
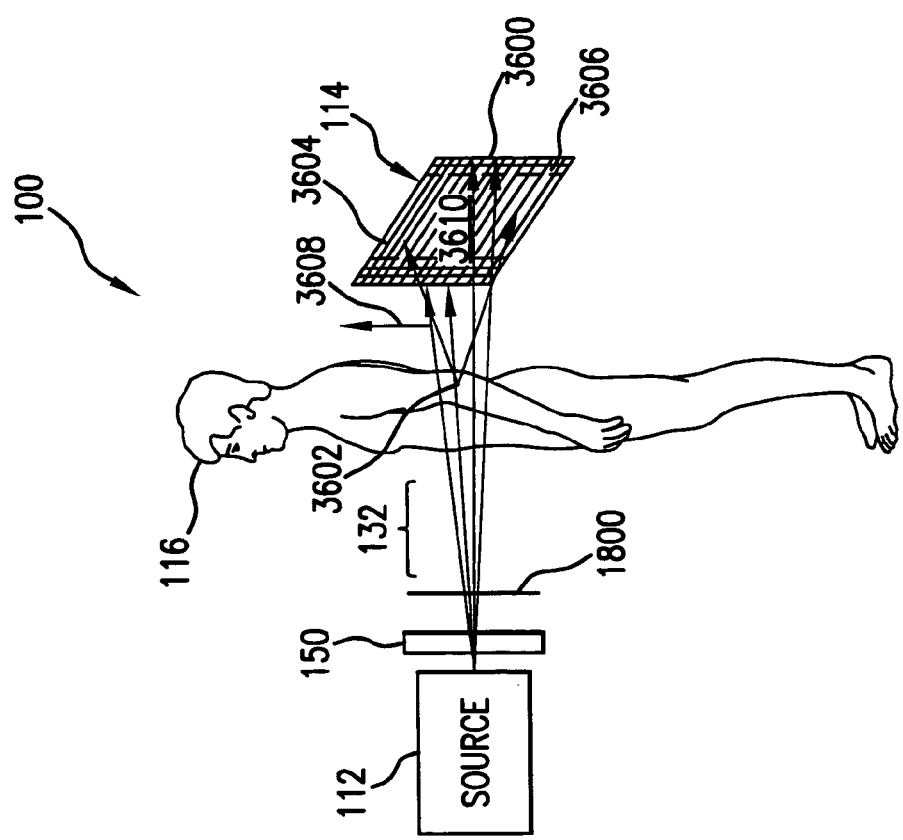
FIG. 36 illustrates the effect of scattering in an X-ray imaging system.

FIG. 36 shows another manner of operation with the body 116 being imaged in an upright configuration such that the undercollimated beam on primary paths 132 targets primary rows area 3600 on detector array 114 with scatters 3602 impinging on scatter areas 3604, 3606. A vector 3608 indicates relative velocity between the primary beam on paths 132 and the detector array 114, for example, where the beam on paths 132 may be scanned from the source 112 and the collimator 1800 onto a stationary detector array 114. Alternatively, the detector array 114 may itself be advanced for the scan. Where the detector array 114 has C columns and R rows, the primary area 3600 may form a rectilinear overlay on area 3610 that is not in parallel with the primary beam on paths 132, such that the primary area 3600 overlaps adjacent rows and columns and is not in rectilinear alignment with the column-grid format of detector array 114.

Figure 37:
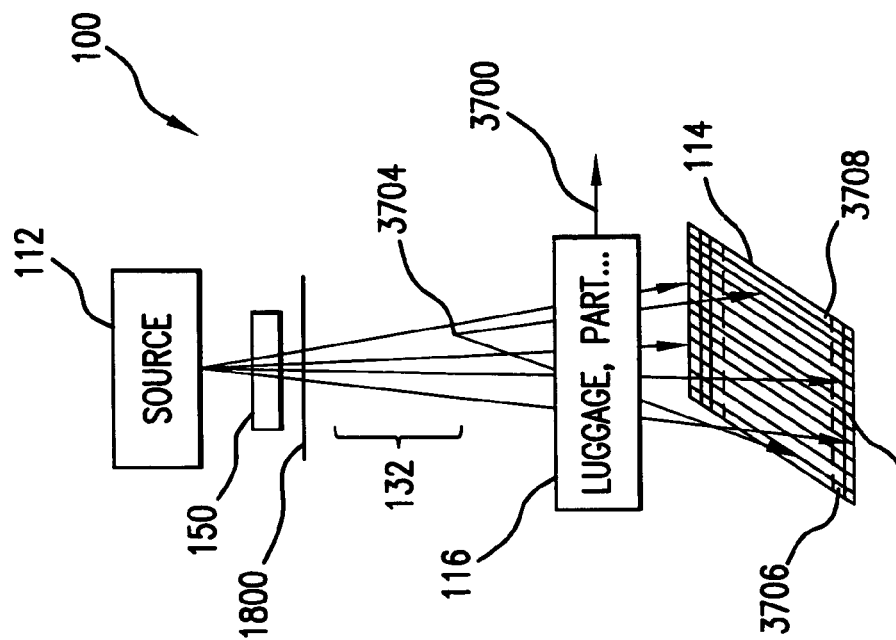
FIG. 37 illustrates the effect of scattering in an X-ray imaging system.

FIG. 37 shows another manner of operation where the body 116 may be luggage or a part that is advanced on a conveyor system 3700 in a direction that is generally transverse with respect to the primary beam on paths 132, which impinges upon detector array 114 to form primary area 3702. Scatters 3704 are directed towards scatter areas 3706, 3708. The source 112 and detector array 114 may be held stationary.

Section C.5—Volume Scatter Detection

Figure 38:
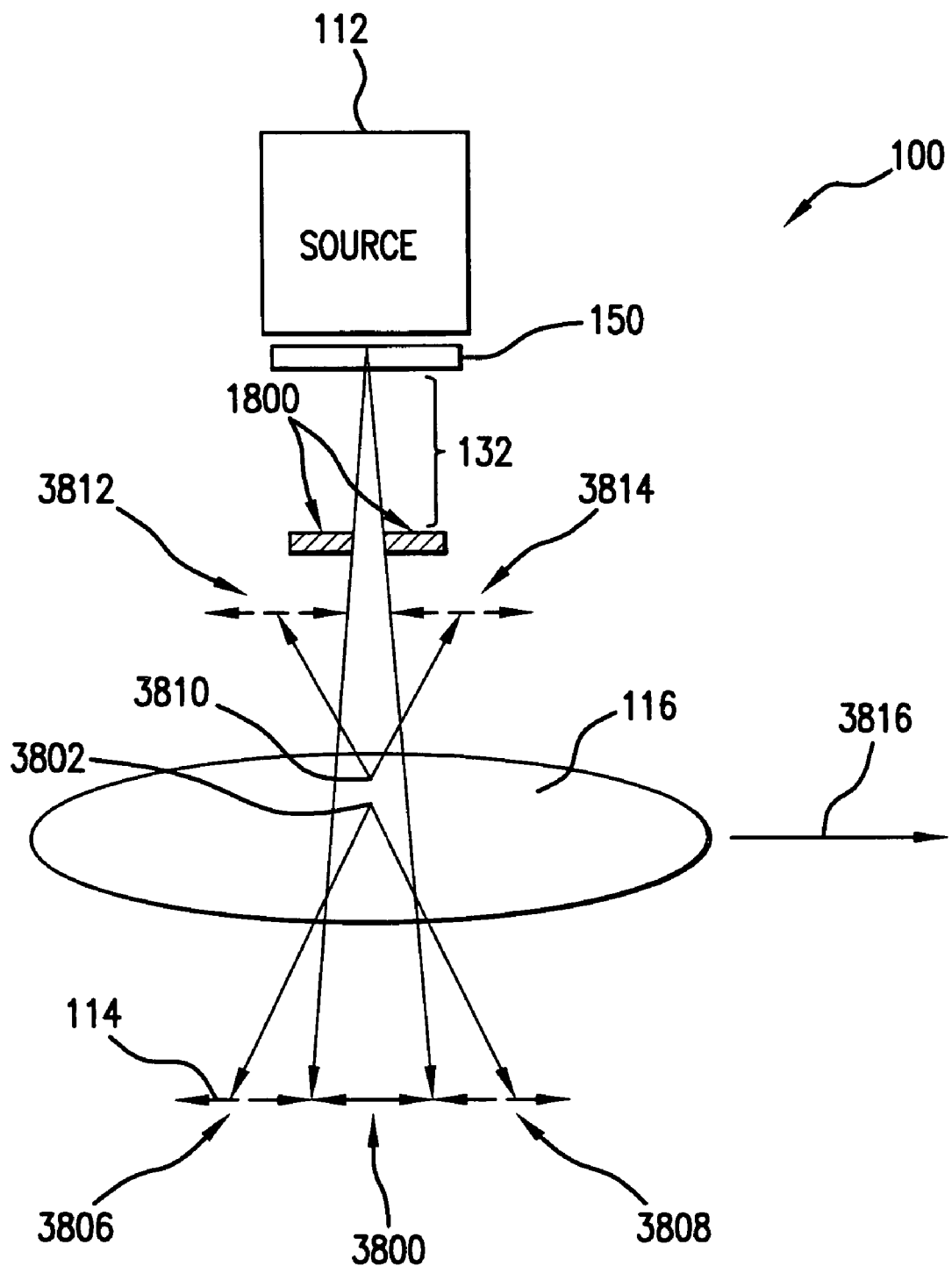
FIG. 38 shows the use of detector positioning to accommodate or correct for back projection scattering in an X-ray imaging system.

A significant amount of the scattered radiation never impinges upon detector array 114, which is located to detect the primary beam on paths 132 opposite the X-ray source 112 with respect to the patient. This is because the intensity of the impinging beam is much larger on the source side, and the differential scatter cross-sections, particularly the Compton cross-sections, include large components for scatter at very large angles. Accordingly, additional detectors may be provided to detect scatter, for example, by enclosing the body 116 with a sphere of detectors. In practical implementations, detectors may be placed proximate source 112 and/or close to the primary beam on paths 132 to collect large amount of Compton scatters. These additional detectors may be leveraged to improve the line-integral estimates, as described above. FIG. 38 shows one such embodiment where the primary beam on paths 132 is focused upon a primary target area 3800 of detector array 114, and a portion of total scattering indicated as scatters 3802 impinges upon scatter areas 3806, 3808. Another portion of total scattering indicated as 3810 is backprojected by the physical nature of scattering onto additional detectors 3812, 3814, which are positioned proximate source 112 and paths 132 relative to the detector array 114. The detectors 3812, 3814 may have a row-column array format that is suited to capture and resolve scatter calculations, as described above. Motion 3816 indicates a positional change or directional advance of body 116 relative to paths 132.

Figure 39:
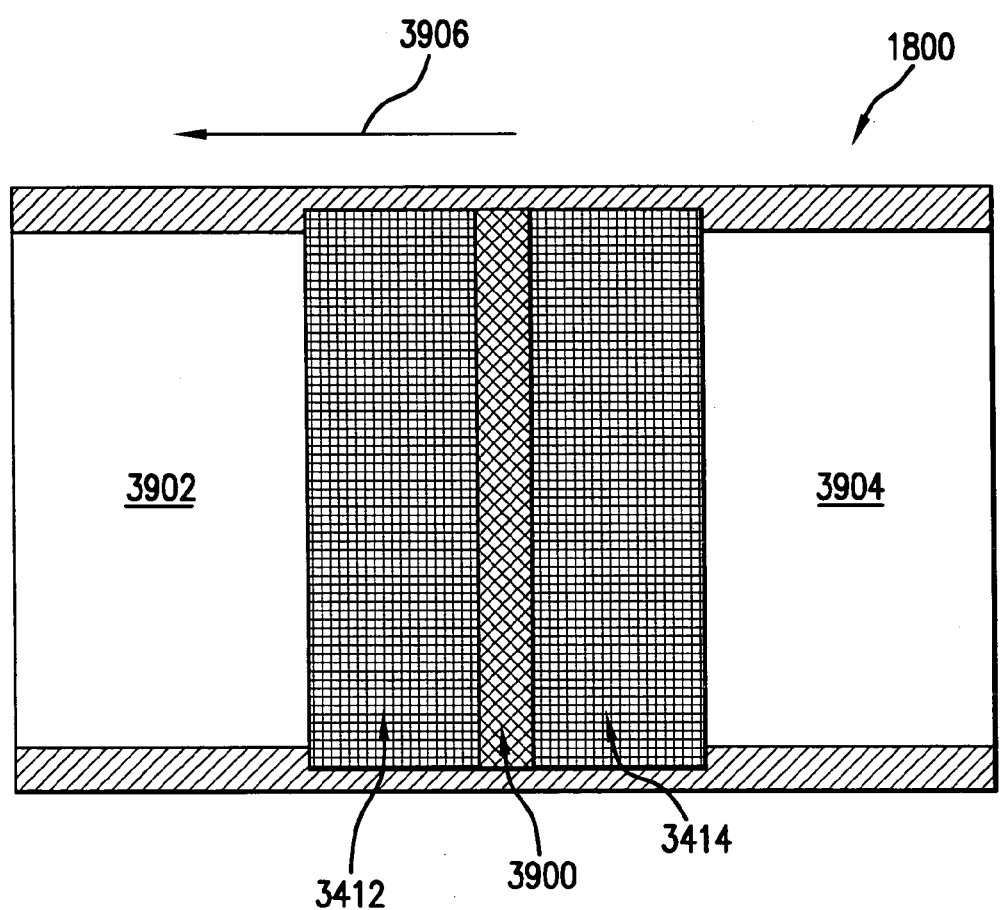
FIG. 39 shows an X-ray source having an exit slit bounded by collimator and detector assemblies for use in detecting back projection scattering.

FIG. 39 shows one embodiment of collimator 1800, such that an X-ray exit slit 3900 is defined by detectors 3912, 3914. The detectors 3912, 3914 are mounted on flanges 3902, 3904, which also define the X-ray exit slit 3900 and shield detectors 3912, 3914 from radiation on the source side opposite that shown in FIG. 39, so that detected signals in detectors 3912, 3914 are not corrupted by primary radiation. Collimator 1800 may be provided with electronically controlled actuation (not shown) permitting computing equipment 122 to reposition the collimator 1800, for example, by movement in the direction of arrow 3906 for scanning purposes.

Section D—CAD Improved DMXI Imaging with Computer Aided Detection and Diagnosis (all Projection and CT Imaging)

The role of CAD in radiology is increasing significantly, and state-of-the-art CAD systems are emerging as clinically relevant tools. Multi-spectral imaging may increase lesion conspicuity. Decomposed multispectral components (images) may also provide quantitative data to enhance specificity and selectivity of the diagnostic procedure, for example, in chest radiography. The availability of multi-spectral projection data may improve the usefulness of CAD systems.

In one embodiment, the system 100 operates a CAD analysis software according to a set of expert-defined rules. For example, a breast cancer may be determined empirically to yield a particular line-integral function pattern as projected onto the detector. These line-integral functions may be normalized to provide a database of known results against which comparisons may be made according to expert defined rules that characterize the image patterns as being distinct from healthy tissue. A predetermined system of comparison may be established according to these rules to flag instances of probable disease. The locations of pixels that are associated with a disease image area may be, for example, color coded for superposition of a colorized disease location upon an image of the patient's torso. In other embodiments, line-integral functions that are confirmed as being associated with a particular disease are used to train a neural network or other computer-assisted learning algorithm. For example, the full-spectrum line functions associated with disease may be parsed into sections, features, or sub-bands, together with line functions for healthy tissues. The neural network may be trained to discriminate between diseased tissues and healthy tissues on this basis to enhance screening or diagnostic specificity and accuracy.

Section D.1—Computer Aided Detection and Diagnosis for Multi- and Hyper-Spectral Data Sets The discussion below describes multi- or hyper-spectral computer image analysis. Previously disclosed approaches provide co-registered projection or reconstructed slice image data that are suitable for application to CAD by representing projection data information along multiple dimensions, e.g., as the basis functions. Approaches to CAD rely mostly on spatial analysis of one projection, or several projections that are acquired at various angles. This discussion pertains to increasing the sensitivity and specificity of CAD by simultaneously utilizing several co-registered and co-temporal image planes, which are the multispectral x-ray projection basis function decompositions, as projected representations of the same imaged object or patient. Such CAD improvements may be useful in the automated detection and characterization of cancer in medical imaging, of foreign/suspect objects and substances in industrial and luggage inspections, together with automatic detection, characterization and identification of specific targets of interest.

Section D.2—Background and Method

Figure 41:
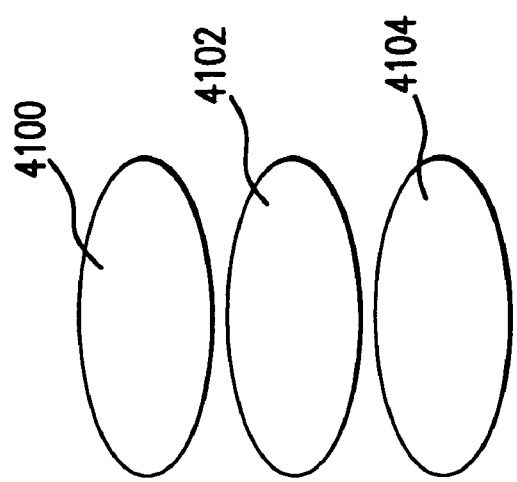
FIG. 41 shows a stack of multi-spectral reconstructed images or decomposed reconstructed images for use in CAD.
Figure 40:
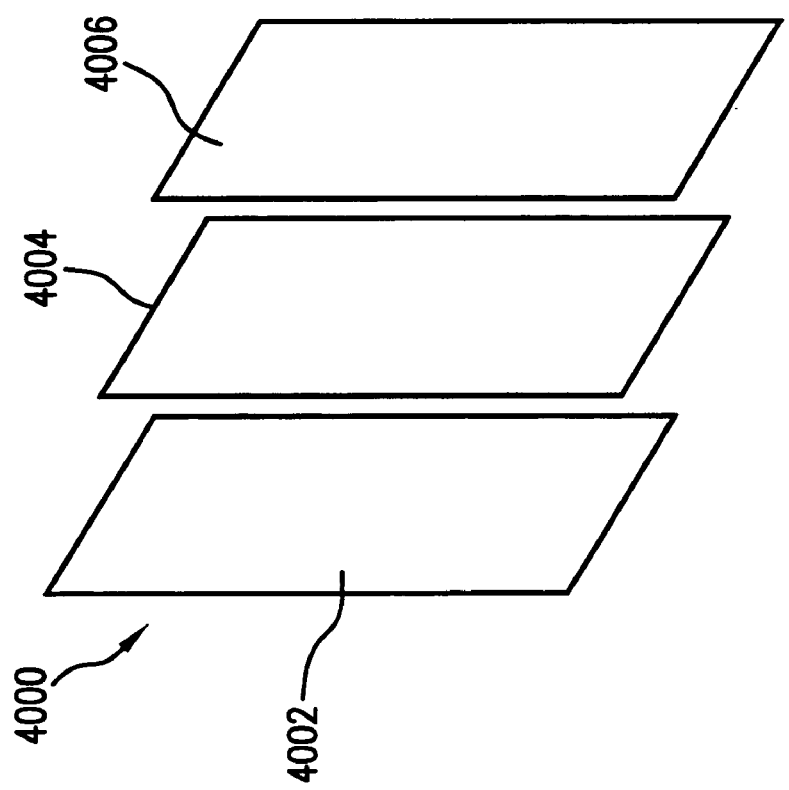
FIG. 40 shows a stack of multi-spectral projection images or multispectral decomposed projection images for use in CAD.

Multi-spectral data acquisition methods may provide different sets of co-registered data, for example, as shown in FIG. 40. A stack of multi-spectral or hyper-spectral co-registered images may be obtained for one projection and decomposed onto multiple basis function images 4002, 4004, 4006. Further, as shown in FIG. 41, linearity of the CT image reconstruction process facilitates reconstruction of multi-spectral CT projection data onto multiple images for each 2D slice of a 3D volume, and such images can then be decomposed onto multiple basis function images 4100, 4102, 4104. Either of these types of data sets can form an input to a generalized CAD algorithm.

A Bayesian model is now introduced that assumes the result of known CAD algorithms working on each basis function. The model then integrates the likelihood that for each basis function, the image contains a feature of interest (such as cancer in medical imaging or a particular type of explosive substance in luggage screening, etc.) to form an overall probability of presence (detection). Further, the nature of the decomposition permits a characterization of the suspicious area detected. That is, given the unique spectral signature of target elements, image decomposition onto a related basis function with a non-zero weight provides a relative indication of the likelihood of the given type of lesion/material being present in the imaged body.

Generally, a Bayesian model can incorporate a-priori information via the specification of a prior distribution, for example, as shown in equation 1.61:

$$P_{a\text{-}posteriori}(M|D) = P_{likelihood}(D|M) \times P_{a\text{-}priori}(M)/p(D) \quad (1.61)$$

where D are the decomposed data; which may be either multi-spectral decomposed projection data or multi-spectral decomposed reconstructed data; and M is a CAD model. The CAD model may be obtained by applying known CAD methods onto each basis function separately, for example, by spatial analysis of clusters, nodules, tumors, tumors margins, and any of a large number of malignancy indicators in a medical application. The CAD model may further establish linkages between basis functions. Further, the CAD model may depend on an adaptive database of known-cases, which are sometimes referred togas ground truths. The CAD model may alternatively be design to evolve as a function of time, such as by a learning period characteristic of neural networks.

By way of example, the Markov Random Field (MRF) class of probability distribution provides one way to establish linkage across the various basis functions. MRFs offer a practical and powerful means to model local structure and properties of images without having to characterize a full set of images (REFS). Information collected locally can then influence the a-posteriori distribution and therefore the maximum a-posteriori (MAP) estimate of the model. MRF distributions are conveniently described by neighborhood cliques and Gibbs distribution. A powerful multivariate optimization algorithm had been described, that allows finding global extrema while escaping local minima/maxima. The iterative simulated annealing method (REF) is known to converge to the global multivariate function extrema under general conditions.

Section D.4—Hyper-spectral Computer Aided Detection and Diagnosis

As shown above, the nature of the imaging methods that are used by system 100 to image a given body may vary very significantly. For example, co-registered images or "fusion images" of dual-modalities are commonly obtained as a result of the use of both positron emission tomography (PET) and computed tomography (CT) imaging. Other examples include the co-registration of single photon emission computed tomography (SPECT) and CT images. In these two last examples, the emission modality is considered to provide functional images, that are co-registered with anatomical images as commonly obtained via CT.

Further examples include co-registered images of ultrasound and X-ray projection. The combination of these two modalities has been shown to significantly increase the sensitivity and specificity of imaging as compared to any of these two modalities taken alone. Other possible applications in medical imaging include the use of MRI, thermal imaging, and any of a number of modalities capable of generating projection images.

While co-registration may reflect or follow system design, a number of image processing methods have been developed to perform elastic registration of two or more images that were not acquired simultaneously or may refer to somewhat different anatomical locations. Thus, the discussion below pertains to the use of additional data that may be used or processed in association with the X-ray imaging results obtained from system 100. By way of example, the additional data modalities may include radar, ultrasound, magnetic resonance imaging or optical data acquired at various spectral frequencies.

The discussion above assumes that projection or reconstruction data from the various modalities are either acquired in a co-registered manner or have been preprocessed for registration via registration software. The CAD algorithm then proceeds from the co-registered multi- or hyper-spectral data to provide automatic identification/detection, characterization and classification.

D. The Following are Incorporated Herein by Reference:

Barrett H H and Swindell W. Radiological Imaging. The Theory of Image Formation, Detection, and Processing. Academic Press, 1981.

Besson G M. "Computed tomography (CT) weighting for high quality image reconstruction." U.S. Pat. No. 6,463,118, 2000.

Besson G M. "CT projection estimation and applications to fast and local reconstruction." Proc. SPIE 3661, 1196–1207, 1999.

Besson G M. "Methods and apparatus for cone-beam multislice CT correction." U.S. Pat. No. 6,459,754, 1999.

Besson G M. U.S. Pat. No. 6,246,742. "Local CT image reconstruction with limited x-ray exposure," 1999.

Boone J M, "X-ray Production, Interaction, and Detection in Diagnostic Imaging," in Handbook of Medical Imaging, Volume 1. Physics and Psychophysics. Beutel J, Kundel, H L, Van Metter R L, editors. SPIE Press, 2000.

Johns H E and Cunningham J R. The Physics of Radiology. Charles C Thomas Publisher, Fourth edition, 1983.

Price J S and Drory M D. U.S. Pat. No. 6,560,315 B1. "Thin rotating plate target for x-ray tube," 2003.

Rand R E, Boyd D P, Peschmann K R. U.S. Pat. No. 4,993,055. "Rotating x-ray tube with external bearings," 1991.

Rand R E, Boyd D P, Peschmann K R. U.S. Pat. No. 5,105,456. "High duty-cycle x-ray tube," 1992.

Rand R E, Tsiang E Y. U.S. Pat. No. 5,193,105. "Ion controlling electrode assembly for a scanning electron beam computed tomography scanner," 1993.

Rand R E. U.S. Pat. No. 4,521,901. "Scanning electron beam computed tomography scanner with ion aided focusing," 1985.

Rand R E. U.S. Pat. No. 5,386,445. "Method and apparatus for electron beam focusing adjustment by electrostatic control of the distribution of beam-generated positive ions in a scanning electron beam computed tomography scanner," 1995.

Ratzmann P M. U.S. Pat. No. 6,418,192 B1. "Multiple row x-ray tube bearing assembly," 2002.

Salb, J. "System and method for radiographic imaging of tissue." U.S. Pat. No. 6,226,352 B1, 2001.

Smith B D, Singh T. "Fan-beam reconstruction from a straight line of source points," IEEE Transactions on Medical Imaging, Vol. 12(1), 1993.

Smith R B. U.S. Pat. No. 6,456,692 B1. "High emissive coatings on x-ray tube components," 2002.

Sobol W T, "High-frequency x-ray generator basics." Med. Phys. 29(2), February 2002.

I claim:

1. A method of acquiring multispectral x-ray projection data of an object with an imaging apparatus, comprising:
    (a) Selecting an x-ray source x-ray radiation spectral characteristics by adjusting at least two parameter values from the group consisting of (i) an x-ray tube target track material, (ii) a generator peak kilo-voltage, (iii) an x-ray tube current, (iv) a filter composition, and (v) an x-ray tube focal spot size;

(b) projecting, in a first relative orientation between the object and x-ray imaging apparatus, x-ray radiation according to selecting step (a) through the object and acquiring a first set of measurements defining a first set of projection lines through the object;

(c) for at least one additional relative orientation between the object and the x-ray imaging apparatus, projecting x-ray radiation according to selecting step (a) through the object and acquiring an additional set of measurements defining an additional set of projection lines through the object, the additional set of projection lines overlapping, at least in part, with the first set of projection lines; and (d) repeating steps (a) through (c) for at least two different parameter values;

wherein multispectral sets of projection data are acquired for the object at a multiplicity of x-ray spectra in a single scan for the object through the imaging apparatus.

2. The method of claim 1, further comprising filtering projected x-ray radiation through the object using a double filter wheel.

3. The method of claim 2, further comprising independently controlling each filter of the double filter wheel.

4. The method of claim 1, further comprising digitally processing the acquired projection data to increase projection data signal-to-noise ratio.

5. The method of claim 4, the digital processing comprising sorting and averaging the acquired projection data.

6. The method of claim 4, the digital processing comprising utilizing statistical methods.

7. The method of claim 1, wherein selecting step (a) further comprises analyzing data collected during the scan and selecting the parameter values as a function of the object x-ray attenuation currently present along the x-ray projection lines.

8. The method of claim 1, further comprising setting the position of an x-ray beam with respect to a detector based upon the acquired projection data.

9. The method of claim 8, wherein setting the position of the x-ray beam comprises determining current position of the x-ray beam with respect to the detector.

10. The method of claim 1, further comprising recording signal information for a patient electrocardiogram or respiratory trace simultaneously to x-ray data acquisition during the scan.

11. The method of claim 10, further comprising sorting acquired x-ray projection data according to the recorded electrocardiogram or respiratory signal information.

12. The method of claim 1, further comprising measuring air signal and performing calibration and correction steps to provide estimates of line integrals of the object being imaged.

13. The method of claim 1, wherein projecting step (b) comprises illuminating part of a detector directly by a primary x-ray beam projection and measuring scattered radiation with the detector outside the primary beam projection.

14. The method of claim 13, further comprising estimating a scatter signal collected together with a primary signal from the scatter data measured outside the primary beam projection.

15. The method of claim 14, further comprising subtracting the estimated scatter signal from the recorded primary and scatter data to obtain an estimate of the primary signal.

16. The method of claim 1, wherein step (b) of projecting x-ray radiation comprises operating the x-ray source in a pulsed mode or a continuous mode.

17. A method of acquiring multispectral computed tomography data of an object with a computed tomography apparatus, comprising:

(a) selecting an x-ray source x-ray radiation spectral characteristics by adjusting at least two parameter values from the group consisting of (i) an x-ray tube target track material, (ii) a generator peak kilo-voltage, (iii) an x-ray tube current, (iv) a filter composition, and (v) an x-ray tube focal spot size;

(b) projecting, for at least one relative orientation between the x-ray source and the object, x-ray radiation according to the selecting step (a) through the object and acquiring a first set of measurements defining a first set of projection lines through the object;

(c) repeating steps (a) and (b) in a different relative orientation between the x-ray source and the object, such that at least two sets of projection lines through the object are acquired at at least two spectra;

wherein projection data sets acquired in a single scan for the object through the computed tomography apparatus are sufficient for the generation of at least two computed tomography image estimates at at least two spectra for at least part of one cross section of the object.

18. The method of claim 17, further comprising filtering projected x-ray radiation through the object using a double filter wheel.

19. The method of claim 18, further comprising independently controlling each filter of the double filter wheel.

20. The method of claim 17, comprising acquiring the data for each projection line spectral data set corresponding to one object cross section with a source excursion greater than 720 degrees.

21. The method of claim 20, further comprising weighting the acquired data prior to reconstruction to account for data redundancy.

22. The method of claim 17, comprising acquiring the data for each projection line spectral data set corresponding to one object cross section with a source excursion greater than 360 degrees.

23. The method of claim 22, further comprising weighting the acquired data prior to reconstruction to account for data redundancy.

24. The method of claim 17, comprising acquiring the data for each projection line spectral data set corresponding to one object cross section with a source excursion less than 360 degrees.

25. The method of claim 24, further comprising weighting the acquired data prior to reconstruction to account for data redundancy.

26. The method of claim 17, wherein projecting step (b) comprises illuminating part of a detector directly by a primary x-ray beam projection and measuring scattered radiation with the detector outside the primary beam projection.

27. The method of claim 26, further comprising estimating a scatter signal collected together with a primary signal from the scatter data measured outside the primary beam projection.

28. The method of claim 27, further comprising subtracting the estimated scatter signal from the recorded primary and scatter data and obtaining an estimate of the primary signal.

29. The method of claim 17, comprising changing the x-ray spectral parameters from one view to the next such that at least two sets of projection data each sufficient for image reconstruction are acquired for at least part of one object cross section for each source rotation of at least 360 degrees.

30. The method of claim 17, wherein selecting step (a) comprises analyzing data collected during the scan and selecting the parameter values as a function of the object x-ray attenuation currently present along the x-ray projection lines.

31. The method of claim 17, further comprising recording signal information for a patient electrocardiogram or respiratory trace simultaneously to x-ray data acquisition during the scan.

32. The method of claim 31, further comprising sorting the acquired x-ray projection data according to the recorded electrocardiogram or respiratory signal information.

33. The method of claim 17, wherein step (b) of projecting x-ray radiation comprises operating the x-ray source in a pulsed mode or a continuous mode.

34. A method of acquiring multispectral limited-angle computed tomography or tomosynthesis data of an object with an x-ray imaging system, comprising:
  (a) selecting an x-ray source x-ray radiation spectral characteristics by adjusting at least two parameter values for the group consisting of (i) an x-ray tube target track material, (ii) a generator peak kilo-voltage, (iii) an x-ray tube current, (iv) a filter composition, and (v) an x-ray tube focal spot size;
  (b) projecting, for at least one relative orientation of the x-ray source with respect to the object, x-ray radiation according to the selecting step (a) through the object and acquiring a first set of measurements defining a first set of projection lines through the object;
  (c) repeating steps (a) and (b) in a different relative orientation of the x-ray source with respect to the object, such that at least two sets of projection lines through the object are acquired at at least two spectra;
  wherein projection data sets acquired of the object in a single scan for the object through the x-ray imaging system are sufficient for the generation of at least two limited-angle computed tomography or tomosynthesis image estimates at at least two spectra for at least part of one cross section of the object.

35. The method of claim 34, wherein step (c) of repeating steps (a) and (b) in a different relative orientation of the x-ray source with respect to the object comprises moving an x-ray tube along a trajectory.

36. The method of claim 34, wherein step (c) of repeating steps (a) and (b) in a different relative orientation of the x-ray source with respect to the object comprises deflecting a focused electron beam along an x-ray target.

37. The method of claim 34, further comprising filtering projected x-ray radiation through the object by mechanically advancing at least one x-ray filter sheet in front of the source.

38. The method of claim 34, further comprising digitally processing the acquired projection data to increase the projection data signal-to-noise ratio.

39. The method of claim 38, the digital processing comprising sorting and averaging the data.

40. The method of claim 38, the digital processing comprising using statistical methods.

41. The method of claim 34, wherein selecting step (a) comprises analyzing data collected during the scan and selecting the parameter values as a function of the object x-ray attenuation currently present along the x-ray projection lines.

42. The method of claim 34, further comprising setting the position of an x-ray beam with respect to a detector based upon the acquired projection data.

43. The method of claim 42, wherein setting the position of the x-ray beam comprises determining current position of the x-ray beam with respect to the detector.

44. The method of claim 34, further comprising recording signal information for a patient electrocardiogram or respiratory trace simultaneously to x-ray data acquisition during the scan.

45. The method of claim 44, further comprising sorting acquired x-ray projection data according to the recorded electrocardiogram or respiratory signal information.

46. The method of claim 34, further comprising measuring air signal and performing calibration and correction steps to provide estimates of line integrals of the object being imaged.

47. The method of claim 34, wherein projecting step (b) comprises illuminating part of a detector directly by a primary x-ray beam projection and measuring with the detector scattered radiation outside the primary beam projection.

48. The method of claim 47, further comprising estimating a scatter signal collected together with a primary signal from the scatter data measured outside the primary beam projection.

49. The method of claim 48, further comprising subtracting the estimated scatter signal from the recorded primary and scatter data to obtain an estimate of the primary signal.

50. The method of claim 34, wherein step (b) of projecting x-ray radiation comprises operating the x-ray source in a pulsed mode or a continuous mode.

51. The method of claim 34, further comprising weighting the acquired projection data prior to reconstruction to account for the geometry of the x-ray acquisition system.

52. The method of claim 34, wherein the generation of limited-angle computed tomography or tomosynthesis reconstructed images comprises performing a filtered-back-projection method.

53. The method of claim 34, wherein the generation of limited-angle computed tomography or tomosynthesis reconstructed images comprises performing a matrix inversion method.

54. The method of claim 34, wherein the generation of limited-angle computed tomography or tomosynthesis reconstructed images comprises performing an iterative method.

55. The method of claim 54, wherein performing an iterative reconstruction method further comprises using a-priori information.

* * * * *